United States Patent
Lahoud et al.

(10) Patent No.: US 9,988,431 B2
(45) Date of Patent: Jun. 5, 2018

(54) DENDRITIC CELL MARKER AND USES THEREOF

(71) Applicant: Walter and Eliza Hall Institute of Medical Research, Parkville, Victoria (AU)

(72) Inventors: Mireille Hanna Lahoud, East Melbourne (AU); Anna Irene Proietto, Bulleen (AU); Irina Caminschi, Ascot Vale (AU); Ken Shortman, Princess Hill (AU); Andrew Mark Lew, Essendon (AU); Li Wu, Ascot Vale (AU); Mark Dexter Wright, Northcote (AU)

(73) Assignee: The Walter and Eliza Hall Institute of Medical Research (AU)

( * ) Notice: Subject to any disclaimer, the term of this patent is extended or adjusted under 35 U.S.C. 154(b) by 7 days.

(21) Appl. No.: 13/848,503

(22) Filed: Mar. 21, 2013

(65) Prior Publication Data

US 2013/0273150 A1    Oct. 17, 2013

Related U.S. Application Data

(63) Continuation of application No. 12/675,392, filed as application No. PCT/AU2008/001294 on Aug. 29, 2008, now Pat. No. 8,426,565.

(60) Provisional application No. 60/969,118, filed on Aug. 30, 2007, provisional application No. 61/052,865, filed on May 13, 2008.

(51) Int. Cl.

| C07K 1/00 | (2006.01) |
|---|---|
| C07K 14/00 | (2006.01) |
| C07K 17/00 | (2006.01) |
| C07K 14/705 | (2006.01) |
| A61K 39/385 | (2006.01) |
| A61K 47/48 | (2006.01) |
| A61K 51/10 | (2006.01) |
| C07K 16/18 | (2006.01) |
| C12N 15/82 | (2006.01) |
| G01N 33/50 | (2006.01) |
| A61K 39/39 | (2006.01) |
| A61K 39/00 | (2006.01) |
| G06F 19/16 | (2011.01) |

(52) U.S. Cl.
CPC .......... *C07K 14/705* (2013.01); *A61K 39/385* (2013.01); *A61K 39/39* (2013.01); *A61K 47/48561* (2013.01); *A61K 51/1027* (2013.01); *C07K 14/7056* (2013.01); *C07K 16/18* (2013.01); *C12N 15/8258* (2013.01); *G01N 33/5005* (2013.01); *G01N 33/5047* (2013.01); *A61K 2039/6056* (2013.01); *C07K 2317/73* (2013.01); *G01N 2333/42* (2013.01); *G01N 2333/4724* (2013.01); *G06F 19/16* (2013.01)

(58) Field of Classification Search
None
See application file for complete search history.

(56) References Cited

U.S. PATENT DOCUMENTS

| 6,491,918 | B1 | 12/2002 | Thomas et al. |
|---|---|---|---|
| 8,426,565 | B2 | 4/2013 | Lahoud et al. |
| 2002/0042386 | A1 | 4/2002 | Rosen et al. |
| 2003/0059875 | A1 | 3/2003 | Rosen et al. |
| 2007/0099251 | A1 | 5/2007 | Zhang et al. |
| 2010/0221265 | A1 | 9/2010 | Sancho-Madrid et al. |
| 2011/0110861 | A1 | 5/2011 | Lahoud et al. |
| 2012/0039806 | A1 | 2/2012 | Lahoud et al. |

FOREIGN PATENT DOCUMENTS

| EP | 1516881 | 6/2010 |
|---|---|---|
| WO | WO 1992001935 | 2/1992 |
| WO | WO 2003025130 | 3/2003 |
| WO | WO 2003054152 | 7/2003 |
| WO | WO 2003091435 | 11/2003 |
| WO | WO 2004108079 | 12/2004 |
| WO | WO 2006084334 | 8/2006 |
| WO | WO 2007047796 A2 * | 4/2007 |
| WO | WO 2009013484 | 1/2009 |

OTHER PUBLICATIONS

Stattin et al., 2010, Am J. Hum. Gen. vol. 86: 126-137.*
Huysamen et al., 2008, J. Biol. Chem. vol. 283: 16693-16701.*
Cambi et al., 2005, Cell. Micro. vol. 7: 481-488.*
Ionescu et al., 2005, J. Pharm Sci. vol. 95: 70-79.*
Gregoriadis, 1994, J. Drug. Targ. vol. 2: 351-356.*
Zelenay et al., 2012, J. Clin. Invest. vol. 122: 1615-27.*
Smeland et al., 1984, CLin. Exp. Immunol. vol. 57: 163-170.*
Lee et al., 2008, Diagnostic Cytopathology, vol. 36, abstract.*
Cox et al., 2004, Exp. Hem. vol. 32: 441-449.*
GenBank Accession No. BC087955, Dec. 22, 2004.
GenBank Accession No. XM_001114857, Jun. 14, 2006.

(Continued)

Primary Examiner — Amy E Juedes
(74) Attorney, Agent, or Firm — Shweta Chandra; Carol L. Francis; Bozicevic, Field & Francis LLP

(57) ABSTRACT

The present invention relates to the identification of proteins located on the cell surface of dendritic cells or precursors thereof, particularly antigen presenting dendritic cells. In particular, the present invention relates to compounds such as antibodies that bind these proteins. These compounds can be used to detect and/or enrich a subset of dendritic cells or precursors thereof. These compounds can also be used to target antigens to dendritic cells or precursors thereof to modulate a humoral and/or T cell mediated immune response to an antigen, or used to target cytotoxic agents to dendritic cells or precursors thereof involved in diseased states.

7 Claims, 16 Drawing Sheets

(56) References Cited

OTHER PUBLICATIONS

Figure 2:
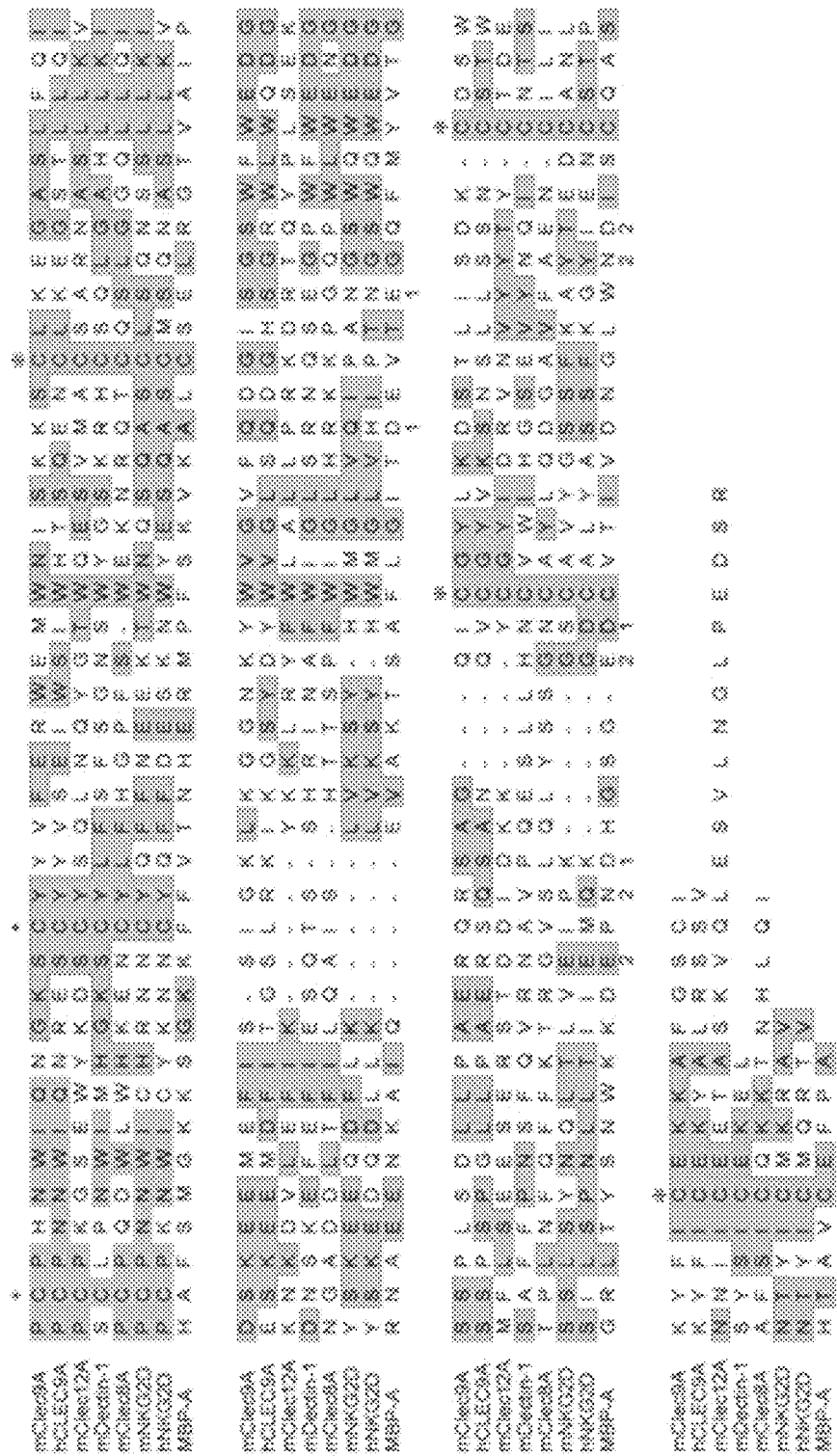

GenBank Accession No. XM_001143778, Sep. 15, 2006.
GenBank Accession No. XM_001493937, Jun. 25, 2007.
GenBank Accession No. XM_849058, Aug. 30, 2005.
GenBank Accession No. XM_868026, Oct. 1, 2005.
GenPept Accession No. AAH87955, Dec. 22, 2004.
GenPept Accession No. NP_997228, Apr. 20, 2004.
GenPept Accession No. XP_001114857, Jun. 14, 2006.
GenPept Accession No. XP_001493987, Jun. 25, 2007.
GenPept Accession No. XP_854151, Aug. 30, 2005.
GenPept Accession No. XP_873119, Oct. 1, 2005.
Belz et al (2004) "Distinct migrating and nonmigrating dendritic cell populations are involved in MHC class I-restricted antigen presentation after lung infection with virus" Proc Natl Acad Sci U S A 101(23):8670-8675.
Bird et al (1988) "Single-Chain Antigen-Binding Proteins" Science 242(4877):423-426.
Bonifaz et al (2002) "Efficient targeting of protein antigen to the dendritic cell receptor DEC-205 in the steady state leads to antigen presentation on major histocompatibility complex class I products and peripheral CD8+ T cell tolerance" J Exp Med 196(12):1627-1638.
Bourque (1995) "Antisense strategies for genetic manipulations in plants" Plant Sci. 105:125-149.
Caminschi et al. (2008) "The dendritic cell subtype-restricted C-type lectin Clec9A is a target for vaccine enhancement" Blood 112(8):3264-3273.
Carter et al (2006) "Preferential induction of CD4+ T cell responses through in vivo targeting of antigen to dendritic cell-associated C-type lectin-1" J Immunol 177(4):2276-2284.
Clark et al. (2003) "The secreted protein discovery initiative (SPDI), a large-scale effort to identify novel human secreted and transmembrane proteins: a bioinformatics assessment" Genome Res 13(10):2265-2270.
Colcher et al (1986) "Use of monoclonal antibodies as radiopharmaceuticals for the localization of human carcinoma xenografts in athymic mice" Methods Enzymol. 121:802-816.
Corbett et al (2005) "Antigen delivery via two molecules on the CD8- dendritic cell subset induces humoral immunity in the absence of conventional 'danger'" Eur J Immunol 35(10):2815-2825.
Demangel et al (2005) "Single chain antibody fragments for the selective targeting of antigens to dendritic cells" Mol Immunol 42(8):979-985.
Den Haan et al (2000) "CD8(+) but not CD8(-) dendritic cells cross-prime cytotoxic T cells in vivo" J Exp Med 192(12):1685-1696.
Drickamer (1999) "C-type lectin-like domains" Cur. Opin Struct Biol 9(5):585-590.
Dudziak et al (2007) "Differential antigen processing by dendritic cell subsets in vivo" Science 315(5808):107-111.
Finkelman et al (1996) "Dendritic cells can present antigen in vivo in a tolerogenic or immunogenic fashion" J Immunol 157(4):1406-1414.
Fuller et al (2007) "The C-type lectin receptors CLEC-2 and Dectin-1, but not DC-SIGN, signal via a novel YXXL-dependent signaling cascade" J Biol Chem 282(17):12397-12409.
Galibert et al (2005) "Nectin-like protein 2 defines a subset of T-cell zone dendritic cells and is a ligand for class-I-restricted T-cell-associated molecule" J Biol Chem 280(23):21955-21964.
Huysamen et al. (2008) "CLEC9A is a novel activation C-type lectin-like receptor expressed on BDCA3+ dendritic cells and a subset of monocytes" J Biol Chem 283(24):16693-16701.
Lahoud et al (2006) "Signal regulatory protein molecules are differentially expressed by CD8- dendritic cells" J Immunol 177(1):372-382.
Naik et al. (2005) "Cutting edge: generation of splenic CD8+ and CD8- dendritic cell equivalents in Fms-like tyrosine kinase 3 ligand bone marrow cultures" J Immunol 174(11):6592-6597.
Naik et al (2006) "Intrasplenic steady-state dendritic cell precursors that are distinct from monocytes" Nat Immunol 7(6):663-671.

Nchinda et al (2008) "The efficacy of DNA vaccination is enhanced in mice by targeting the encoded protein to dendritic cells" J Clin Investig 118(4):1427-1436.
Needleman & Wunsch (1970) "A general method applicable to the search for similarities in the amino acid sequence of two proteins" J. Mol. Biol. 48(3):443-453.
O'Keeffe et al (2002) "Mouse plasmacytoid cells: long-lived cells, heterogeneous in surface phenotype and function, that differentiate into CD8(+) dendritic cells only after microbial stimulus" J Exp Med 196(10):1307-1319.
O'Keeffe et al (2003) "Dendritic cell precursor populations of mouse blood: identification of the murine homologues of human blood plasmacytoid pre-DC2 and CD11c+ DC1 precursors" Blood 101(4):1453-1459.
Park et al. (2004) "Future Directions of Liposome- and Immunoliposome-Based Cancer Therapeutics" *Semin Oncol* 31:196-205.
Pastan et al (1986) "Immunotoxins" Cell 47(5):641-648.
Perriman et al (1992) "Extended target-site specificity for a hammerhead ribozyme" Gene 113:157-16.
Poulin et al. (2010) "Characterization of human DNGR-1+ BDCA3+ leukocytes as putative equivalents of mouse CD8alpha+ dendritic cells" J Exp Med 207(6):1261-1271.
Sancho et al. (2008) "Tumor therapy in mice via antigen targeting to a novel, DC-restricted C-type lectin" J Clin Invest 118(6):2098-2110.
Sancho et al. (2009) "Identification of a dendritic cell receptor that couples sensing of necrosis to immunity" Nature 458 (7240):899-903.
Senior (1998) "Uses of plant gene silencing" Biotech. Genet. Engin. Revs. 15:79-119.
Sun et al (1986) "Chimeric Antibodies with 17-1A-Derived Variable and Human Constant Regions" Hybridoma 5(Suppl. 1)1:517-520.
Van Broekhoven et al (2004) "Targeting dendritic cells with antigen-containing liposomes: a highly effective procedure for induction of antitumor immunity and for tumor immunotherapy" Cancer Res 64(12):4357-4365.
Van De Velde et al (2006) "FcgammaRII and multi-system autoimmune diseas" Springer Semin Immunol 28(4):329-338.
Vandenabeele et al (2001) "Human thymus contains 2 distinct dendritic cell populations" Blood 97(6):1733-1741.
Vremec et al (2000) "CD4 and CD8 expression by dendritic cell subtypes in mouse thymus and spleen" J Immunol 164(6):2978-2986.
Weber (1988) "Primary Structure of a *Plasmodium falciparum* Malaria Antigen Located at the Merozoite Surface and within the Parasitophorous Vacuole" *J Biol Chem* 263(23):11421-11425.
Weis et al (1998) "The C-type lectin superfamily in the immune system" Immunol Rev. 163:19-34.
Belz et al (2005) "CD8alpha+ dendritic cells selectively present MHC class I-restricted noncytolytic viral and intracellular bacterial antigens in vivo" J Immunol 175(1)196-200 (2005).
Binder et al (2004) "The heat-shock protein receptors: some answers and more questions" Tissue Antigens 64(4):442-51 (2004).
Broderick & Winder (2005) "Spectrin, alpha-actinin, and dystrophin" Adv Prot Chem 70:203-246.
Brown et al (1998) "2B4, the natural killer and T cell immunoglobulin superfamily surface protein, is a ligand for CD48" J Exp Med 188(11):2083-90.
Caminschi et al (2001) "Molecular cloning of a C-type lectin superfamily protein differentially expressed by CD8alpha(-31 ) splenic dendritic cells" Mol Immunol 38(5):365-373.
Chakrabati et al. (2006) "Spectrin organization and dynamics: new insights" Biosci Rep 26(6):369-386.
Ciana et al. (2005) "Detergent-resistant membranes in human erythrocytes and their connection to the membrane-skeleton" J Biosci 30(3):317-328.
Delneste (2004) "Scavenger receptors and heat-shock protein-mediated antigen cross-presentation" Biochem Soc Trans 32(Pt. 4):633-635.
Elliot & Ravichandran (2010) "Clearance of apoptotic cells: implications in health and disease" *J Cell Biol* 189(7):1059-1070.

(56) References Cited

OTHER PUBLICATIONS

Grieco et al. (1992) "An improved procedure for the purification of protein fused with glutathione S-transferase" Biotechniques 13(6):856-857.
Henri et al (2001) "The dendritic cell populations of mouse lymph nodes" J Immunol 167(2):741-748.
Hoeffel et al (2007) "Antigen crosspresentation by human plasmacytoid dendritic cells" Immunity 27(3):481-492.
Hume (2008) "Bring out your dead" Nat Immunol 9(1):12-14.
Huysamen & Brown (2009) "The fungal pattern recognition receptor, Dectin-1, and the associated cluster of C-type lectin-like receptors" FEMS Microbiol Lett 290(2):121-128.
Iyoda et al (2002) "The CD8+ dendritic cell subset selectively endocytoses dying cells in culture and in vivo" J Exp Med 195(10):1289-302.
Kenna et al (2008) "Steady-state dendritic cells expressing cognate antigen terminate memory CD8+ T-cell responses" Blood 111(4):2091-100.
Liu et al. (2007) "New insights into the role of the ubiquitin-proteasome pathway in the regulation of apoptosis" Chang Gung Med 30(6):469-479.
Mezger et al. (2008) "Proinflammatory response of immature human dendritic cells is mediated by decetin-1 after exposure to *Aspergilllus fumigatus* germ tubes" J Infect Dis 197(6):924-931.
Moritz & Simpson (1992) "Application of capillary reversed-phase high-performance liquid chromatography to high-sensitivity protein sequence analysis" J Chromatogr 599(1-2):119-130.
Moritz et al (1996) "S-pyridylethylation of intact polyacrylamide gels and in situ digestion of electrophoretically separated proteins: a rapid mass spectrometric method for identifying cysteine-containing peptides" Electrophoresis 17(5):907-917.
Nagata (2007) "Autoimmune diseases caused by defects in clearing dead cells and nuclei expelled from erythroid precursors" Immunol Rev 220:237-50.
Peng et al (2007) "Innate and adaptive immune response to apoptotic cells" J Autoimmun 29(4):303-309.
Plazolles et al. (2011) "Pivotal advance: The promotion of soluble DC-SIGN release by inflammatory signals and its enhancement of cytomegalovirus-mediated cis-infection of myeloid dendritic cells" *J Leuk Biol* 89(3):329-342.
Pyz et al (2008) "Characterisation of murine MICL (CLEC12A) and evidence for an endogenous ligand" Eur J Immunol 38(4):1157-1163.
Sauter et al (2000) "Consequences of cell death: exposure to necrotic tumor cells, but not primary tissue cells or apoptotic cells, induces the maturation of immunostimulatory dendritic cells" J Exp Med 17(3):423-434.
Schulz & Sousa (2002) "Cross-presentation of cell-associated antigens by CD8alpha+ dendritic cells is attributable to their ability to internalize dead cells" Immunology 107(2):183-189.
Simpson et al. (2000) "Proteomic analysis of the human colon carcinoma cell line (LIM 1215): development of a membrane protein database" Electrophoresis 21(9):1707-1732.
Steinman et al. (2000) "The induction of tolerance by dendritic cells that have captured apoptotic cells" J Exp Med 191(3):411-416.
Steinman et al. (2003) "Tolerogenic dendritic cells" Annu Rev Immunol 21:685-711.
Valladangos & Heath (2005) "Life cycle, migration and antigen presenting functions of spleen and lymph node dendritic cells: limitations of the Langerhans cells paradigm" Seminars in Immunology 17(4):262-272.
Van Delft et al. (2006) "The BH3 mimetic ABT-737 targets selective Bcl-2 proteins and efficiently induces apoptosis via Bak/Bax if Mcl-1 is neutralized" Cancer Cell 10(5):389-399.
Wang (2001) "A single amino acid determines lysophospholipid specificity of the S1P1 (EDG1) and LPA1 (EDG2) phospholipid growth factor receptors" *J Biol Chem* 276(52):4921349220.
Whisstock & Lesk (2003) "Prediction of protein function from protein sequence and structure" *Quart Rev Biophy* 36(3):307-340.

Adachi et al (1998) "Targeted disruption of the MyD88 gene results in loss of IL-1- and IL-18-mediated function" Immunity 9(1):143-150.
Caminschi et al (2006) "Gene structure and transcript analysis of the human and mouse EGF-TM7 molecule, FIRE" DNA Seq. 17(1):8-14.
Chothia & Lesk (1987) "Canonical structures for the hypervariable regions of immunoglobulins" J. Mol. Biol. 196(4):901-917.
Dunbrack, et al (1997) "Meeting review: the Second meeting on the Critical Assessment of Techniques for Protein Structure Prediction (CASP2), Asilomar, California, Dec. 13-16, 1996" Fold. Des. 2(2):R27-42.
Greenwood et al (1993) "Structural motifs involved in human IgG antibody effector functions" Eur J Immunol 23(5):1098-1104.
Hochrein et al (2001) "Differential production of IL-12, IFN-alpha, and IFN-gamma by mouse dendritic cell subsets" J Immunol 166(9):5448-5455.
Jones et al (1986) "Replacing the complementarity-determining regions in a human antibody with those from a mouse" Nature 321(6069):522-525.
Morrison et al (1984) "Chimeric human antibody molecules: mouse antigen-binding domains with human constant region domains" Proc Natl Acad Sci USA 81(21):6851-6855.
Pooley et al (2001) "Cutting edge: intravenous soluble antigen is presented to CD4 T cells by CD8− dendritic cells, but cross-presented to CD8 T cells by CD8+ dendritic cells" J Immunol 166(9):5327-5330.
Proietto et al (2004) "Differential production of inflammatory chemokines by murine dendritic cell subsets" Immunobiology 209(1-2):163-172.
Schnorrer et al (2006) "The dominant role of CD8+ dendritic cells in cross-presentation is not dictated by antigen capture" Proc Natl Acad Sci U S A 103(28):10729-10734.
Shortman & Liu (2002) "Mouse and human dendritic cell subtypes" Nat Rev Immunol 2(3):153-161.
Shortman & Naik (2007) "Steady-state and inflammatory dendritic-cell development" Nat Rev Immunol 7(1):19-30.
Smith et al (2003) "Cutting edge: conventional CD8 alpha+ dendritic cells are preferentially involved in CTL priming after footpad infection with herpes simplex virus-1" J Immunol 170(9):4437-4440.
Takeda et al (2003) "Toll-like receptors" Annu Rev Immunol 21:335-376.
Thorpe et al (1987) "New coupling agents for the synthesis of immunotoxins containing a hindered disulfide bond with improved stability in vivo" Cancer Res 47(22):5924-31.
Vitetta et al (1987) "Redesigning nature's poisons to create anti-tumor reagents" Science 238(4830):1098-1104.
Waldmann (1991) "Monoclonal antibodies in diagnosis and therapy" Science 252(5013):1657-1662.
Yamamoto et al (2003) "Role of adaptor TRIF in the MyD88-independent toll-like receptor signaling pathway" Science 301(5633):640-643.
Almeida & Allshire (2005) "RNA silencing and genome regulation" Trends Cell Biol 15(5): 251-258.
Al-Mufti et al (1999) "Investigation of maternal blood enriched for fetal cells: role in screening and diagnosis of fetal trisomies" Am. J. Med. Genet. 85(1):66-75.
Bauer et al (2002) "Paternity testing after pregnancy termination using laser microdissection of chorionic villi" Int J Legal Med 116(1):39-42.
Harayama (1998) "Artificial evolution by DNA shuffling" Trends Biotechnol. 16(2):76-82.
Haseloff & Gerlach (1988) "Simple RNA enzymes with new and highly specific endoribonuclease activities" Nature 334(6183):585-591.
Huston et al (1988) "Protein engineering of antibody binding sites: recovery of specific activity in an anti-digoxin single-chain Fv analogue produced in *Escherichia coli*" Proc Natl Acad Sci USA 85(16):5879-5883.
Leserman (2004) "Liposomes as protein carriers in immunology" J Liposome Res 14(3-4):175-189.

(56) References Cited

OTHER PUBLICATIONS

Millar & Waterhouse (2005) "Plant and animal microRNAs: similarities and differences" Funct Integr Genomics 5(3):129-135.
Miller (1990) "Progress toward human gene therapy" Blood 76(2):271-278.
Pasquinelli et al (2005) "MicroRNAs: a developing story" Curr Opin Genet Develop 15(2):200-205.
Shippy et al (1999) "The hairpin ribozyme. Discovery, mechanism, and development for gene therapy" Mol. Biotech. 12(1):117-129.
Smith et al (2000) "Total silencing by intron-spliced hairpin RNAs" Nature 407(6802):319-320.
Waterhouse et al (1998) "Virus resistance and gene silencing in plants can be induced by simultaneous expression of sense and antisense RNA" Proc. Natl. Acad. Sci. USA 95(23):13959-13964.
Camnschi, et al. "Putative IKDCs are functionally and developmentally similar to natural killer cells, but not to dendritic cells", JEM, vol. 204, No. 11, 2007, pp. 2579-2590.
Sathe, et al. "The Acquisition of Antigen Cross-Presentation Function by Newly Formed Dendritic Cells", The Journal of Immunology, 186:5184-5192, 2011.
Zhang, et al. "The Dendritic Cell Receptor Clec9A Binds Damaged Cells via Exposed Actin Filaments", Cell Press, Immunity 36, pp. 646-657, 2012.

\* cited by examiner

A. Coding sequence of mouse 5B6

ATGCATCGGAAGAAGAAATATAACCTCTTCAGTGGACAATTCCTACCTCAGAGGCCTTCTCAGAAGTGCCAATCCCTAGCAATGTTC
AGGTACATGGTGTGTTGATGAGATTCCTGTGTGCTTGTATGGGCTTGTAGCAAGTCCATTTCTTGGCATCAAGTTCTTC
AGTTATCCTCTCTTGTCTTGGAGCAGAAGACTCATCCAACAGGAAGAGGACACACTTGTCAACCTTACACAGTGCCAGAGGAAATAC
ACACTGGAATACTGCCAAGCCTTACTGCGAGATCCTCCATTCAGCCACAGATGCTTCTTACTGGACCAGTTCTTCTGACCTCTCCACA
GATGGTTCCACAGACCCTGGACAAGAGCAAGGAAACAGTAGTGACGTGCAGCCTGTTGTCCACAACTGGATTCAGAATGGAAAAGTTGTT
ACTAGTTCGTCTTCAACCGTGGAAATGTGGACATCAGTAAGACTAAGACGAGCGAAATATTGGTCTCTTCAAGATGAATCAGTGGATC
GAAGAAATGGAGTTCATCAGCAGATATAGGAAACTCAAAGGGAAACGGAATCAGCGGACATCAGCGGCAGATCGTGGATACCTCA
TTGGTTCGGAAGATGGTCTTCTCCGTCGACTTGTCGAAAGAAGACGATTTATCTGTGAGAAGAAGAGCATTTGATCCTGCATCTGA
AAGATTCTACTCTCATCTCAGATAAGTGCGATAGCTGGAAATATTTTATCTGTGAAATATTTTATCTGTGAGAAGAAGAGCATTTGATCCTGCATCTGA

B. Coding sequence of human 5B6

ATGCCAGGAGAAGAATATACACCTCTCTTCAGTGGACAATAGCCCAGCCACCAGACACTTACCAGACACTGTCTGTCTTCCAACAAATGTTC
AGGACATGCTGTGTCTTGGATGCAGCAGCCGATTCAGCCCGTGATTTCTCCGGGATTAATTAACAGCATCCATTTCCGGGGCTGACTCATGCATAGTTGTTGC
AGTGTCCACCATTGGATGCAGCAGAAGAAACTCAACAAGAGGGCACTGCTAAAACTCATTACAGCAGCCTAAACTATATATATCTCTCCAAGAGAAGAAGCTGT
GCCCTTCAGATGAAATATTGCAAGGCCTTCATGCCAAGCCTTCATTAAGTTCAGCACCACTCTGTCAAACAACCATTGGATTCA
GAACAGAGAAGTTGTTACTAGTGTCCTGGAAATTTGGACATTGGGCACACCAGTCAACACAGAATTGTTTAAGGAAGGTTCCACGTGC
TACAAAATAGAGAGCACAGCCCAAGAAGAAGAAATGATTTTATCACTGCAGTTGCTGAGGAAGAATTAAGGAAGAGCTATGATTACTGGTGTCT
CAGGATGGACACAGCCGACCTGGCTTTGCAAGTGCCTCCCTCCTTTGTCAACTAAGTGGCTCTCTCCTTTGCTCACTAAGTGGCTCTCTCCTTTGTGCACTGTCAGCTAA
CCAAGCTGTGTGGATACGTGGAAAAGCAATTCCTTCCTTCTGCTAACTGCGACGCACGTGGAAGTATTTATCTGCAGAGATCCCAGTCAGCTAA
GATCCTCCTGTCTGA

Figure 1

Figure 1 (con't)

Figure 4:
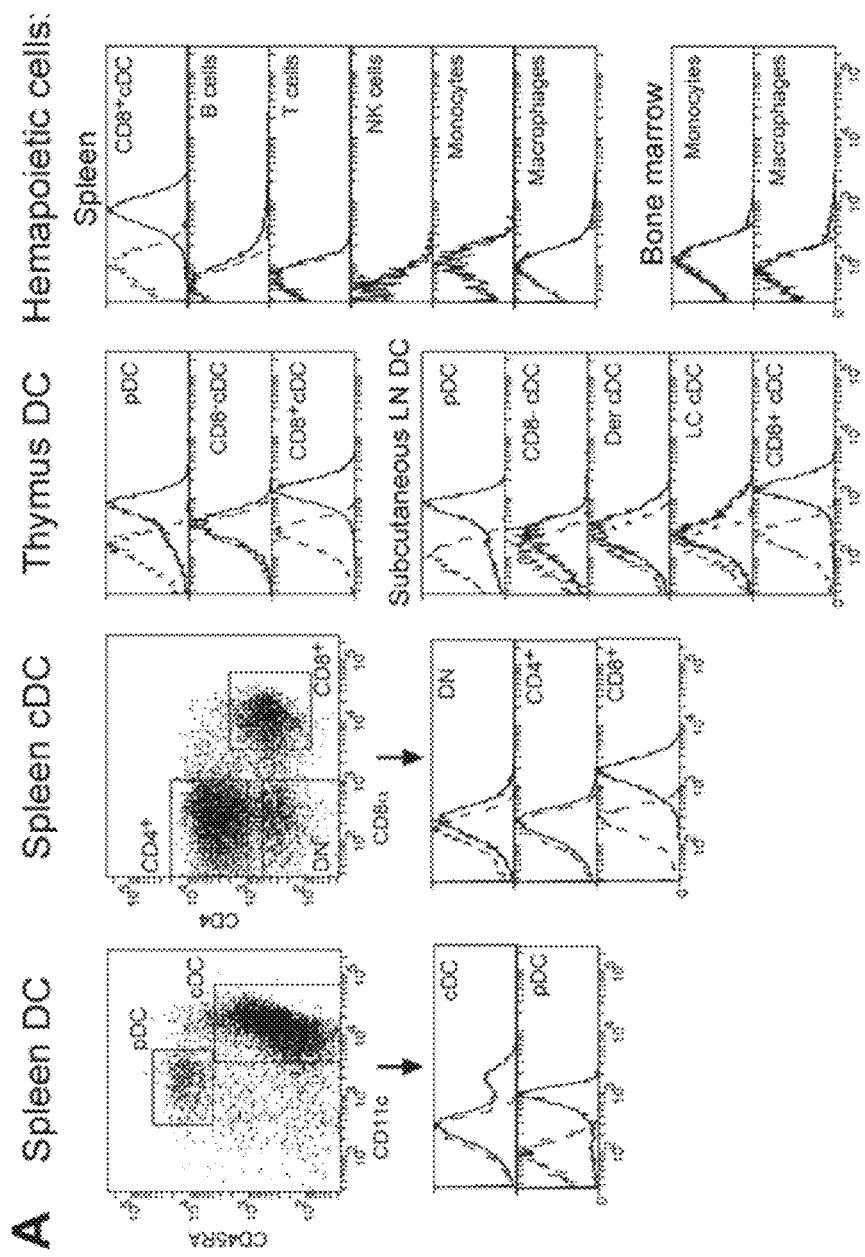

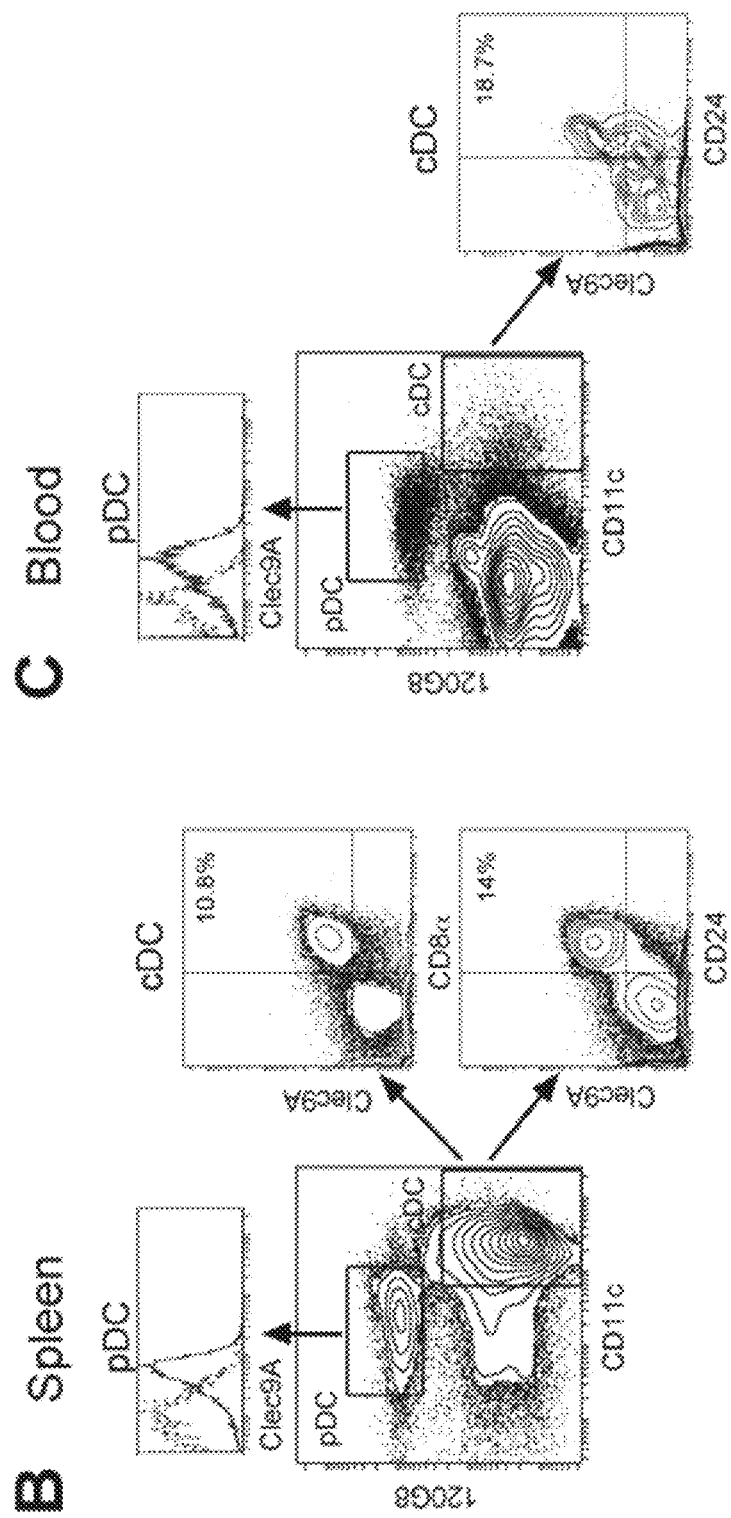
Figure 4 (con't)

Figure 7:
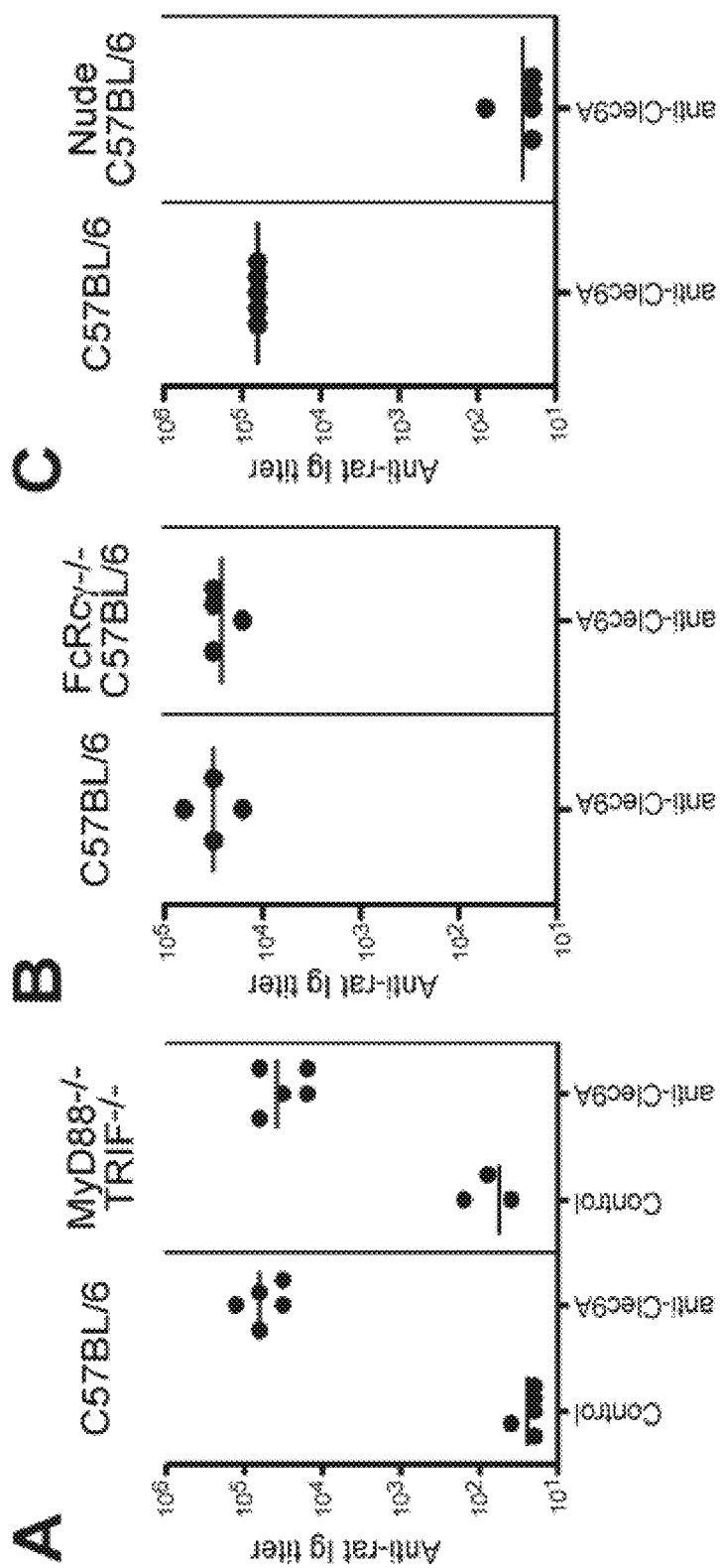

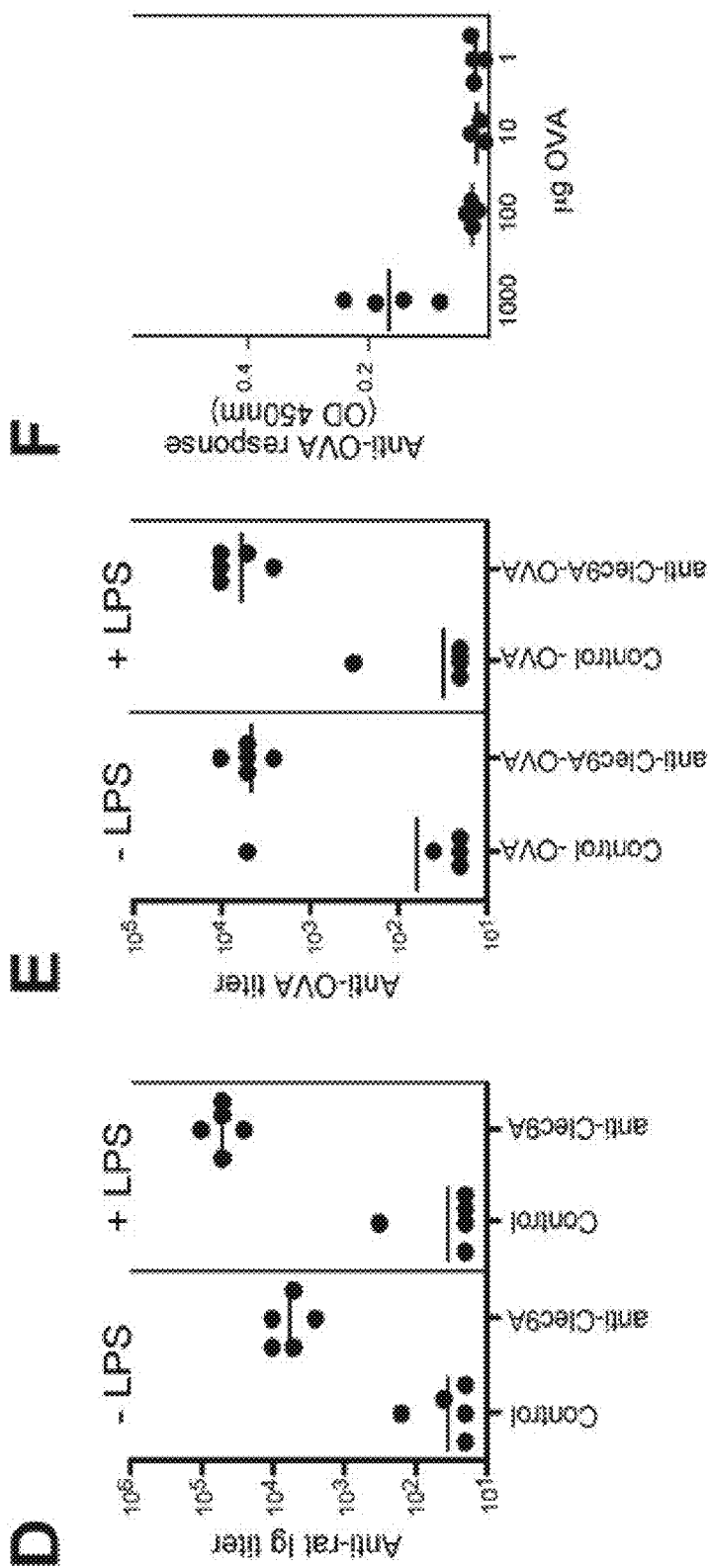
Figure 7 (con't)

A  Mouse 5B6 Soluble Protein-Original (With Stalk)
MVLASSTTSIHTMLLLLLMLFHLGLQASISARQNSGLHHILDAQKMVWNHRGARQDYKDDDDKTR
EQQERLIQQDTALVNLTQWQRKYTLEYCQALLQRSLHSGTDASTGPVLLTSPQMVPQTLDSKETGSDCSPC
PHNWIQNGKSCYYVFERWEMWNISKKSCLKEGASLFQIDSKEEMEFISSIGKLKGGNKYWVGVFQDGISGS
WFWEDGSSPLSDLLPAERQRSAGQICGYLKDSTLISDKCDSWKYFICEKKAFGSCI.

Human 5B6 Soluble Protein-Original (With Stalk)
MVLASSTTSIHTMLLLLLMLFHLGLQASISARQNSGLHHILDAQKMVWNHRGARQDYKDDDDKTR
QQQEKLIQQERALLNFTEWKRSCALQMKYCQAFMQNSLSSAHNSSPCPNNWIQNRESCYYVSEIWSIWHTS
QENCLKEGSTLLQIESKEEMDFITGSLRKIKGSYDYWVGLSQDGHSGRWLWQDGSSPSPGLLPAERSQSAN
QVCGYVKSNSLLSSNCSTWKYFICEKYALRSSV.

Mouse 5B6 Soluble Protein-2/3 (No Stalk)
MVLASSTTSIHTMLLLLLMLFHLGLQASISARQNSGLHHILDAQKMVWNHRGARQDYKDDDDKTR
GSDCSPCPHNWIQNGKSCYYVFERWEMWNISKKSCLKEGASLFQIDSKEEMEFISSIGKLKGGNKYWVGVF
QDGISGSWFWEDGSSPLSDLLPAERQRSAGQICGYLKDSTLISDKCDSWKYFICEKKAFGSCI.

Human 5B6 Soluble Protein-2/3 (No Stalk)
MVLASSTTSIHTMLLLLLMLFHLGLQASISARQNSGLHHILDAQKMVWNHRGARQDYKDDDDKTR
NSSPCPNNWIQNRESCYYVSEIWSIWHTSQENCLKEGSTLLQIESKEEMDFITGSLRKIKGSYDYWVGLSQ
DGHSGRWLWQDGSSPSPGLLPAERSQSANQVCGYVKSNSLLSSNCSTWKYFICEKYALRSSV.

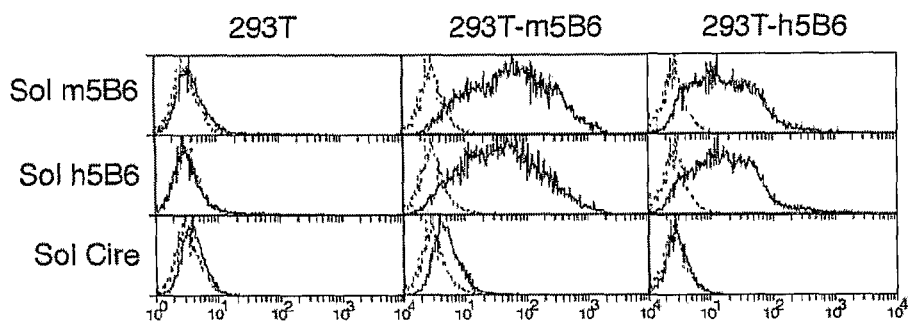

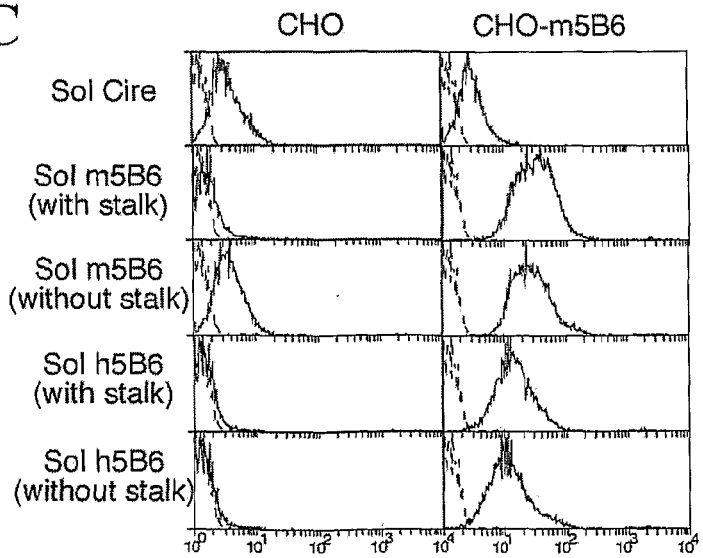

Figure 11

SEQUENCE LISTING

<160> NUMBER OF SEQ ID NOS: 63

<210> SEQ ID NO 1
<211> LENGTH: 241
<212> TYPE: PRT
<213> ORGANISM: Homo sapiens

<400> SEQUENCE: 1

Met His Glu Glu Glu Ile Tyr Thr Ser Leu Gln Trp Asp Ser Pro Ala
1               5                   10                  15

Pro Asp Thr Tyr Gln Lys Cys Leu Ser Ser Asn Lys Cys Ser Gly Ala
            20                  25                  30

Cys Cys Leu Val Met Val Ile Ser Cys Val Phe Cys Met Gly Leu Leu
        35                  40                  45

Thr Ala Ser Ile Phe Leu Gly Val Lys Leu Leu Gln Val Ser Thr Ile
    50                  55                  60

Ala Met Gln Gln Gln Glu Lys Leu Ile Gln Glu Arg Ala Leu Leu
65                  70                  75                  80

Asn Phe Thr Glu Trp Lys Arg Ser Cys Ala Leu Gln Met Lys Tyr Cys
                85                  90                  95

Gln Ala Phe Met Gln Asn Ser Leu Ser Ser Ala His Asn Ser Ser Pro
            100                 105                 110

Cys Pro Asn Asn Trp Ile Gln Asn Arg Glu Ser Cys Tyr Tyr Val Ser
        115                 120                 125

Glu Ile Trp Ser Ile Trp His Thr Ser Gln Glu Asn Cys Leu Lys Glu
    130                 135                 140

Gly Ser Thr Leu Leu Gln Ile Glu Ser Lys Glu Glu Met Asp Phe Ile
145                 150                 155                 160

Thr Gly Ser Leu Arg Lys Ile Lys Gly Ser Tyr Asp Tyr Trp Val Gly
                165                 170                 175

Leu Ser Gln Asp Gly His Ser Gly Arg Trp Leu Trp Gln Asp Gly Ser
            180                 185                 190

Ser Pro Ser Pro Gly Leu Leu Pro Ala Glu Arg Ser Gln Ser Ala Asn
        195                 200                 205

Gln Val Cys Gly Tyr Val Lys Ser Asn Ser Leu Leu Ser Ser Asn Cys
    210                 215                 220

Ser Thr Trp Lys Tyr Phe Ile Cys Glu Lys Tyr Ala Leu Arg Ser Ser
225                 230                 235                 240

Val

<210> SEQ ID NO 2
<211> LENGTH: 265
<212> TYPE: PRT
<213> ORGANISM: Mus musculus

<400> SEQUENCE: 2

Pro Met His Ala Glu Glu Ile Tyr Thr Ser Leu Gln Trp Asp Ile Pro
1               5                   10                  15

Thr Ser Glu Ala Ser Gln Lys Cys Gln Ser Pro Ser Lys Cys Ser Gly
            20                  25                  30

Ala Trp Cys Val Val Thr Met Ile Ser Cys Val Val Cys Met Gly Leu
        35                  40                  45

Leu Ala Thr Ser Ile Phe Leu Gly Ile Lys Phe Phe Gln Val Ser Ser
    50                  55                  60

Leu Val Leu Glu Gln Gln Glu Arg Leu Ile Gln Gln Asp Thr Ala Leu
65                  70                  75                  80

```
Val Asn Leu Thr Gln Trp Gln Arg Lys Tyr Thr Leu Glu Tyr Cys Gln
                85                  90                  95

Ala Leu Leu Gln Arg Ser Leu His Ser Gly Thr Asp Ala Ser Thr Gly
            100                 105                 110

Pro Val Leu Leu Thr Ser Pro Gln Met Val Pro Gln Thr Leu Asp Ser
        115                 120                 125

Lys Glu Thr Gly Ser Asp Cys Ser Pro Cys His Asn Trp Ile Gln
130                 135                 140

Asn Gly Lys Ser Cys Tyr Tyr Val Phe Glu Arg Trp Glu Met Trp Asn
145                 150                 155                 160

Ile Ser Lys Lys Ser Cys Leu Lys Glu Gly Ala Ser Leu Phe Gln Ile
                165                 170                 175

Asp Ser Lys Glu Glu Met Glu Phe Ile Ser Ser Ile Gly Lys Leu Lys
            180                 185                 190

Gly Gly Asn Lys Tyr Trp Val Gly Val Phe Gln Asp Gly Ile Ser Gly
        195                 200                 205

Ser Trp Phe Trp Glu Asp Gly Ser Ser Pro Leu Ser Asp Leu Leu Pro
    210                 215                 220

Ala Glu Arg Gln Arg Ser Ala Gly Gln Ile Cys Gly Tyr Leu Lys Asp
225                 230                 235                 240

Ser Thr Leu Ile Ser Asp Lys Cys Asp Ser Trp Lys Tyr Phe Ile Cys
                245                 250                 255

Glu Lys Lys Ala Phe Gly Ser Cys Ile
            260                 265

<210> SEQ ID NO 3
<211> LENGTH: 241
<212> TYPE: PRT
<213> ORGANISM: Pan troglodytes

<400> SEQUENCE: 3

Met His Glu Glu Glu Ile Tyr Thr Ser Leu Gln Trp Asp Ser Pro Ala
1               5                   10                  15

Pro Asp Thr Tyr Gln Lys Cys Leu Ser Ser Asn Lys Cys Ser Gly Ala
            20                  25                  30

Cys Cys Leu Val Met Val Ile Ser Cys Val Phe Cys Met Gly Leu Leu
        35                  40                  45

Thr Ala Ser Ile Phe Leu Gly Val Lys Leu Leu Gln Val Ser Thr Ile
    50                  55                  60

Ala Met Gln Gln Gln Glu Lys Leu Ile Gln Gln Glu Arg Ala Leu Leu
65                  70                  75                  80

Asn Phe Thr Glu Trp Lys Arg Ser Cys Ala Leu Gln Met Lys Tyr Cys
                85                  90                  95

Gln Ala Phe Met Gln Asn Ser Leu Ser Ser Ala His Asn Ser Ser Pro
            100                 105                 110

Cys Pro Asn Ser Trp Ile Gln Asn Arg Glu Ser Cys Tyr Tyr Val Ser
        115                 120                 125

Glu Ile Trp Ser Ile Trp His Thr Ser Gln Glu Asn Cys Leu Lys Glu
    130                 135                 140

Gly Ser Thr Leu Leu Gln Ile Glu Ser Lys Glu Met Asp Phe Ile
145                 150                 155                 160

Thr Gly Ser Leu Arg Lys Ile Lys Gly Ser Tyr Asp Tyr Trp Val Gly
                165                 170                 175

Leu Ser Gln Asp Gly His Ser Gly Arg Trp Leu Trp Gln Asp Gly Ser
```

180                 185                 190
Ser Pro Ser Pro Gly Leu Leu Pro Val Glu Arg Ser Gln Ser Ala Asn
            195                 200                 205

Gln Val Cys Gly Tyr Met Lys Ser Asn Ser Leu Leu Ser Ser Asn Cys
        210                 215                 220

Ser Thr Trp Lys Tyr Phe Ile Cys Glu Lys Tyr Ala Leu Arg Ser Ser
225                 230                 235                 240

Val

<210> SEQ ID NO 4
<211> LENGTH: 241
<212> TYPE: PRT
<213> ORGANISM: Macaca mulatta

<400> SEQUENCE: 4

Met His Glu Glu Glu Ile Tyr Thr Ser Leu Gln Trp Asp Ser Pro Ala
1               5                   10                  15

Pro Asn Thr Tyr Gln Lys Cys Leu Ser Ser Asn Lys Cys Ser Gly Ala
            20                  25                  30

Trp Cys Leu Val Met Ala Ile Ser Cys Ile Phe Cys Met Gly Leu Leu
        35                  40                  45

Thr Ala Ser Ile Phe Leu Gly Val Lys Leu Leu Gln Val Ser Thr Ile
    50                  55                  60

Ala Met Gln Gln Gln Glu Lys Leu Ile Gln Gln Glu Arg Ala Leu Leu
65                  70                  75                  80

Asn Phe Thr Glu Trp Lys Arg Ser His Val Leu Gln Met Lys Phe Cys
                85                  90                  95

Gln Thr Phe Met Gln Ser Ser Phe Ser Ser Ala His Asn Cys Ser Pro
            100                 105                 110

Cys Pro Asn Asn Trp Ile Gln Asn Arg Glu Ser Cys Tyr Tyr Val Ser
        115                 120                 125

Glu His Trp Lys Ile Trp His Thr Ser Gln Glu Asn Cys Leu Lys Glu
    130                 135                 140

Gly Ser Thr Leu Leu Gln Ile Glu Ser Glu Glu Met Asp Phe Ile
145                 150                 155                 160

Thr Gly Ser Leu Arg Lys Ile Arg Gly Ser Tyr Asp Tyr Trp Val Gly
                165                 170                 175

Leu Ser Gln Asp Gly His Ser Gly Arg Trp Leu Trp Gln Asp Gly Ser
            180                 185                 190

Ser Pro Ser Pro Gly Leu Leu Pro Val Glu Ile Ser Gln Ser Thr Asn
        195                 200                 205

Gln Val Cys Gly Tyr Ile Lys Asn Ser Ser Leu Leu Ser Ser Asn Cys
    210                 215                 220

Ser Thr Trp Lys Tyr Phe Ile Cys Glu Lys Tyr Ala Leu Arg Ser Ser
225                 230                 235                 240

Val

<210> SEQ ID NO 5
<211> LENGTH: 241
<212> TYPE: PRT
<213> ORGANISM: Canis familiaris

<400> SEQUENCE: 5

Met Gln Glu Glu Glu Thr Tyr Thr Thr Ser Leu Arg Trp Asp Ser Pro Thr
1               5                   10                  15

-continued

Pro Ser Phe Tyr Gln Lys His Leu Ser Ser Thr Lys Tyr Ser Gly Ala
                20                  25                  30

Trp Cys Leu Val Thr Val Ile Thr Cys Ile Leu Cys Val Gly Ser Ile
            35                  40                  45

Ala Thr Ser Val Phe Leu Gly Leu Lys Leu Phe Gln Val Ser Thr Ile
 50                  55                  60

Ala Met Lys Gln Arg Glu Lys Leu Ile Leu Gln Asp Arg Ala Leu Leu
 65                  70                  75                  80

Asn Phe Thr Gln Trp Glu Arg Asn His Asn Leu Gln Met Lys Tyr Cys
                85                  90                  95

Gln Thr Leu Met Gln Asn Ser Phe Ser Ser Ala His Asn Cys Ser Pro
            100                 105                 110

Cys Pro Asp Asn Trp Ile Gln Asn Gly Glu Ser Cys Tyr His Val Phe
        115                 120                 125

Glu Asn Trp Lys Ile Trp His Thr Ser Lys Glu Asp Cys Leu Lys Glu
    130                 135                 140

Gly Ser Asn Leu Leu Gln Ile Asp Ser Lys Glu Glu Met Asp Phe Ile
145                 150                 155                 160

Thr Gly Ser Leu Lys Lys Val Lys Ser Gly Phe Asp Tyr Trp Val Gly
                165                 170                 175

Leu Ser Gln Asp Gly Leu Ser Lys Pro Trp Leu Trp Gln Asp Gly Ser
            180                 185                 190

Ser Pro Ser Pro Asp Leu Ser Pro Val Gln Thr Leu Gln Ser Thr Asn
        195                 200                 205

Gln Leu Cys Gly Tyr Leu Lys Asp Lys Phe Leu Ser Ser Ala Asn Cys
    210                 215                 220

Ser Ile Trp Lys Tyr Phe Ile Cys Glu Lys Tyr Ala Leu Arg Ser Ser
225                 230                 235                 240

Asn

<210> SEQ ID NO 6
<211> LENGTH: 241
<212> TYPE: PRT
<213> ORGANISM: Bos taurus

<400> SEQUENCE: 6

Met Gln Glu Asp Glu Ile Tyr Thr Ser Leu Gln Trp Asp Thr Pro Thr
 1               5                  10                  15

Ser Asn Pro Tyr Gln Lys His Leu Ser Ser Thr Lys Asn Ser Gly Val
                20                  25                  30

Trp Cys Leu Val Met Val Ile Leu Cys Ile Phe Cys Ile Gly Ser Leu
            35                  40                  45

Ala Thr Ser Ile Phe Leu Gly Ile Lys Leu Phe Gln Met Ser Thr Thr
 50                  55                  60

Ile Met Lys Gln Gln Glu Lys Leu Ile Gln Gln Glu Arg Ala Leu Leu
 65                  70                  75                  80

Asn Phe Thr Gln Trp Lys Arg Asn Pro Asn Leu Gln Met Thr Tyr Cys
                85                  90                  95

Gln Thr Leu Met Gln Lys Ser Leu Ser Ser Ala Tyr Asn Cys Ser Pro
            100                 105                 110

Cys Pro Asp Asn Trp Ile Gln Asn Gly Glu Ser Cys Tyr His Val Phe
        115                 120                 125

Glu Ser Trp Thr Phe Trp His Thr Ser Arg Lys Asp Cys Trp Lys Lys
    130                 135                 140

```
Gly Ser Asp Leu Leu Gln Ile Glu Ser Lys Glu Met Asp Phe Ile
145                 150                 155                 160

Thr Gly Ser Leu Lys Lys Ile Lys Arg Asn Tyr Asp Tyr Trp Val Gly
                165                 170                 175

Leu Ser Gln Asn Gly Ser Asn Gln Pro Trp Leu Trp Gln Asp Gly Ser
            180                 185                 190

Ser Pro Ser Ala Asp Leu Leu Pro Arg Gln Gly Pro Gln Ser Thr Asn
        195                 200                 205

Gln Val Cys Gly Tyr Leu Arg Asp Asn Asp Leu Ser Ser Ala Asn Cys
    210                 215                 220

Ser Val Trp Lys Tyr Phe Ile Cys Glu Lys Tyr Ala Leu Arg Ser Ser
225                 230                 235                 240

Thr

<210> SEQ ID NO 7
<211> LENGTH: 240
<212> TYPE: PRT
<213> ORGANISM: Equus caballus

<400> SEQUENCE: 7

Met Gln Glu Glu Glu Met Tyr Thr Ser Leu Gln Trp Asp Asn Pro Thr
1               5                   10                  15

Ser Asn Pro Tyr Gln Lys Asn Leu Pro Ser Lys Cys Ser Gly Thr Arg
            20                  25                  30

Cys Leu Val Ile Val Ile Ser Cys Ile Phe Cys Met Gly Leu Leu Thr
        35                  40                  45

Thr Ser Ile Phe Leu Gly Ile Lys Leu Phe Gln Val Ser Ala Ile Ala
    50                  55                  60

Val Lys Gln Gln Glu Lys Leu Ile Gln Gln Glu Arg Thr Leu Leu Asn
65                  70                  75                  80

Phe Thr Gln Cys Asn Arg Asn His Asp Phe Gln Met Lys Cys Cys Gln
                85                  90                  95

Ile Leu Met Lys Asn Ser Leu Asn Ser Ala His His Cys Ser Pro Cys
            100                 105                 110

Pro Asp Asn Trp Ile Gln Asn Gly Glu Ser Cys Tyr Tyr Val Phe Glu
        115                 120                 125

Asn His Lys Thr Trp His Thr Ser Lys Gln Val Cys Leu Lys Glu Gly
    130                 135                 140

Ser Asn Leu Leu Gln Ile Asp Asn Lys Glu Glu Met Asp Phe Ile Thr
145                 150                 155                 160

Gly Ser Leu Lys Arg Ile Lys Ser Ser Tyr Asp Tyr Trp Val Gly Leu
                165                 170                 175

Ser Gln Asp Gly Leu Ser Gly Pro Trp Leu Trp Gln Asp Gly Ser Ser
            180                 185                 190

Leu Ser Pro Asp Leu Trp Pro Val Gln Arg Pro Gln Ser Pro Asn Leu
        195                 200                 205

Val Cys Gly Tyr Leu Lys Asn Lys Ile Leu Phe Ser Ala Asn Cys Ser
    210                 215                 220

Ser Trp Lys His Phe Ile Cys Glu Lys Tyr Ala Leu Arg Ser Cys Ile
225                 230                 235                 240

<210> SEQ ID NO 8
<211> LENGTH: 241
<212> TYPE: PRT
<213> ORGANISM: Rattus norvegicus
```

<400> SEQUENCE: 8

| | | | | | | | | | | | | | | |
|---|---|---|---|---|---|---|---|---|---|---|---|---|---|---|
| Met | His | Glu | Glu | Glu | Ile | Tyr | Thr | Ser | Leu | Gln | Trp | Asp | Ile | Pro | Thr |
| 1 | | | | 5 | | | | | 10 | | | | | 15 | |
| Ser | Glu | Ala | Ser | Gln | Lys | Cys | Pro | Ser | Leu | Ser | Lys | Cys | Pro | Gly | Thr |
| | | | 20 | | | | | 25 | | | | | 30 | | |
| Trp | Cys | Ile | Val | Thr | Val | Ile | Ser | Cys | Val | Val | Cys | Val | Gly | Leu | Leu |
| | | 35 | | | | | 40 | | | | | 45 | | | |
| Ala | Ala | Ser | Ile | Phe | Leu | Gly | Ile | Lys | Phe | Ser | Gln | Val | Ser | Ser | Leu |
| | 50 | | | | | 55 | | | | | 60 | | | | |
| Val | Met | Glu | Gln | Arg | Glu | Arg | Leu | Ile | Arg | Gln | Asp | Thr | Ala | Leu | Leu |
| 65 | | | | | 70 | | | | | 75 | | | | | 80 |
| Asn | Leu | Thr | Glu | Trp | Gln | Arg | Asn | His | Thr | Leu | Gln | Leu | Lys | Ser | Cys |
| | | | | 85 | | | | | 90 | | | | | 95 | |
| Gln | Ala | Ser | Leu | Gln | Arg | Ser | Leu | Arg | Ser | Gly | Ser | Asn | Cys | Asn | Pro |
| | | | 100 | | | | | 105 | | | | | 110 | | |
| Cys | Pro | Pro | Asn | Trp | Ile | Gln | Asn | Gly | Lys | Ser | Cys | Tyr | Tyr | Ala | Phe |
| | | 115 | | | | | 120 | | | | | 125 | | | |
| Asp | Arg | Trp | Glu | Thr | Trp | Asn | Asn | Ser | Lys | Lys | Ser | Cys | Leu | Lys | Glu |
| | 130 | | | | | 135 | | | | | 140 | | | | |
| Gly | Asp | Ser | Leu | Leu | Gln | Ile | Asp | Ser | Lys | Glu | Glu | Met | Glu | Phe | Ile |
| 145 | | | | | 150 | | | | | 155 | | | | | 160 |
| Asn | Leu | Ser | Ile | Trp | Lys | Leu | Lys | Gly | Gly | Tyr | Glu | Tyr | Trp | Val | Gly |
| | | | | 165 | | | | | 170 | | | | | 175 | |
| Val | Phe | Gln | Asp | Gly | Pro | Ser | Gly | Ser | Trp | Phe | Trp | Glu | Asp | Gly | Ser |
| | | | 180 | | | | | 185 | | | | | 190 | | |
| Ser | Pro | Leu | Ser | Asp | Leu | Leu | Pro | Thr | Asp | Arg | Gln | Leu | Ser | Ala | Ser |
| | | 195 | | | | | 200 | | | | | 205 | | | |
| Gln | Ile | Cys | Gly | Tyr | Leu | Lys | Asp | His | Thr | Leu | Ile | Ser | Asp | Asn | Cys |
| | 210 | | | | | 215 | | | | | 220 | | | | |
| Ser | Asn | Trp | Lys | Tyr | Phe | Ile | Cys | Glu | Lys | Lys | Ala | Phe | Gly | Ser | Cys |
| 225 | | | | | 230 | | | | | 235 | | | | | 240 |
| Ile | | | | | | | | | | | | | | | |

<210> SEQ ID NO 9
<211> LENGTH: 726
<212> TYPE: DNA
<213> ORGANISM: Homo sapiens

<400> SEQUENCE: 9

```
atgcacgagg aagaaatata cacctctctt cagtgggata gcccagcacc agacacttac      60
cagaaatgtc tgtcttccaa caaatgttca ggagcatgct gtcttgtgat ggtgatttca     120
tgtgttttct gcatgggatt attaacagca tccatttct tgggcgtcaa gttgttgcag     180
gtgtccacca ttgcgatgca gcagcaagaa aaactcatcc aacaagagag ggcactgcta     240
aactttacag aatggaagag aagctgtgcc cttcagatga atattgcca agccttcatg     300
caaaactcat taagttcagc ccataacagc agtccttgtc aaacaattg gattcagaac     360
agagaaagtt gttactatgt ctctgaaatt tggagcattt ggcacaccag tcaagagaat     420
tgtttaaagg aaggttccac gctgctacaa atagagagca agaagaaat ggattttatc     480
actggcagct tgaggaagat taaggaagc tatgattact gggtggggtt gtctcaggat     540
ggacacagcg acgctggct ttggcaagat ggctcctctc cttctcctgg cctgttgcca     600
gcagagagat cccagtcagc taaccaagtc tgtggatacg tgaaaagcaa ttcccttctt     660
```

```
tcgtctaact gcagcacgtg gaagtatttt atctgtgaga agtatgcgtt gagatcctct    720
gtctga                                                               726
```

```
<210> SEQ ID NO 10
<211> LENGTH: 795
<212> TYPE: DNA
<213> ORGANISM: Mus musculus

<400> SEQUENCE: 10
atgcatgcgg aagaaatata tacctctctt cagtgggaca ttcctacctc agaggcctct     60
cagaagtgcc aatcccctag caaatgttca ggagcatggt gtgttgtgac gatgatttcc    120
tgtgtggtct gtatgggctt gttagcaacg tccattttct gggcatcaa gttcttccag     180 gtatcctctc ttgtcttgga gcagcaggaa agactcatcc aacaggacac agcattggtg    240
aaccttacac agtggcagag gaaatacaca ctggaatact gccaagcctt actgcagaga    300
tctctccatt caggcacaga tgcttctact ggaccagttc ttctgacctc tccacagatg    360
gttccacaga ccctggacag caaggaaaca ggtagtgact gcagcccttg ccacacaac     420 tggattcaga atggaaaaag ttgttactat gtctttgaac ctgggaaat gtggaacatc     480 agtaagaaga gctgttttaaa agagggcgct agtctctttc aaatagacag caaagaagaa    540
atggagttca tcagcagtat agggaaactc aaaggaggaa ataaatattg ggtgggagtg    600
tttcaagatg gaatcagtgg atcttggttc tgggaagatg gctcttctcc ctctctgac     660 ttgttgccag cagaaagaca gcgatcagcc ggccagatct gtggatacct caaagattct    720
actctcatct cagataagtg cgatagctgg aaatatttta tctgtgagaa gaaggcattt    780
ggatcctgca tctga                                                     795
```

```
<210> SEQ ID NO 11
<211> LENGTH: 726
<212> TYPE: DNA
<213> ORGANISM: Pan troglodytes

<400> SEQUENCE: 11
atgcacgagg aagaaatata cacctctctt cagtgggata gcccagcacc agacacttac     60
cagaaatgtc tgtcttccaa caaatgttca ggagcatgct gtcttgtgat ggtgatttca    120
tgtgttttct gcatgggatt attaacagca tccattttct gggcgtcaa gttgttgcag     180 gtgtccacca ttgcgatgca gcagcaagaa aaactcatcc aacaagagag gcactgcta     240 aactttacag aatggaagag aagctgtgcc cttcagatga atattgcca agccttcatg     300 caaaactcat taagttcagc ccataacagc agtccttgtc aaacagttg gattcagaac     360 agagaaagtt gttactatgt ctctgaaatt tggagcattt ggcacaccag tcaagagaat    420
tgtttaaagg aaggttccac gctgctacaa atagagagca agaagaaat ggattttatc     480 actggcagtt tgagaaagat taaaggaagc tatgattact gggtggggtt gtctcaggat    540
ggacacagcg gacgctggct ttggcaagat ggctcctctc cttctcctgg cctgttgcca    600
gtagagagat cccagtcagc taaccaagtc tgtggataca tgaaaagcaa ttcccttctt    660
tcgtctaact gcagcacttg gaagtatttt atctgtgaga agtatgcgtt gagatcctct    720
gtctga                                                               726
```

```
<210> SEQ ID NO 12
<211> LENGTH: 726
<212> TYPE: DNA
<213> ORGANISM: Macaca mulatta
```

<400> SEQUENCE: 12

```
atgcatgagg aagaaatata cacctctctt cagtgggata gtccagcacc aaacacttac      60
cagaaatgtc tgtcttctaa caaatgttca ggagcatggt gtcttgtgat ggcgatttca     120
tgtatttttct gcatggggtt attaacagca tccattttct gggcgtcaa gttgttgcag     180
gtgtccacca ttgcaatgca gcagcaagaa aaactcatcc aacaagagag ggcactgcta     240
aactttacag aatggaagag aagccatgtc cttcagatga aatttttgtca aaccttcatg    300
caaagctctt ttagttcagc ccataactgc agtccttgtc aaacaattg gattcagaac      360
agagaaagct gttactatgt ctctgaacat tggaaaattt ggcacaccag tcaagagaat     420
tgtttaaagg aaggttccac gctgctacaa atagagagcg aagaagaaat ggatttatc      480
actggcagct tgaggaagat tagaggaagc tacgattact gggtgggggtt gtctcaggat    540
ggacacagcg acgctggct ttggcaagat ggctcctctc cttctcctgg cctgttgcca      600
gtagagatat cccagtcaac caaccaagtc tgtggataca tcaaaaacag ttcccttctt    660
tcgtctaact gcagcacttg gaagtatttt atctgcgaga agtatgcatt aagatcctct    720
gtctga                                                                726
```

<210> SEQ ID NO 13
<211> LENGTH: 726
<212> TYPE: DNA
<213> ORGANISM: Canis familiaris

<400> SEQUENCE: 13

```
atgcaggagg aagaaacata cacctctctt cgttgggata gtccaacacc aagcttttac      60
cagaaacacc tatcttccac caaatattca ggagcatggt gtctggtgac ggtgattaca     120
tgtattctct gcgtgggctc aatagcaacc tctgttttct gggcctcaa gttgttccag      180
gtatctacca ttgcaatgaa acagcgagaa aagctcatcc ttcaggacag agcactgttg     240
aatttcacac aatgggagag aaaccataac cttcagatga aatattgcca aaccttgatg    300
caaaactctt tcagttcagc ccacaactgc agcccttgtc ctgacaactg gattcagaat     360
ggagaaagtt gttaccatgt cttttgaaaac tggaaaattt ggcacaccag taaggaggac    420
tgtttgaagg agggctctaa tcttctacaa atagacagca aagaagaaat ggactttatc     480
actggcagcc tgaagaaggt caaaagtggc tttgattact gggtgggact gtctcaagac    540
ggactcagca aaccttggct ttggcaagat ggttcctctc cctcccctga cctgtcgcca    600
gtacagacat tgcaatcaac taaccagctc tgtggatatc taaaggacaa gttccttttct   660
tctgctaact gcagcatttg gaaatatttt atctgtgaga agtatgcatt gagatcctct   720
aactga                                                                726
```

<210> SEQ ID NO 14
<211> LENGTH: 726
<212> TYPE: DNA
<213> ORGANISM: Bos taurus

<400> SEQUENCE: 14

```
atgcaagagg atgaaatata cacctctctt cagtgggata ctccaacatc aaaccccttat    60
cagaaacatc tgtcttctac caaaaattca ggagtatggt gtcttgtgat ggtgatctta    120
tgtatttttct gcattggctc attagcaacc tctattttct gggcatcaa attgtttcag    180
atgtccacta ctataatgaa gcagcaagaa aaactcatcc aacaggagag agcactgctc    240
```

```
aacttcacac agtggaagag aaaccccaac ctacagatga catattgcca aaccttaatg      300
cagaagtctc tcagttcagc ctataactgc agcccttgtc cagacaactg gattcagaat      360
ggagaaagtt gttatcatgt cttttgaaagc tggacattct ggcacactag tagaaaggat     420
tgttggaaga agggctctga tcttctgcaa atagagagca aagaagaaat ggactttatc      480
acgggcagcc tgaagaagat caagagaaac tatgattact gggtaggact gtcacagaat      540
gggtccaacc aaccttggct ttggcaggat ggctcctctc cttctgctga cctgttgcca      600
agacagggac cccagtcaac aaatcaggtc tgtggatacc tcagagacaa cgacctttct      660
tctgctaact gcagcgtttg gaaatatttc atctgtgaga agtacgcact aagatcttct      720
acctga                                                                726
```

<210> SEQ ID NO 15
<211> LENGTH: 723
<212> TYPE: DNA
<213> ORGANISM: Equus caballus
<400> SEQUENCE: 15

```
atgcaggagg aagaaatgta cacctctctc caatgggata acccaacatc aaacccttac       60
cagaaaaatc tgccttccaa atgttcagga acacggtgtc ttgtgatagt gatttcatgt      120
attttctgca tgggcttgtt aacaacgtcc attttcttgg gcatcaagtt gttccaggtg      180
tctgctattg cagtgaagca gcaagaaaaa ctcatccaac aggagagaac actgttgaac      240
ttcacacagt gtaatagaaa ccatgacttc cagatgaaat gctgtcaaat cctcatgaaa      300
aactcattaa attcagccca tcactgcagc ccttgtccag acaactggat tcagaatgga      360
gaaagttgtt actatgtctt tgaaaatcac aaaacttggc ataccagtaa acaggtttgt      420
ttgaaggagg gctctaatct tctacaaata gacaacaaag aagaaatgga ctttatcaca      480
ggcagcctga gaggatcaa agcagctat gattactggg tggactgtc tcaggacgga        540 ctcagcggac cttggctttg gcaagatggt tcttctcttt ccccagacct gtggccagta      600
cagagaccgc aatcacctaa cctggtctgt ggatacctca aaaacaagat cctttttttca     660 gctaactgca gcagttggaa acattttatc tgtgagaagt atgcattaag atcttgcatc     720
tga                                                                    723
```

<210> SEQ ID NO 16
<211> LENGTH: 726
<212> TYPE: DNA
<213> ORGANISM: Rattus norvegicus
<400> SEQUENCE: 16

```
atgcatgagg aagaaatata cacctctctt cagtgggaca ttccaacctc agaggcctct       60
cagaagtgtc catcccttag caaatgtcca ggaacatggt gtattgtgac ggtgatttcc      120
tgtgtggtct gtgtgggctt actagcagca tccatttttct tggcatcaa gttctcccag      180 gtgtcctctc ttgtaatgga gcagcgggaa aggctcatcc acaggacac agcattgctg       240 aacctcacag agtggcagag gaaccataca ctgcagttaa aaagctgcca agcctcacta      300
caaagatctc tccgttcagg cagtaactgc aaccctgtc accgaactg gattcagaat        360 ggaaaaagtt gttactatgc ctttgaccgc tgggaaacgt ggaacaacag taagaagagt      420
tgttaaaaag agggcgatag tctccttcaa atagacagca aagaagaaat ggagtttatc      480
aacctcagta tatggaagct caaaggagga tatgaatact gggtgggagt gtttcaagat      540
ggacccagtg gatcttggtt ttgggaagat ggctcttctc ctctctctga cttgttgcca     600
```

-continued

```
acagacagac agctatcagc cagccagatc tgtggatacc tcaaagacca tactctcatc    660
tcggataact gcagtaactg gaaatatttt atctgtgaga agaaggcatt tggatcctgc    720
atctga                                                               726
```

```
<210> SEQ ID NO 17
<211> LENGTH: 22
<212> TYPE: DNA
<213> ORGANISM: Artificial Sequence
<220> FEATURE:
<223> OTHER INFORMATION: Synthetic primer

<400> SEQUENCE: 17
tgtgactgct cccacaactg ga                                              22
```

```
<210> SEQ ID NO 18
<211> LENGTH: 22
<212> TYPE: DNA
<213> ORGANISM: Artificial Sequence
<220> FEATURE:
<223> OTHER INFORMATION: Synthetic primer

<400> SEQUENCE: 18
tttgcaccaa tcacagcaca ga                                              22
```

```
<210> SEQ ID NO 19
<211> LENGTH: 22
<212> TYPE: DNA
<213> ORGANISM: Artificial Sequence
<220> FEATURE:
<223> OTHER INFORMATION: Synthetic primer

<400> SEQUENCE: 19
catttgcagt ggcaaagtgg ag                                              22
```

```
<210> SEQ ID NO 20
<211> LENGTH: 22
<212> TYPE: DNA
<213> ORGANISM: Artificial Sequence
<220> FEATURE:
<223> OTHER INFORMATION: Synthetic primer

<400> SEQUENCE: 20
gtctcgctcc tggaagatgg tg                                              22
```

```
<210> SEQ ID NO 21
<211> LENGTH: 26
<212> TYPE: DNA
<213> ORGANISM: Artificial Sequence
<220> FEATURE:
<223> OTHER INFORMATION: Synthetic primer

<400> SEQUENCE: 21
gccatttctt gtaccaacct actcct                                          26
```

```
<210> SEQ ID NO 22
<211> LENGTH: 23
<212> TYPE: DNA
<213> ORGANISM: Artificial Sequence
<220> FEATURE:
<223> OTHER INFORMATION: Synthetic primer

<400> SEQUENCE: 22
cggtgtggta tggatcgtca ctt                                             23
```

```
<210> SEQ ID NO 23
<211> LENGTH: 22
<212> TYPE: DNA
<213> ORGANISM: Artificial Sequence
<220> FEATURE:
<223> OTHER INFORMATION: Synthetic primer

<400> SEQUENCE: 23
agcctcctgt gtggactgct tt                                              22

<210> SEQ ID NO 24
<211> LENGTH: 22
<212> TYPE: DNA
<213> ORGANISM: Artificial Sequence
<220> FEATURE:
<223> OTHER INFORMATION: Synthetic primer

<400> SEQUENCE: 24
ttcatggccc acattttggt tt                                              22

<210> SEQ ID NO 25
<211> LENGTH: 33
<212> TYPE: DNA
<213> ORGANISM: Artificial Sequence
<220> FEATURE:
<223> OTHER INFORMATION: Synthetic primer

<400> SEQUENCE: 25
tagtagacgc gtgagcagca ggaaagactc atc                                  33

<210> SEQ ID NO 26
<211> LENGTH: 33
<212> TYPE: DNA
<213> ORGANISM: Artificial Sequence
<220> FEATURE:
<223> OTHER INFORMATION: Synthetic primer

<400> SEQUENCE: 26
tagtagacgc gttcagatgc aggatccaaa tgc                                  33

<210> SEQ ID NO 27
<211> LENGTH: 33
<212> TYPE: DNA
<213> ORGANISM: Artificial Sequence
<220> FEATURE:
<223> OTHER INFORMATION: Synthetic primer

<400> SEQUENCE: 27
tagtagacgc gtcagcagca agaaaaactc atc                                  33

<210> SEQ ID NO 28
<211> LENGTH: 33
<212> TYPE: DNA
<213> ORGANISM: Artificial Sequence
<220> FEATURE:
<223> OTHER INFORMATION: Synthetic primer

<400> SEQUENCE: 28
tagtagacgc gttcagacag aggatctcaa cgc                                  33

<210> SEQ ID NO 29
<211> LENGTH: 22
<212> TYPE: PRT
<213> ORGANISM: Artificial Sequence
<220> FEATURE:
<223> OTHER INFORMATION: Antigenic fragment of murine 5B6
```

<400> SEQUENCE: 29

Asp Gly Ser Ser Pro Leu Ser Asp Leu Leu Pro Ala Glu Arg Gln Arg
1               5                   10                  15

Ser Ala Gly Gln Ile Cys
            20

<210> SEQ ID NO 30
<211> LENGTH: 27
<212> TYPE: PRT
<213> ORGANISM: Artificial Sequence
<220> FEATURE:
<223> OTHER INFORMATION: Antigenic fragment of murine 5B6

<400> SEQUENCE: 30

Arg Trp Leu Trp Gln Asp Gly Ser Ser Pro Ser Pro Gly Leu Leu Pro
1               5                   10                  15

Ala Glu Arg Ser Gln Ser Ala Asn Gln Val Cys
            20                  25

<210> SEQ ID NO 31
<211> LENGTH: 18
<212> TYPE: PRT
<213> ORGANISM: Artificial Sequence
<220> FEATURE:
<223> OTHER INFORMATION: Biotinylation consensus sequence

<400> SEQUENCE: 31

Asn Ser Gly Leu His His Ile Leu Asp Ala Gln Lys Met Val Trp Asn
1               5                   10                  15

His Arg

<210> SEQ ID NO 32
<211> LENGTH: 136
<212> TYPE: PRT
<213> ORGANISM: Mus musculus

<400> SEQUENCE: 32

Pro Cys Pro Lys Gly Ser Glu Trp Tyr Lys Asp Ser Cys Tyr Ser Gln
1               5                   10                  15

Leu Asn Gln Tyr Gly Thr Trp Gln Glu Ser Val Met Ala Cys Ser Ala
            20                  25                  30

Arg Asn Ala Ser Leu Leu Lys Val Lys Asn Lys Asp Val Leu Glu Phe
        35                  40                  45

Ile Lys Tyr Lys Lys Leu Arg Tyr Phe Trp Leu Ala Leu Leu Pro Arg
    50                  55                  60

Lys Asp Arg Thr Gln Tyr Pro Leu Ser Glu Lys Met Phe Leu Ser Glu
65                  70                  75                  80

Glu Ser Glu Arg Ser Thr Asp Asp Ile Asp Lys Lys Tyr Cys Gly Tyr
                85                  90                  95

Ile Asp Arg Val Asn Val Tyr Tyr Thr Tyr Cys Thr Glu Asn Asn
            100                 105                 110

Ile Ile Cys Glu Glu Thr Ala Ser Lys Val Gln Leu Glu Ser Val Leu
        115                 120                 125

Asn Gly Leu Pro Glu Asp Ser Arg
    130                 135

<210> SEQ ID NO 33
<211> LENGTH: 127
<212> TYPE: PRT

```
<213> ORGANISM: Mus musculus

<400> SEQUENCE: 33

Ser Cys Leu Pro Asn Trp Ile Met His Gly Lys Ser Cys Tyr Leu Phe
1               5                   10                  15

Ser Phe Ser Gly Asn Ser Trp Tyr Gly Ser Lys Arg His Cys Ser Gln
            20                  25                  30

Leu Gly Ala His Leu Leu Lys Ile Asp Asn Ser Lys Glu Phe Glu Phe
        35                  40                  45

Ile Glu Ser Gln Thr Ser Ser His Arg Ile Asn Ala Phe Trp Ile Gly
50                  55                  60

Leu Ser Arg Asn Gln Ser Glu Gly Pro Trp Phe Trp Glu Asp Gly Ser
65                  70                  75                  80

Ala Phe Phe Pro Asn Ser Phe Gln Val Arg Asn Thr Val Pro Gln Glu
                85                  90                  95

Ser Leu Leu His Asn Cys Val Trp Ile His Gly Ser Glu Val Tyr Asn
            100                 105                 110

Gln Ile Cys Asn Thr Ser Ser Tyr Ser Ile Cys Glu Lys Glu Leu
        115                 120                 125

<210> SEQ ID NO 34
<211> LENGTH: 130
<212> TYPE: PRT
<213> ORGANISM: Mus musculus

<400> SEQUENCE: 34

Pro Cys Pro Gln Asp Trp Leu Trp His Lys Glu Asn Cys Tyr Leu Phe
1               5                   10                  15

His Gly Pro Phe Ser Trp Glu Lys Asn Arg Gln Thr Cys Gln Ser Leu
            20                  25                  30

Gly Gly Gln Leu Leu Gln Ile Asn Gly Ala Asp Asp Leu Thr Phe Ile
        35                  40                  45

Leu Gln Ala Ile Ser His Thr Thr Ser Pro Phe Trp Ile Gly Leu His
50                  55                  60

Arg Lys Lys Pro Gly Gln Pro Trp Leu Trp Glu Asn Gly Thr Arg Leu
65                  70                  75                  80

Asn Phe Gln Phe Phe Lys Thr Arg Gly Val Ser Leu Gln Leu Tyr Ser
                85                  90                  95

Ser Gly Asn Cys Ala Tyr Leu Gln Asp Gly Ala Val Phe Ala Glu Asn
            100                 105                 110

Cys Ile Leu Ile Ala Phe Ser Ile Cys Gln Lys Lys Thr Asn His Leu
        115                 120                 125

Gln Ile
    130

<210> SEQ ID NO 35
<211> LENGTH: 119
<212> TYPE: PRT
<213> ORGANISM: Mus musculus

<400> SEQUENCE: 35

Pro Cys Pro Asn Asn Trp Ile Cys His Arg Asn Asn Cys Tyr Gln Phe
1               5                   10                  15

Phe Asn Glu Glu Lys Thr Trp Asn Gln Ser Gln Ala Ser Cys Leu Ser
            20                  25                  30

Gln Asn Ser Ser Leu Leu Lys Ile Tyr Ser Lys Glu Gly Gln Asp Phe
        35                  40                  45
```

```
Leu Lys Leu Val Lys Ser Tyr His Trp Met Gly Leu Val Gln Ile Pro
        50                  55                  60

Ala Asn Gly Ser Trp Gln Trp Glu Asp Gly Ser Ser Leu Ser Tyr Asn
 65                  70                  75                  80

Gln Leu Thr Leu Val Glu Ile Pro Lys Gly Ser Cys Ala Val Tyr Gly
                 85                  90                  95

Ser Ser Phe Lys Ala Tyr Thr Glu Asp Cys Ala Asn Leu Asn Thr Tyr
            100                 105                 110

Ile Cys Met Lys Arg Ala Val
            115
```

<210> SEQ ID NO 36
<211> LENGTH: 119
<212> TYPE: PRT
<213> ORGANISM: Homo sapiens

<400> SEQUENCE: 36

```
Pro Cys Pro Lys Asn Trp Ile Cys Tyr Lys Asn Asn Cys Tyr Gln Phe
 1               5                  10                  15

Phe Asp Glu Ser Lys Asn Trp Tyr Glu Ser Gln Ala Ser Cys Met Ser
                 20                  25                  30

Gln Asn Ala Ser Leu Leu Lys Val Tyr Ser Lys Glu Asp Gln Asp Leu
             35                  40                  45

Leu Lys Leu Val Lys Ser Tyr His Trp Met Gly Leu Val His Ile Pro
        50                  55                  60

Thr Asn Gly Ser Trp Gln Trp Glu Asp Gly Ser Ile Leu Ser Pro Asn
 65                  70                  75                  80

Leu Leu Thr Ile Ile Glu Met Gln Lys Gly Asp Cys Ala Leu Tyr Ala
                 85                  90                  95

Ser Ser Phe Lys Gly Tyr Ile Glu Asn Cys Ser Thr Pro Asn Thr Tyr
            100                 105                 110

Ile Cys Met Gln Arg Thr Val
            115
```

<210> SEQ ID NO 37
<211> LENGTH: 123
<212> TYPE: PRT
<213> ORGANISM: Rattus norvegicus

<400> SEQUENCE: 37

```
His Ala Phe Ser Met Gly Lys Lys Ser Gly Lys Lys Phe Phe Val Thr
 1               5                  10                  15

Asn His Glu Arg Met Pro Phe Ser Lys Val Lys Ala Leu Cys Ser Glu
                 20                  25                  30

Leu Arg Gly Thr Val Ala Ile Pro Arg Asn Ala Glu Glu Asn Lys Ala
             35                  40                  45

Ile Gln Glu Val Ala Lys Thr Ser Ala Phe Leu Gly Ile Thr Asp Glu
        50                  55                  60

Val Thr Glu Gly Gln Phe Met Tyr Val Thr Gly Gly Arg Leu Thr Tyr
 65                  70                  75                  80

Ser Asn Trp Lys Lys Asp Glu Pro Asn Asp His Gly Ser Gly Glu Asp
                 85                  90                  95

Cys Val Thr Ile Val Asp Asn Gly Leu Trp Asn Asp Ile Ser Cys Gln
            100                 105                 110

Ala Ser His Thr Ala Val Cys Glu Phe Pro Ala
            115                 120
```

```
<210> SEQ ID NO 38
<211> LENGTH: 263
<212> TYPE: PRT
<213> ORGANISM: Artificial Sequence
<220> FEATURE:
<223> OTHER INFORMATION: Soluble flag tagged mouse 5B6 including stalk

<400> SEQUENCE: 38
```

| Met | Val | Leu | Ala | Ser | Ser | Thr | Thr | Ser | Ile | His | Thr | Met | Leu | Leu | Leu |
|---|---|---|---|---|---|---|---|---|---|---|---|---|---|---|---|
| 1 | | | | 5 | | | | | 10 | | | | | 15 | |

| Leu | Leu | Met | Leu | Phe | His | Leu | Gly | Leu | Gln | Ala | Ser | Ile | Ser | Ala | Arg |
|---|---|---|---|---|---|---|---|---|---|---|---|---|---|---|---|
| | | | 20 | | | | | 25 | | | | | 30 | | |

| Gln | Asn | Ser | Gly | Leu | His | His | Ile | Leu | Asp | Ala | Gln | Lys | Met | Val | Trp |
|---|---|---|---|---|---|---|---|---|---|---|---|---|---|---|---|
| | | | 35 | | | | | 40 | | | | | 45 | | |

| Asn | His | Arg | Gly | Ala | Arg | Gln | Asp | Tyr | Lys | Asp | Asp | Asp | Lys | Thr |
|---|---|---|---|---|---|---|---|---|---|---|---|---|---|---|
| | 50 | | | | | 55 | | | | | 60 | | | |

| Arg | Glu | Gln | Gln | Glu | Arg | Leu | Ile | Gln | Gln | Asp | Thr | Ala | Leu | Val | Asn |
|---|---|---|---|---|---|---|---|---|---|---|---|---|---|---|---|
| 65 | | | | | 70 | | | | | 75 | | | | | 80 |

| Leu | Thr | Gln | Trp | Gln | Arg | Lys | Tyr | Thr | Leu | Glu | Tyr | Cys | Gln | Ala | Leu |
|---|---|---|---|---|---|---|---|---|---|---|---|---|---|---|---|
| | | | | 85 | | | | | 90 | | | | | 95 | |

| Leu | Gln | Arg | Ser | Leu | His | Ser | Gly | Thr | Asp | Ala | Ser | Thr | Gly | Pro | Val |
|---|---|---|---|---|---|---|---|---|---|---|---|---|---|---|---|
| | | | | 100 | | | | | 105 | | | | | 110 | |

| Leu | Leu | Thr | Ser | Pro | Gln | Met | Val | Pro | Gln | Thr | Leu | Asp | Ser | Lys | Glu |
|---|---|---|---|---|---|---|---|---|---|---|---|---|---|---|---|
| | | | 115 | | | | | 120 | | | | | 125 | | |

| Thr | Gly | Ser | Asp | Cys | Ser | Pro | Cys | Pro | His | Asn | Trp | Ile | Gln | Asn | Gly |
|---|---|---|---|---|---|---|---|---|---|---|---|---|---|---|---|
| | 130 | | | | | 135 | | | | | 140 | | | | |

| Lys | Ser | Cys | Tyr | Tyr | Val | Phe | Glu | Arg | Trp | Glu | Met | Trp | Asn | Ile | Ser |
|---|---|---|---|---|---|---|---|---|---|---|---|---|---|---|---|
| 145 | | | | | 150 | | | | | 155 | | | | | 160 |

| Lys | Lys | Ser | Cys | Leu | Lys | Glu | Gly | Ala | Ser | Leu | Phe | Gln | Ile | Asp | Ser |
|---|---|---|---|---|---|---|---|---|---|---|---|---|---|---|---|
| | | | | 165 | | | | | 170 | | | | | 175 | |

| Lys | Glu | Glu | Met | Glu | Phe | Ile | Ser | Ser | Ile | Gly | Lys | Leu | Lys | Gly | Gly |
|---|---|---|---|---|---|---|---|---|---|---|---|---|---|---|---|
| | | | | 180 | | | | | 185 | | | | | 190 | |

| Asn | Lys | Tyr | Trp | Val | Gly | Val | Phe | Gln | Asp | Gly | Ile | Ser | Gly | Ser | Trp |
|---|---|---|---|---|---|---|---|---|---|---|---|---|---|---|---|
| | | | 195 | | | | | 200 | | | | | 205 | | |

| Phe | Trp | Glu | Asp | Gly | Ser | Ser | Pro | Leu | Ser | Asp | Leu | Leu | Pro | Ala | Glu |
|---|---|---|---|---|---|---|---|---|---|---|---|---|---|---|---|
| | 210 | | | | | 215 | | | | | 220 | | | | |

| Arg | Gln | Arg | Ser | Ala | Gly | Gln | Ile | Cys | Gly | Tyr | Leu | Lys | Asp | Ser | Thr |
|---|---|---|---|---|---|---|---|---|---|---|---|---|---|---|---|
| 225 | | | | | 230 | | | | | 235 | | | | | 240 |

| Leu | Ile | Ser | Asp | Lys | Cys | Asp | Ser | Trp | Lys | Tyr | Phe | Ile | Cys | Glu | Lys |
|---|---|---|---|---|---|---|---|---|---|---|---|---|---|---|---|
| | | | | 245 | | | | | 250 | | | | | 255 | |

| Lys | Ala | Phe | Gly | Ser | Cys | Ile |
|---|---|---|---|---|---|---|
| | | | 260 | | | |

```
<210> SEQ ID NO 39
<211> LENGTH: 240
<212> TYPE: PRT
<213> ORGANISM: Artificial Sequence
<220> FEATURE:
<223> OTHER INFORMATION: Soluble flag tagged human 5B6 including stalk

<400> SEQUENCE: 39
```

| Met | Val | Leu | Ala | Ser | Ser | Thr | Thr | Ser | Ile | His | Thr | Met | Leu | Leu | Leu |
|---|---|---|---|---|---|---|---|---|---|---|---|---|---|---|---|
| 1 | | | | 5 | | | | | 10 | | | | | 15 | |

| Leu | Leu | Met | Leu | Phe | His | Leu | Gly | Leu | Gln | Ala | Ser | Ile | Ser | Ala | Arg |
|---|---|---|---|---|---|---|---|---|---|---|---|---|---|---|---|
| | | | 20 | | | | | 25 | | | | | 30 | | |

| Gln | Asn | Ser | Gly | Leu | His | His | Ile | Leu | Asp | Ala | Gln | Lys | Met | Val | Trp |
|---|---|---|---|---|---|---|---|---|---|---|---|---|---|---|---|

```
            35                  40                  45
Asn His Arg Gly Ala Arg Gln Asp Tyr Lys Asp Asp Asp Lys Thr
 50                  55                  60

Arg Gln Gln Gln Glu Lys Leu Ile Gln Gln Glu Arg Ala Leu Leu Asn
 65                  70                  75                  80

Phe Thr Glu Trp Lys Arg Ser Cys Ala Leu Gln Met Lys Tyr Cys Gln
                 85                  90                  95

Ala Phe Met Gln Asn Ser Leu Ser Ser Ala His Asn Ser Ser Pro Cys
            100                 105                 110

Pro Asn Asn Trp Ile Gln Asn Arg Glu Ser Cys Tyr Tyr Val Ser Glu
        115                 120                 125

Ile Trp Ser Ile Trp His Thr Ser Gln Glu Asn Cys Leu Lys Glu Gly
    130                 135                 140

Ser Thr Leu Leu Gln Ile Glu Ser Lys Glu Met Asp Phe Ile Thr
145                 150                 155                 160

Gly Ser Leu Arg Lys Ile Lys Gly Ser Tyr Asp Tyr Trp Val Gly Leu
                165                 170                 175

Ser Gln Asp Gly His Ser Gly Arg Trp Leu Trp Gln Asp Gly Ser Ser
            180                 185                 190

Pro Ser Pro Gly Leu Leu Pro Ala Glu Arg Ser Gln Ser Ala Asn Gln
        195                 200                 205

Val Cys Gly Tyr Val Lys Ser Asn Ser Leu Leu Ser Ser Asn Cys Ser
    210                 215                 220

Thr Trp Lys Tyr Phe Ile Cys Glu Lys Tyr Ala Leu Arg Ser Ser Val
225                 230                 235                 240

<210> SEQ ID NO 40
<211> LENGTH: 199
<212> TYPE: PRT
<213> ORGANISM: Artificial Sequence
<220> FEATURE:
<223> OTHER INFORMATION: Soluble flag tagged mouse 5B6 without stalk

<400> SEQUENCE: 40

Met Val Leu Ala Ser Ser Thr Thr Ser Ile His Thr Met Leu Leu Leu
 1               5                  10                  15

Leu Leu Met Leu Phe His Leu Gly Leu Gln Ala Ser Ile Ser Ala Arg
                20                  25                  30

Gln Asn Ser Gly Leu His His Ile Leu Asp Ala Gln Lys Met Val Trp
            35                  40                  45

Asn His Arg Gly Ala Arg Gln Asp Tyr Lys Asp Asp Asp Lys Thr
 50                  55                  60

Arg Gly Ser Asp Cys Ser Pro Cys Pro His Asn Trp Ile Gln Asn Gly
 65                  70                  75                  80

Lys Ser Cys Tyr Tyr Val Phe Glu Arg Trp Glu Met Trp Asn Ile Ser
                 85                  90                  95

Lys Lys Ser Cys Leu Lys Glu Gly Ala Ser Leu Phe Gln Ile Asp Ser
            100                 105                 110

Lys Glu Glu Met Glu Phe Ile Ser Ser Ile Gly Lys Leu Lys Gly Gly
        115                 120                 125

Asn Lys Tyr Trp Val Gly Val Phe Gln Asp Gly Ile Ser Gly Ser Trp
    130                 135                 140

Phe Trp Glu Asp Gly Ser Ser Pro Leu Ser Asp Leu Leu Pro Ala Glu
145                 150                 155                 160

Arg Gln Arg Ser Ala Gly Gln Ile Cys Gly Tyr Leu Lys Asp Ser Thr
```

165                 170                 175

Leu Ile Ser Asp Lys Cys Asp Ser Trp Lys Tyr Phe Ile Cys Glu Lys
            180                 185                 190

Lys Ala Phe Gly Ser Cys Ile
        195

<210> SEQ ID NO 41
<211> LENGTH: 198
<212> TYPE: PRT
<213> ORGANISM: Artificial Sequence
<220> FEATURE:
<223> OTHER INFORMATION: Soluble flag tagged human 5B6 without stalk

<400> SEQUENCE: 41

Met Val Leu Ala Ser Ser Thr Thr Ser Ile His Thr Met Leu Leu Leu
1               5                   10                  15

Leu Leu Met Leu Phe His Leu Gly Leu Gln Ala Ser Ile Ser Ala Arg
            20                  25                  30

Gln Asn Ser Gly Leu His His Ile Leu Asp Ala Gln Lys Met Val Trp
        35                  40                  45

Asn His Arg Gly Ala Arg Gln Asp Tyr Lys Asp Asp Asp Lys Thr
    50                  55                  60

Arg Asn Ser Ser Pro Cys Pro Asn Asn Trp Ile Gln Asn Arg Glu Ser
65                  70                  75                  80

Cys Tyr Tyr Val Ser Glu Ile Trp Ser Ile Trp His Thr Ser Gln Glu
                85                  90                  95

Asn Cys Leu Lys Glu Gly Ser Thr Leu Leu Gln Ile Glu Ser Lys Glu
            100                 105                 110

Glu Met Asp Phe Ile Thr Gly Ser Leu Arg Lys Ile Lys Gly Ser Tyr
        115                 120                 125

Asp Tyr Trp Val Gly Leu Ser Gln Asp Gly His Ser Gly Arg Trp Leu
    130                 135                 140

Trp Gln Asp Gly Ser Ser Pro Ser Pro Gly Leu Leu Pro Ala Glu Arg
145                 150                 155                 160

Ser Gln Ser Ala Asn Gln Val Cys Gly Tyr Val Lys Ser Asn Ser Leu
                165                 170                 175

Leu Ser Ser Asn Cys Ser Thr Trp Lys Tyr Phe Ile Cys Glu Lys Tyr
            180                 185                 190

Ala Leu Arg Ser Ser Val
        195

<210> SEQ ID NO 42
<211> LENGTH: 460
<212> TYPE: PRT
<213> ORGANISM: Artificial Sequence
<220> FEATURE:
<223> OTHER INFORMATION: Amino acid sequence of heavy chain of 10B4
      anti-5B6 antibody

<400> SEQUENCE: 42

Met Leu Val Leu Gln Trp Val Leu Val Thr Ala Leu Phe Gln Gly Val
1               5                   10                  15

His Cys Ala Val Gln Ile Val Glu Ser Gly Gly Gly Leu Val Gln Pro
            20                  25                  30

Lys Glu Ser Leu Lys Ile Ser Cys Thr Ala Ser Gly Phe Thr Phe Ser
        35                  40                  45

Asn Ala Ala Ile Tyr Trp Val Arg Gln Thr Pro Gly Lys Gly Leu Glu
    50                  55                  60

```
Trp Val Gly Arg Ile Arg Thr Arg Pro Ser Lys Tyr Ala Thr Asp Tyr
 65                  70                  75                  80

Ala Asp Ser Val Arg Gly Arg Phe Thr Ile Ser Arg Asp Asp Ser Lys
                 85                  90                  95

Ser Met Val Tyr Leu Gln Met Asp Asn Leu Arg Thr Glu Asp Thr Ala
            100                 105                 110

Met Tyr Tyr Cys Thr Pro Arg Ala Thr Glu Asp Val Pro Phe Tyr Trp
            115                 120                 125

Gly Gln Gly Val Met Val Thr Val Ser Ser Ala Glu Thr Thr Ala Pro
            130                 135                 140

Ser Val Tyr Pro Leu Ala Pro Gly Thr Ala Leu Lys Ser Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ala Leu Ser Ser Gly Val His Thr Phe Pro
                180                 185                 190

Ala Val Leu Gln Ser Gly Leu Tyr Thr Leu Thr Ser Ser Val Thr Val
            195                 200                 205

Pro Ser Ser Thr Trp Ser Ser Gln Ala Val Thr Cys Asn Val Ala His
210                 215                 220

Pro Ala Ser Ser Thr Lys Val Asp Lys Lys Ile Val Pro Arg Glu Cys
225                 230                 235                 240

Asn Pro Cys Gly Cys Thr Gly Ser Glu Val Ser Ser Val Phe Ile Phe
                245                 250                 255

Pro Pro Lys Thr Lys Asp Val Leu Thr Ile Thr Leu Thr Pro Lys Val
                260                 265                 270

Thr Cys Val Val Asp Ile Ser Gln Asn Asp Pro Glu Val Arg Phe
            275                 280                 285

Ser Trp Phe Ile Asp Asp Val Glu Val His Thr Ala Gln Thr His Ala
            290                 295                 300

Pro Glu Lys Gln Ser Asn Ser Thr Leu Arg Ser Val Ser Glu Leu Pro
305                 310                 315                 320

Ile Val His Arg Asp Trp Leu Asn Gly Lys Thr Phe Lys Cys Lys Val
                325                 330                 335

Asn Ser Gly Ala Phe Pro Ala Pro Ile Glu Lys Ser Ile Ser Lys Pro
                340                 345                 350

Glu Gly Thr Pro Arg Gly Pro Gln Val Tyr Thr Met Ala Pro Pro Lys
                355                 360                 365

Glu Glu Met Thr Gln Ser Gln Val Ser Ile Thr Cys Met Val Lys Gly
            370                 375                 380

Phe Tyr Pro Pro Asp Ile Tyr Thr Glu Trp Lys Met Asn Gly Gln Pro
385                 390                 395                 400

Gln Glu Asn Tyr Lys Asn Thr Pro Pro Thr Met Asp Thr Asp Gly Ser
                405                 410                 415

Tyr Phe Leu Tyr Ser Lys Leu Asn Val Lys Lys Glu Thr Trp Gln Gln
                420                 425                 430

Gly Asn Thr Phe Thr Cys Ser Val Leu His Glu Gly Leu His Asn His
                435                 440                 445

His Thr Glu Lys Ser Leu Ser His Ser Pro Gly Lys
450                 455                 460

<210> SEQ ID NO 43
<211> LENGTH: 118
```

```
<212> TYPE: PRT
<213> ORGANISM: Artificial Sequence
<220> FEATURE:
<223> OTHER INFORMATION: Amino acid sequence of variable region of heavy
      chain of 10B4 anti-5B6 antibody

<400> SEQUENCE: 43

Gln Ile Val Glu Ser Gly Gly Gly Leu Val Gln Pro Lys Glu Ser Leu
1               5                   10                  15

Lys Ile Ser Cys Thr Ala Ser Gly Phe Thr Phe Ser Asn Ala Ala Ile
            20                  25                  30

Tyr Trp Val Arg Gln Thr Pro Gly Lys Gly Leu Glu Trp Val Gly Arg
        35                  40                  45

Ile Arg Thr Arg Pro Ser Lys Tyr Ala Thr Asp Tyr Ala Asp Ser Val
    50                  55                  60

Arg Gly Arg Phe Thr Ile Ser Arg Asp Asp Ser Lys Ser Met Val Tyr
65                  70                  75                  80

Leu Gln Met Asp Asn Leu Arg Thr Glu Asp Thr Ala Met Tyr Tyr Cys
                85                  90                  95

Thr Pro Arg Ala Thr Glu Asp Val Pro Phe Tyr Trp Gly Gln Gly Val
            100                 105                 110

Met Val Thr Val Ser Ser
        115

<210> SEQ ID NO 44
<211> LENGTH: 5
<212> TYPE: PRT
<213> ORGANISM: Artificial Sequence
<220> FEATURE:
<223> OTHER INFORMATION: Amino acid sequence of CDR1 of heavy chain of
      10B4 anti-5B6 antibody

<400> SEQUENCE: 44

Asn Ala Ala Ile Tyr
1               5

<210> SEQ ID NO 45
<211> LENGTH: 19
<212> TYPE: PRT
<213> ORGANISM: Artificial Sequence
<220> FEATURE:
<223> OTHER INFORMATION: Amino acid sequence of CDR2 of heavy chain of
      10B4 anti-5B6 antibody

<400> SEQUENCE: 45

Arg Ile Arg Thr Arg Pro Ser Lys Tyr Ala Thr Asp Tyr Ala Asp Ser
1               5                   10                  15

Val Arg Gly

<210> SEQ ID NO 46
<211> LENGTH: 9
<212> TYPE: PRT
<213> ORGANISM: Artificial Sequence
<220> FEATURE:
<223> OTHER INFORMATION: Amino acid sequence of CDR3 of heavy chain of
      10B4 anti-5B6 antibody

<400> SEQUENCE: 46

Arg Ala Thr Glu Asp Val Pro Phe Tyr
1               5

<210> SEQ ID NO 47
<211> LENGTH: 240
```

```
<212> TYPE: PRT
<213> ORGANISM: Artificial Sequence
<220> FEATURE:
<223> OTHER INFORMATION: Amino acid sequence of light chain of 10B4
      anti-5B6 antibody

<400> SEQUENCE: 47

Met Glu Ser Gln Thr Gln Val Leu Met Ser Leu Leu Leu Trp Val Ser
1               5                   10                  15

Gly Thr Cys Gly Asp Ile Val Met Thr Gln Thr Pro Ser Ser Gln Ala
            20                  25                  30

Val Ser Ala Gly Glu Lys Val Thr Met Asn Cys Lys Ser Ser Gln Ser
        35                  40                  45

Val Leu Tyr Asp Glu Asn Lys Lys Asn Tyr Leu Ala Trp Tyr Gln Gln
    50                  55                  60

Lys Ser Gly Gln Ser Pro Lys Leu Leu Ile Tyr Trp Ala Ser Thr Gly
65                  70                  75                  80

Glu Ser Gly Val Pro Asp Arg Phe Ile Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Gln Gln Tyr Tyr Asp Phe Pro Pro Thr Phe Gly Gly Gly Thr
        115                 120                 125

Lys Leu Glu Leu Lys Arg Ala Asp Ala Ala Pro Thr Val Ser Ile Phe
    130                 135                 140

Pro Pro Ser Met Glu Gln Leu Thr Ser Gly Gly Ala Thr Val Val Cys
145                 150                 155                 160

Phe Val Asn Asn Phe Tyr Pro Arg Asp Ile Ser Val Lys Trp Lys Ile
                165                 170                 175

Asp Gly Ser Glu Gln Arg Asp Gly Val Leu Asp Ser Val Thr Asp Gln
            180                 185                 190

Asp Ser Lys Asp Ser Thr Tyr Ser Met Ser Ser Thr Leu Ser Leu Thr
        195                 200                 205

Lys Val Glu Tyr Glu Arg His Asn Leu Tyr Thr Cys Glu Val Val His
    210                 215                 220

Lys Thr Ser Ser Pro Val Val Lys Ser Phe Asn Arg Asn Glu Cys
225                 230                 235                 240

<210> SEQ ID NO 48
<211> LENGTH: 109
<212> TYPE: PRT
<213> ORGANISM: Artificial Sequence
<220> FEATURE:
<223> OTHER INFORMATION: Amino acid sequence of variable region of the
      light chain of 10B4 anti-5B6 antibody

<400> SEQUENCE: 48

Asp Ile Val Met Thr Gln Thr Pro Ser Ser Gln Ala Val Ser Ala Gly
1               5                   10                  15

Glu Lys Val Thr Met Asn Cys Lys Ser Ser Gln Ser Val Leu Tyr Asp
            20                  25                  30

Glu Asn Lys Lys Asn Tyr Leu Ala Trp Tyr Gln Gln Lys Ser Gly Gln
        35                  40                  45

Ser Pro Lys Leu Leu Ile Tyr Trp Ala Ser Thr Gly Glu Ser Gly Val
    50                  55                  60

Pro Asp Arg Phe Ile Gly Ser Gly Ser Gly Thr Asp Phe Thr Leu Thr
65                  70                  75                  80
```

Ile Ser Ser Val Gln Ala Glu Asp Leu Ala Val Tyr Tyr Cys Gln Gln
            85                  90                  95

Tyr Tyr Asp Phe Pro Pro Thr Phe Gly Gly Gly Thr Lys
            100                 105

<210> SEQ ID NO 49
<211> LENGTH: 17
<212> TYPE: PRT
<213> ORGANISM: Artificial Sequence
<220> FEATURE:
<223> OTHER INFORMATION: Amino acid sequence of CDR1 of light chain of
      10B4 anti-5B6 antibody

<400> SEQUENCE: 49

Lys Ser Ser Gln Ser Val Leu Tyr Asp Glu Asn Lys Lys Asn Tyr Leu
1               5                   10                  15

Ala

<210> SEQ ID NO 50
<211> LENGTH: 7
<212> TYPE: PRT
<213> ORGANISM: Artificial Sequence
<220> FEATURE:
<223> OTHER INFORMATION: Amino acid sequence of CDR2 of light chain of
      10B4 anti-5B6 antibody

<400> SEQUENCE: 50

Trp Ala Ser Thr Gly Glu Ser
1               5

<210> SEQ ID NO 51
<211> LENGTH: 6
<212> TYPE: PRT
<213> ORGANISM: Artificial Sequence
<220> FEATURE:
<223> OTHER INFORMATION: Amino acid sequence of CDR3 of light chain of
      10B4 anti-5B6 antibody

<400> SEQUENCE: 51

Tyr Tyr Asp Phe Pro Pro
1               5

<210> SEQ ID NO 52
<211> LENGTH: 21
<212> TYPE: DNA
<213> ORGANISM: Artificial Sequence
<220> FEATURE:
<223> OTHER INFORMATION: Synthetic primer

<400> SEQUENCE: 52
ccagggcagt gctgggtgct t                                              21

<210> SEQ ID NO 53
<211> LENGTH: 28
<212> TYPE: DNA
<213> ORGANISM: Artificial Sequence
<220> FEATURE:
<223> OTHER INFORMATION: Synthetic primer

<400> SEQUENCE: 53
acgggtgagg atgatgtctt atgaacaa                                       28

<210> SEQ ID NO 54
<211> LENGTH: 42
<212> TYPE: DNA
<213> ORGANISM: Artificial Sequence
<220> FEATURE:
<223> OTHER INFORMATION: Synthetic primer

<400> SEQUENCE: 54
tagtaggaat tcagcactga caacagaacc ttaagcagta tg        42

<210> SEQ ID NO 55
<211> LENGTH: 45
<212> TYPE: DNA
<213> ORGANISM: Artificial Sequence
<220> FEATURE:
<223> OTHER INFORMATION: Synthetic primer

<400> SEQUENCE: 55
tagtagcgcg gccgctttac caggagagtg ggagagactc ttctc        45

<210> SEQ ID NO 56
<211> LENGTH: 45
<212> TYPE: DNA
<213> ORGANISM: Artificial Sequence
<220> FEATURE:
<223> OTHER INFORMATION: Synthetic primer

<400> SEQUENCE: 56
tagtaggaat tcggcgcgcc tcaaacaggc aggaggagca agatg        45

<210> SEQ ID NO 57
<211> LENGTH: 79
<212> TYPE: DNA
<213> ORGANISM: Artificial Sequence
<220> FEATURE:
<223> OTHER INFORMATION: Synthetic primer

<400> SEQUENCE: 57
tagtaggcgg ccgcacgcgt ctaacactca ttcctgttga agctcttgac gacgggtgag        60
gatgatgtct tatgaacaa        79

<210> SEQ ID NO 58
<211> LENGTH: 198
<212> TYPE: PRT
<213> ORGANISM: Artificial Sequence
<220> FEATURE:
<223> OTHER INFORMATION: Soluble mouse 5B6 including stalk

<400> SEQUENCE: 58

Glu Gln Gln Glu Arg Leu Ile Gln Gln Asp Thr Ala Leu Val Asn Leu
1               5                   10                  15

Thr Gln Trp Gln Arg Lys Tyr Thr Leu Glu Tyr Cys Gln Ala Leu Leu
            20                  25                  30

Gln Arg Ser Leu His Ser Gly Thr Asp Ala Ser Thr Gly Pro Val Leu
        35                  40                  45

Leu Thr Ser Pro Gln Met Val Pro Gln Thr Leu Asp Ser Lys Glu Thr
    50                  55                  60

Gly Ser Asp Cys Ser Pro Cys Pro His Asn Trp Ile Gln Asn Gly Lys
65                  70                  75                  80

Ser Cys Tyr Tyr Val Phe Glu Arg Trp Glu Met Trp Asn Ile Ser Lys
                85                  90                  95

Lys Ser Cys Leu Lys Glu Gly Ala Ser Leu Phe Gln Ile Asp Ser Lys
            100                 105                 110

Glu Glu Met Glu Phe Ile Ser Ser Ile Gly Lys Leu Lys Gly Gly Asn
        115                 120                 125

Lys Tyr Trp Val Gly Val Phe Gln Asp Gly Ile Ser Gly Ser Trp Phe
    130                 135                 140

Trp Glu Asp Gly Ser Ser Pro Leu Ser Asp Leu Leu Pro Ala Glu Arg
145                 150                 155                 160

Gln Arg Ser Ala Gly Gln Ile Cys Gly Tyr Leu Lys Asp Ser Thr Leu
                165                 170                 175

Ile Ser Asp Lys Cys Asp Ser Trp Lys Tyr Phe Ile Cys Glu Lys Lys
                180                 185                 190

Ala Phe Gly Ser Cys Ile
        195

<210> SEQ ID NO 59
<211> LENGTH: 175
<212> TYPE: PRT
<213> ORGANISM: Artificial Sequence
<220> FEATURE:
<223> OTHER INFORMATION: Soluble human 5B6 including stalk

<400> SEQUENCE: 59

Gln Gln Gln Glu Lys Leu Ile Gln Gln Glu Arg Ala Leu Leu Asn Phe
1               5                   10                  15

Thr Glu Trp Lys Arg Ser Cys Ala Leu Gln Met Lys Tyr Cys Gln Ala
            20                  25                  30

Phe Met Gln Asn Ser Leu Ser Ser Ala His Asn Ser Ser Pro Cys Pro
        35                  40                  45

Asn Asn Trp Ile Gln Asn Arg Glu Ser Cys Tyr Tyr Val Ser Glu Ile
    50                  55                  60

Trp Ser Ile Trp His Thr Ser Gln Glu Asn Cys Leu Lys Glu Gly Ser
65                  70                  75                  80

Thr Leu Leu Gln Ile Glu Ser Lys Glu Glu Met Asp Phe Ile Thr Gly
                85                  90                  95

Ser Leu Arg Lys Ile Lys Gly Ser Tyr Asp Tyr Trp Val Gly Leu Ser
            100                 105                 110

Gln Asp Gly His Ser Gly Arg Trp Leu Trp Gln Asp Gly Ser Ser Pro
        115                 120                 125

Ser Pro Gly Leu Leu Pro Ala Glu Arg Ser Gln Ser Ala Asn Gln Val
    130                 135                 140

Cys Gly Tyr Val Lys Ser Asn Ser Leu Leu Ser Ser Asn Cys Ser Thr
145                 150                 155                 160

Trp Lys Tyr Phe Ile Cys Glu Lys Tyr Ala Leu Arg Ser Ser Val
                165                 170                 175

<210> SEQ ID NO 60
<211> LENGTH: 134
<212> TYPE: PRT
<213> ORGANISM: Artificial Sequence
<220> FEATURE:
<223> OTHER INFORMATION: Soluble mouse 5B6 without stalk

<400> SEQUENCE: 60

Gly Ser Asp Cys Ser Pro Cys Pro His Asn Trp Ile Gln Asn Gly Lys
1               5                   10                  15

Ser Cys Tyr Tyr Val Phe Glu Arg Trp Glu Met Trp Asn Ile Ser Lys
            20                  25                  30

Lys Ser Cys Leu Lys Glu Gly Ala Ser Leu Phe Gln Ile Asp Ser Lys
        35                  40                  45

Glu Glu Met Glu Phe Ile Ser Ser Ile Gly Lys Leu Lys Gly Gly Asn
    50                  55                  60

```
Lys Tyr Trp Val Gly Val Phe Gln Asp Gly Ile Ser Gly Ser Trp Phe
 65                  70                  75                  80

Trp Glu Asp Gly Ser Ser Pro Leu Ser Asp Leu Leu Pro Ala Glu Arg
                 85                  90                  95

Gln Arg Ser Ala Gly Gln Ile Cys Gly Tyr Leu Lys Asp Ser Thr Leu
            100                 105                 110

Ile Ser Asp Lys Cys Asp Ser Trp Lys Tyr Phe Ile Cys Glu Lys Lys
        115                 120                 125

Ala Phe Gly Ser Cys Ile
    130

<210> SEQ ID NO 61
<211> LENGTH: 133
<212> TYPE: PRT
<213> ORGANISM: Artificial Sequence
<220> FEATURE:
<223> OTHER INFORMATION: Soluble human 5B6 without stalk

<400> SEQUENCE: 61

Asn Ser Ser Pro Cys Pro Asn Asn Trp Ile Gln Asn Arg Glu Ser Cys
 1               5                  10                  15

Tyr Tyr Val Ser Glu Ile Trp Ser Ile Trp His Thr Ser Gln Glu Asn
                 20                  25                  30

Cys Leu Lys Glu Gly Ser Thr Leu Leu Gln Ile Glu Ser Lys Glu Glu
            35                  40                  45

Met Asp Phe Ile Thr Gly Ser Leu Arg Lys Ile Lys Gly Ser Tyr Asp
    50                  55                  60

Tyr Trp Val Gly Leu Ser Gln Asp Gly His Ser Gly Arg Trp Leu Trp
 65                  70                  75                  80

Gln Asp Gly Ser Ser Pro Ser Pro Gly Leu Leu Pro Ala Glu Arg Ser
                 85                  90                  95

Gln Ser Ala Asn Gln Val Cys Gly Tyr Val Lys Ser Asn Ser Leu Leu
            100                 105                 110

Ser Ser Asn Cys Ser Thr Trp Lys Tyr Phe Ile Cys Glu Lys Tyr Ala
        115                 120                 125

Leu Arg Ser Ser Val
    130

<210> SEQ ID NO 62
<211> LENGTH: 129
<212> TYPE: PRT
<213> ORGANISM: Mus musculus

<400> SEQUENCE: 62

Pro Cys Pro His Asn Trp Ile Gln Asn Gly Lys Ser Cys Tyr Tyr Val
 1               5                  10                  15

Phe Glu Arg Trp Glu Met Trp Asn Ile Ser Lys Lys Ser Cys Leu Lys
                 20                  25                  30

Glu Gly Ala Ser Leu Phe Gln Ile Asp Ser Lys Glu Glu Met Glu Phe
            35                  40                  45

Ile Ser Ser Ile Gly Lys Leu Lys Gly Asn Lys Tyr Trp Val Gly Gly
    50                  55                  60

Val Phe Gln Asp Gly Ile Ser Gly Ser Trp Phe Trp Glu Asp Gly Ser
 65                  70                  75                  80

Ser Pro Leu Ser Asp Leu Leu Pro Ala Glu Arg Gln Arg Ser Ala Gly
                 85                  90                  95
```

-continued

```
Gln Ile Cys Gly Tyr Leu Lys Asp Ser Thr Leu Ile Ser Asp Lys Cys
            100                 105                 110

Asp Ser Trp Lys Tyr Phe Ile Cys Glu Lys Lys Ala Phe Gly Ser Cys
        115                 120                 125

Ile

<210> SEQ ID NO 63
<211> LENGTH: 130
<212> TYPE: PRT
<213> ORGANISM: Homo sapiens

<400> SEQUENCE: 63

Pro Cys Pro Asn Asn Trp Ile Gln Asn Arg Glu Ser Cys Tyr Tyr Val
1               5                   10                  15

Ser Glu Ile Trp Ser Ile Trp His Thr Ser Gln Glu Asn Cys Leu Lys
            20                  25                  30

Glu Gly Ser Thr Leu Leu Gln Ile Glu Ser Lys Glu Glu Met Asp Phe
        35                  40                  45

Ile Thr Gly Ser Leu Arg Lys Ile Lys Gly Ser Tyr Asp Tyr Trp Val
    50                  55                  60

Gly Leu Ser Gln Asp Gly His Ser Gly Arg Trp Leu Trp Gln Asp Gly
65                  70                  75                  80

Ser Ser Pro Ser Pro Gly Leu Leu Pro Ala Glu Arg Ser Gln Ser Ala
                85                  90                  95

Asn Gln Val Cys Gly Tyr Val Lys Ser Asn Ser Leu Leu Ser Ser Asn
            100                 105                 110

Cys Ser Thr Trp Lys Tyr Phe Ile Cys Glu Lys Tyr Ala Leu Arg Ser
        115                 120                 125

Ser Val
    130
```

DENDRITIC CELL MARKER AND USES THEREOF

FIELD OF THE INVENTION

The present invention relates to the identification of proteins located on the cell surface of dendritic cells and precursors thereof, particularly antigen presenting dendritic cells. In particular, the present invention relates to compounds such as antibodies that bind these proteins. These compounds can be used to detect and/or enrich a subset of dendritic cells or precursors thereof. These compounds can also be used to target an antigen to dendritic cells or precursors thereof to modulate a humoral and/or T cell mediated immune response to the antigen, or used to target cytotoxic agents to dendritic cells or precursors thereof involved in diseased states.

BACKGROUND OF THE INVENTION

Dendritic cells are bone marrow derived cells, sparsely distributed in lymphoid organs, blood and peripheral tissues, that are critical in the initiation and maintenance of an immune response. DC share common properties such as antigen (Ag) processing and the ability to activate naïve T cells. However DC are heterogeneous, with at least seven distinct subtypes detected in the mouse (Shortman and Liu, 2002).

DC can be broadly classified into conventional DC (cDC) and plasmacytoid pre-DC (pDC). The pDC are able to secrete high levels of IFN$\alpha$ and only develop into DC upon activation (O'Keeffe et al., 2002; Hochrein et al., 2001). The cDC may be divided into the classical "migratory" or interstitial DC (such as Langerhans' cells), which migrate to the lymph nodes (LN) from peripheral tissues via the lymph and the "lymphoid tissue resident" DC (found in spleen, thymus and LN), which do not migrate in this way but which arise from blood-borne precursors.

The lymphoid tissue resident DC of mice may in turn be divided into the CD4$^-$ 8$^-$ (DN), the CD4$^+$8$^-$ (CD4$^+$) and the CD4$^-$8$^+$ (CD8$^+$) cDC subsets, where the CD4 and DN are collectively referred to as the CD8$^-$ DC. In addition, there are inflammatory DC which develop as a consequence of infection or inflammation (Shortman and Naik, 2007). These DC subtypes share many functions, especially the uptake, processing and presentation of antigen (Ag) to activate naïve T cells.

Importantly, DC also exhibit subset-specific roles. Different DC subtypes express different patterns of Toll-like receptors (TLR) and consequently vary in their capacity to respond to different infections (Proietto et al., 2004; Takdea et al., 2003). Whilst chemokine production is carried out primarily by CD8$^-$ DC, the CD8$^+$ DC are the major producers of IL-12, which directs a Th1 T cell response. The capacity to cross-present exogenous Ags via MHC class I molecules, is an activity performed very efficiently by the CD8$^+$ DC subset (Pooley et al., 2001; den Haan et al., 2000), which allows these DC to be major presenters of viral Ag to CD8$^+$ T cells (Belz et al., 2004; Smith et al., 2003). By contrast, CD8$^-$ DC appear better equipped for initiating MHC class II restricted responses (Dudziak et al., 2007; Schnorrer et al., 2006).

Molecules on the surface of DC are important in the recognition, communication and activation functions of DC. The molecules that differ between DC subtypes are of interest, since they may underpin the functional differences observed between these subtypes. Furthermore, surface molecules differing between the DC subtypes are of special interest, since they may serve as beacons for selective delivery to the DC of Ag or therapeutic agents in order to manipulate immune responses.

Antibodies (Ab) against DC cell surface molecules have been used to deliver Ag to DC and induce tolerance (Bonifaz et al., 2002; Finkelman et al., 1996). Immunity to the targeted Ag has also been induced, although in most studies only when the antibody-antigen complex is co-administered with a DC maturation agent or adjuvant (Bonifaz et al., 2002; Carter et al., 2006). Importantly, the efficiency of targeting Ag using cell surface molecules and raising immunity will depend on several factors: (i) the subset of DCs targeted; (ii) dose-dependent effects relating to the expression level of the targeted molecules; (iii) the expression of the targeted molecule on cell types other than DC, which may limit the effectiveness of targeting or potentially introduce contributions by these non-DC; (iv) the function of the targeted molecule, which may affect Ag processing or deliver signals that induce or impair DC maturation; (v) the TLR profile of the targeted DC subset, particularly when TLR ligands are co-administered. All of the above factors will impact the ability to raise immune responses in a clinical setting. Of necessity, these details must first be established with experimental animals such as mice, before translation to humans. Thus, what is needed for targeting Ag to DC and efficient vaccination is a DC surface molecule that is conserved between mouse and man, in terms of molecular and functional characteristics and restricted expression pattern.

It appears that humans contain equivalents of the murine DC subsets. The division into cDC and pDC is well established as is the presence of Langerhans' cells. The close similarity between mouse and human DC when extracted from the same tissue source (thymus) (O'Keeffe et al., 2003; Vandenabeele et al., 2001) suggests a close similarity. However, the human equivalents of most of the murine "lymphoid organ resident" DC subsets remain unknown, due to the lack of conserved surface markers between species (i.e. the CD8 marker is not expressed on human DC) and the difficulty in obtaining samples of human lymphoid organs for analysis. What is needed to facilitate the translation of mouse biology into human clinical applications is the identification of DC subset-specific marker molecules conserved between mice, humans, and other species. Such surface molecules might allow the tailoring of immune responses by harnessing the specific immune functions of distinct DC subtypes.

There is a need for the identification of dendritic cell markers that can be used to target therapies, such as vaccines, to dendritic cells.

SUMMARY OF THE INVENTION

The present inventors have identified a novel surface C-type lectin-like molecule, 5B6, that is preferentially expressed by mouse pDC, CD8$^+$ cDC, as well as human DC subtypes and dendritic cell precursors. Targeted delivery of antigen to DC via the 5B6 molecule was found to enhance an immune response to the antigen. This was obtained even in the absence of additional adjuvants. Thus, the present inventors have identified a novel surface marker that can be used, inter alia, to both identify mouse CD8$^+$ DC and their human counterparts, and to deliver antigen to DCs or precursors thereof to manipulate immune responses and enhance vaccine effectiveness.

Accordingly, in a first aspect the present invention provides a compound that binds a polypeptide which comprises:

i) an amino acid sequence as provided in any one of SEQ ID NO's 1 to 8;

ii) an amino acid sequence which is at least 50% identical to any one or more of SEQ ID NO's 1 to 8; and/or iii) a biologically active and/or antigenic fragment of i) or ii).

In one embodiment, the compound is a polypeptide.

In a preferred embodiment, the compound is an antibody or antigenic binding fragment thereof. Examples of such antibodies include, but are not limited to, monoclonal antibodies, humanized antibodies, single chain antibodies, diabodies, triabodies, or tetrabodies.

In an embodiment, the antibody or antigenic binding fragment thereof comprises at least one complementarity determining region (CDR) comprising an amino acid sequence which is at least 90% identical to any one of SEQ ID NO's 44 to 46 or 49 to 51.

In a further embodiment, the antibody or antigenic binding fragment thereof comprises an immunoglobulin heavy chain or fragment thereof comprising three CDRs, and wherein i) CDR1 comprises an amino acid sequence which is at least 90% identical to SEQ ID NO:44, ii) CDR2 comprises an amino acid sequence which is at least 90% identical to SEQ ID NO:45, and iii) CDR3 comprises an amino acid sequence which is at least 90% identical to SEQ ID NO:46.

In another embodiment, the antibody or antigenic binding fragment thereof comprises an immunoglobulin light chain or fragment thereof comprising three CDRs, and wherein i) CDR1 comprises an amino acid sequence which is at least 90% identical to SEQ ID NO:49, ii) CDR2 comprises an amino acid sequence which is at least 90% identical to SEQ ID NO:50, and iii) CDR3 comprises an amino acid sequence which is at least 90% identical to SEQ ID NO:51.

In a further embodiment, the antibody or antigenic binding fragment thereof comprises i) an immunoglobulin heavy chain or fragment thereof comprising a variable region comprising an amino acid sequence which is at least 90% identical to SEQ ID NO:43, and/or ii) an immunoglobulin light chain or fragment thereof comprising a variable region comprising an amino acid sequence which is at least 90% identical to SEQ ID NO:48.

In yet a further embodiment, the antibody or antigenic binding fragment thereof comprises i) an immunoglobulin heavy chain or fragment thereof comprising an amino acid sequence which is at least 90% identical to SEQ ID NO:42, and/or ii) an immunoglobulin light chain or fragment thereof comprising an amino acid sequence which is at least 90% identical to SEQ ID NO:47.

In an embodiment, the antibody is 24/04-10B4 (also referred to herein as 10B4), 42/04-42D2 (also referred to herein as 42D2), 20/05-3A4 (also referred to herein as 3A4) or 23/05-4C6 (also referred to herein as 4C6), or antibody which comprises at least one complementarity determining region of 24/04-10B4, 42/04-42D2, 20/05-3A4 or 23/05-4C6. Antibodies 24/04-10B4, 42/04-42D2, 20/05-3A4 and 23/05-4C6 are produced by hybridoma cell lines deposited with the European Collection of Cell Cultures (ECACC) 24/04-10B4-24-8, 42/04-42D2-66-4-1, 20/05-3A4-26-16, 23/05-4C6-29-3 on 11 Dec. 2007 under Deposit Reference Numbers 07121101, 07121102, 07121103, and 07121104 respectively. Higher antibody secreting subclones of these hybridomas (24/04-10B4-24-8-FACS 9-5, 42/04-42D2-66-4-1-Clone 4, 20/05-3A4-26-16-Clone 5, 23/05-4C6-29-3-Clone 5) were deposited with the ECACC on 29 Apr. 2008 under Deposit Reference No's 08042901, 08041902, 08042903, and 08042904 respectively.

The present inventors have also found that soluble fragments of 5B6 are capable of binding to full length membrane bound 5B6. Thus, in an alternate embodiment the compound is a soluble fragment of a polypeptide which comprises:

i) an amino acid sequence as provided in any one of SEQ ID NO's 1 to 8; or ii) an amino acid sequence which is at least 50% identical to any one or more of SEQ ID NO's 1 to 8, wherein the soluble fragment does not comprise at least the about 40, at least about 50, at least about 55, or at least about 100, N-terminal residues of any one of SEQ ID NO's 1 to 8.

Preferably, the soluble fragment comprises the C-type lectin-like domain of a polypeptide which comprises:

i) an amino acid sequence as provided in any one of SEQ ID NO's 1 to 8; or ii) an amino acid sequence which is at least 50% identical to any one or more of SEQ ID NO's 1 to 8.

In a further embodiment, the soluble fragment comprises:

i) an amino acid sequence as provided in any one of SEQ ID NO's 58 to 61; or ii) an amino acid sequence which is at least 50% identical to any one or more of SEQ ID NO's 58 to 61, wherein the soluble fragment does not comprise at least the about 40 N-terminal residues of any one of SEQ ID NO's 1 to 8, and wherein the soluble fragment is capable of binding a polypeptide which comprises an amino acid sequence as provided in any one of SEQ ID NO's 1 to 8.

Preferably, the compound specifically binds the protein.

Preferably, the compound binds a region of the polypeptide other than at least the about 40, at least about 50, at least about 55, or at least about 100, N-terminal residues of any one of SEQ ID NO's 1 to 8.

In another aspect, the present invention provides a compound that competitively binds to a polypeptide with an antibody that binds the polypeptide, wherein the polypeptide comprises an amino acid sequence as provided in any one of SEQ ID NO's 1 to 8.

In a preferred embodiment, the antibody is 24/04-10B4, 42/04-42D2, 20/05-3A4 and/or 23/05-4C6.

Compounds of the invention can be used to deliver a therapeutic agent to a dendritic cell or precursors thereof, in particular an antigen presenting dendritic cell. Thus, in a further embodiment, the compound is conjugated to a therapeutic agent. Examples of such agents include, but are not limited to, an antigen, a cytotoxic agent, a drug and/or pharmacological agent.

The antigen can be any molecule that induces an immune response in an animal. Examples include, but are not limited to, a cancer antigen, a self antigen, an allergen, and/or an antigen from a pathogenic and/or infectious organism.

In an embodiment, the antigen from a pathogenic and/or infectious organism can be from, but not limited to, *Plasmodium falciparum* or *Plasmodium vivax*.

In another embodiment, the compound is detectably labelled.

In an embodiment, the compound is an isolated and/or recombinant compound.

Also provided is a stable antibody producing cell line capable of producing an antibody of the invention. Examples of such cell lines are 24/04-10B4 as deposited with the European Collection of Cell Cultures (ECACC) on 11 Dec. 2007 under Deposit Reference 07121101 and a higher producing subclone of it as deposited with the ECACC on 29 Apr. 2008 under Deposit Reference 08042901, 42/04-42D2 as deposited with the ECACC on 11 Dec. 2007 under the Deposit Reference 07121102 and a higher producing subclone of it as deposited with the ECACC on 29 Apr. 2008 under Deposit Reference 08041902, 20/05-3A4 as deposited with the European Collection of Cell Cultures (ECACC) on 11 Dec. 2007 under Deposit Reference 07121103 and a higher producing subclone of it as deposited with the ECACC on 29 Apr. 2008 under Deposit Reference 08042903, and 23/05-4C6 as deposited with the European Collection of Cell Cultures (ECACC) on 11 Dec. 2007 under Deposit Reference 07121104 and a higher producing subclone of it as deposited with the ECACC on 29 Apr. 2008 under Deposit Reference 08042904.

In a further aspect, the present invention provides a composition comprising a compound of the invention and a pharmaceutically acceptable carrier.

In an embodiment, the composition further comprises an adjuvant.

In another embodiment, the compound is encapsulated in, or exposed on the surface of, a liposome.

In another aspect, the present invention provides a method of modulating an immune response in a subject, the method comprising administering to the subject a compound of the invention and/or a composition of the invention.

In an embodiment, the immune response to an antigen is induced and/or enhanced.

In a particularly preferred embodiment, the immune response is modulated by enhancing a helper T cell response.

In a further preferred embodiment, the immune response is modulated by the activation of CD4+ and/or CD8+ T cells.

In another particularly preferred embodiment, the immune response is modulated by enhancing B cell antibody production. Examples of antibodies produced include, but are not necessarily limited to, IgG1, IgG2b, IgG2c and/or IgG3 antibody isotypes.

In a further preferred embodiment, the immune response is modulated by generating a memory response.

In a particularly preferred embodiment, the subject is administered with a compound of the invention conjugated to an antigen.

In another embodiment, an immune response to a self antigen or allergen is reduced. In this embodiment, it is preferred that the immune response is modulated by suppressing a T cell response and/or a B cell antibody response.

In a further aspect, the present invention provides a method of modulating an immune response to an antigen in a subject, the method comprising exposing dendritic cells or precursors thereof in vitro to a compound of the invention and/or a composition of the invention, and administering said cells to the subject.

In an embodiment, the cells have been isolated from the subject.

Preferably, a humoral and/or T cell mediated response is modulated.

In a further embodiment, naïve CD8+ T cell activation, and/or naïve CD4+ T cell activation, is modulated.

In yet another embodiment, the humoral response comprises the production of IgG1, IgG2b, IgG2c and/or IgG3 antibody isotypes. In another embodiment, the humoral response at least comprises the production of IgG1 antibody isotype.

Preferably, the dendritic cell is an animal dendritic cell or precursor of an animal dendritic cell. More preferably, the dendritic cell is a human dendritic cell. Even more preferably, the human dendritic cell is Necl-2+, HLA DR+ and/or BDCA-3+.

In yet another aspect, the present invention provides a method of treating and/or preventing a disease involving dendritic cells or precursors thereof, the method comprising administering to the subject a compound of the invention, and/or a composition of the invention.

Preferably, the method comprises administering a compound conjugated to a cytotoxic agent, drug and/or pharmacological agent.

In a further aspect, the present invention provides a method of treating and/or preventing a disease involving dendritic cells or precursors thereof, the method comprising administering to the subject an isolated polynucleotide and/or construct encoding said polynucleotide which, when present in a cell of the subject, modulates the level of activity of a polypeptide which comprises:

i) an amino acid sequence as provided in any one of SEQ ID NO's 1 to 8; and/or ii) an amino acid sequence which is at least 50% identical to any one or more of SEQ ID NO's 1 to 8, in the cell when compared to a cell that lacks said polynucleotide.

In an embodiment, the polynucleotide down-regulates the level of activity of the polypeptide in the cell. Examples of such polynucleotides include, but are not limited to, an antisense polynucleotide, a sense polynucleotide, a catalytic polynucleotide, a microRNA, and a double stranded RNA.

In an alternate embodiment, the polynucleotide up-regulates the level of activity of the polypeptide. For example, the polynucleotide encodes a polypeptide which comprises an amino acid sequence as provided in any one of SEQ ID NO's 1 to 8.

Examples of diseases involving dendritic cells or precursors thereof include, but are not limited to, cancer, an infection, an autoimmune disease or an allergy.

In an embodiment, the autoimmune disease is lupus erythematosus.

In another embodiment, the infection is a *Plasmodium* sp., such as *Plasmodium falciparum* or *Plasmodium vivax*, infection.

In another aspect, the present invention provides for the use of a compound of the invention, and/or a composition of the invention for the manufacture of a medicament for modulating an immune response in a subject.

In a further aspect, the present invention provides for the use of dendritic cells or precursors thereof exposed in vitro to a compound of the invention and/or a composition of the invention for the manufacture of a medicament for modulating an immune response to an antigen in a subject.

In yet another aspect, the present invention provides for the use of a compound of the invention and/or a composition of the invention for the manufacture of a medicament for treating and/or preventing a disease involving dendritic cells or precursors thereof in a subject.

In a further aspect, the present invention provides a method of enriching dendritic cells, or a subset or precursors thereof, from a sample comprising;

i) contacting a sample comprising dendritic cells or precursors thereof with a compound of the invention, and ii) isolating cells bound to the compound.

In another aspect, the present invention provides a method of enriching dendritic cells, or a subset or precursors thereof, from a sample comprising;

i) contacting a sample comprising dendritic cells or precursors thereof with a detectably labelled first polynucleotide that hybridizes to a second polynucleotide encoding a polypeptide which comprises
   a) an amino acid sequence as provided in any one of SEQ ID NO's 1 to 8; and/or
   b) an amino acid sequence which is at least 50% identical to any one or more of SEQ ID NO's 1 to 8, and
ii) isolating the detectably labelled cells.

In a preferred embodiment, the cells obtained from step ii) of the two above methods are administered to a subject. In an embodiment, the cells are administered to treat and/or prevent a disease selected from cancer, an infection, an autoimmune disease or an allergy.

In a further aspect, the present invention provides a method of detecting dendritic cells, or a subset or precursors thereof, in a sample comprising;
   i) contacting a sample comprising dendritic cells or precursors thereof with a compound of the invention,
   ii) detecting cells bound to the compound.

In yet another aspect, the present invention provides a method of detecting dendritic cells, or a subset or precursors thereof, in a sample comprising;
   i) contacting a sample comprising dendritic cells or precursors thereof with a detectably labelled first polynucleotide that hybridizes to a second polynucleotide encoding a polypeptide which comprises
      a) an amino acid sequence as provided in any one of SEQ ID NO's 1 to 8; and/or
      b) an amino acid sequence which is at least 50% identical to any one or more of SEQ ID NO's 1 to 8, and
   ii) detecting the detectably labelled cells.

In another aspect, the present invention provides a method of detecting dendritic cells, or a subset or precursors thereof, in a subject comprising;
   i) administering to the subject a compound of the invention,
   ii) detecting cells bound to the compound.

In an embodiment, the compound is detectably labelled. However, as the skilled addressee will appreciate other procedures could be used, for example, using a detectably labelled secondary antibody that binds the compound.

In a further aspect, the present invention provides a method of detecting dendritic cells, or a subset or precursors thereof, in a subject comprising;
   i) administering to the subject a detectably labelled first polynucleotide that hybridizes to a second polynucleotide encoding a polypeptide which comprises
      a) an amino acid sequence as provided in any one of SEQ ID NO's 1 to 8; and/or
      b) an amino acid sequence which is at least 50% identical to any one or more of SEQ ID NO's 1 to 8, and,
   ii) detecting the detectably labelled cells.

In a preferred embodiment, the dendritic cells express one or more of the following markers, CD8, CD24, Necl-2, CD11c, HLADR and BDCA3.

Preferably, the dendritic cells are human dendritic cells that express one or more of the following markers, Necl-2, HLADR and BDCA3.

In an alternative embodiment, the dendritic cells are murine dendritic cells that express one or more of the following markers, CD24, Necl-2, CD11c and CD8.

Preferably, the precursor dendritic cells are intermediate or late precursor dendritic cells which are capable of differentiating into dendritic cells in culture and/or on transfer into irradiated recipients.

Preferably, the subject is an animal. More preferably, the subject is a mammal such as a human, dog, cat, horse, cow, or sheep. Most preferably, the subject is a human.

The present inventors have also identified that some B cells express the polypeptide of the invention. Such cells can be distinguished and/or separated from dendritic cells or precursors thereof by targeting any B cell marker known in the art such as CD19.

In another aspect, the present invention provides a substantially purified and/or recombinant polypeptide which comprises:
   i) an amino acid sequence as provided in any one of SEQ ID NO's 1 to 8;
   ii) an amino acid sequence which is at least 50% identical to any one or more of SEQ ID NO's 1 to 8; and/or
   iii) a biologically active and/or antigenic fragment of i) or ii).

Preferably, the polypeptide is a dendritic cell, or precursor thereof, marker.

Preferably, the polypeptide comprises at least one C-type lectin like domain. More preferably, the polypeptide comprises a single C-type lectin like domain.

In an embodiment, the polypeptide lacks a transmembrane domain. Examples of such soluble fragments are provided herein. In an embodiment, the biologically active and/or antigenic fragment is a soluble fragment which comprises:
   i) an amino acid sequence as provided in any one of SEQ ID NO's 58 to 61; or
   ii) an amino acid sequence which is at least 50% identical to any one or more of SEQ ID NO's 58 to 61, wherein the soluble fragment does not comprise at least the about 40 N-terminal residues of any one of SEQ ID NO's 1 to 8, and wherein the soluble fragment is capable of binding a polypeptide which comprises an amino acid sequence as provided in any one of SEQ ID NO's 1 to 8.

In another embodiment, the polypeptide comprises a transmembrane domain.

Preferably, the polypeptide can be purified from dendritic cells or precursors thereof.

Preferably, the polypeptide can be purified from an animal, or cells therefrom. More preferably, the polypeptide can be purified from a mammal such as a human, dog, cat, horse, cow, or sheep. Most preferably, the polypeptide can be purified from a human.

In another embodiment, the polypeptide is fused to at least one other polypeptide. The at least one other polypeptide may be a polypeptide that enhances the stability of a polypeptide of the present invention, or a polypeptide that assists in the purification or detection of the fusion protein.

In another aspect, the present invention provides an isolated and/or exogenous polynucleotide which comprises:
   i) a nucleotide sequence as provided in any one of SEQ ID NO's 9 to 16;
   ii) a nucleotide sequence which is at least 50% identical to any one or more of SEQ ID NO's 9 to 16;
   iii) a nucleotide sequence encoding a polypeptide of the invention,
   iv) a nucleotide sequence encoding a compound of the invention; and/or
   v) a sequence nucleotide which hybridizes to any one or more of i) to iv) or a complement thereof.

In an embodiment, the polynucleotide comprises a nucleotide sequence which hybridizes to any one or more of SEQ ID NO's 9 to 16 under stringent conditions.

Preferably, the polynucleotide is operably linked to a promoter capable of directing expression of the polynucleotide in a cell.

In a further aspect, the present invention provides an isolated polynucleotide which, when present in a cell of a subject, modulates the level of activity of a polypeptide of the invention in the cell when compared to a cell that lacks said polynucleotide.

In an embodiment, the polynucleotide is operably linked to a promoter capable of directing expression of the polynucleotide in a cell of an animal.

In a preferred embodiment, the polynucleotide down-regulates mRNA levels from a gene encoding the polypeptide. Examples of such polynucleotides include, but are not limited to, an antisense polynucleotide, a sense polynucleotide, a catalytic polynucleotide, a microRNA and a double stranded RNA (dsRNA).

In an embodiment, the antisense polynucleotide hybridises under physiological conditions to a polynucleotide comprising any one or more of the sequence of nucleotides provided as SEQ ID NO's 9 to 16.

In another embodiment, the catalytic polynucleotide is capable of cleaving a polynucleotide comprising any one or more of the sequence of nucleotides provided as SEQ ID NO's 9 to 16.

In a further embodiment, the dsRNA molecule comprises an oligonucleotide which comprises at least 19 contiguous nucleotides of any one or more of the sequence of nucleotides provided as SEQ ID NOs 9 to 16 where T is replaced with a U, wherein the portion of the molecule that is double stranded is at least 19 basepairs in length and comprises said oligonucleotide.

In yet a further embodiment, the dsRNA molecule is expressed from a single promoter, wherein the strands of the double stranded portion are linked by a single stranded portion.

In an alternate embodiment, the polynucleotide up-regulates mRNA levels from a gene encoding the polypeptide. For example, the polynucleotide encodes the polypeptide.

Also provided is a vector comprising at least one polynucleotide of the invention. Preferably, the vector is an expression vector.

In a further aspect, the present invention provides a host cell comprising at least one polynucleotide of the invention, and/or at least one vector of the invention. The cell can be any cell type such as, but not limited to, a bacterial, yeast, animal, insect or plant cell.

In a further aspect, the present invention provides a transgenic plant comprising an exogenous polynucleotide of the invention.

Preferably, the exogenous polynucleotide encodes a polypeptide of the invention or a compound of the invention.

In an embodiment, the polynucleotide encodes a compound of the invention conjugated to an antigen.

In another aspect, the present invention provides a transgenic non-human animal comprising an exogenous polynucleotide of the invention.

In a further aspect, the present invention provides an extract of a host cell of the invention, the plant of the invention and/or the animal of the invention, wherein the extract comprises a compound of the invention, a polypeptide of the invention and/or a polynucleotide of the invention.

Also provided is a process for preparing a compound of the invention or a polypeptide of the invention, the process comprising cultivating a host cell of the invention, a vector of the invention, a plant of the invention and/or a non-human animal of the invention, under conditions which allow expression of the polynucleotide encoding the compound or polypeptide, and recovering the expressed compound or polypeptide.

In another aspect, the present invention provides a compound or polypeptide produced using the method of the invention.

In a further aspect, the present invention provides an enriched population of dendritic cells, and/or precursors thereof, obtained by a method of the invention.

In a further aspect, the present invention provides an enriched population of dendritic cells, and/or precursors thereof, expressing a polypeptide which comprises:

i) an amino acid sequence as provided in any one of SEQ ID NO's 1 to 8;

ii) an amino acid sequence which is at least 50% identical to any one or more of SEQ ID NO's 1 to 8; and/or iii) a biologically active and/or antigenic fragment of i) or ii).

In a further aspect, the present invention provides an expanded dendritic cell population, and/or precursors thereof, obtained by culturing an enriched population of dendritic cells and/or precursors thereof of the invention.

In another aspect, the present invention provides a composition comprising a polypeptide of the invention, a polynucleotide of the invention, a vector of the invention, a host cell of the invention, a transgenic plant of the invention, an extract of the invention and/or a cell population of the invention, and a pharmaceutically acceptable carrier.

In yet another aspect, the present invention provides a method of identifying a molecule that binds to a polypeptide of the invention, the method comprising:

i) contacting a polypeptide of the invention with a candidate compound, ii) determining whether the compound binds the polypeptide.

In a further aspect, the present invention provides a method of identifying a molecule that binds to a polypeptide of the invention, the method comprising:

a) exposing a polypeptide of the invention to a binding partner which binds the polypeptide, and a candidate agent, and b) assessing the ability of the candidate agent to compete with the binding partner for binding to the polypeptide.

In an embodiment, the binding partner is an antibody. In another embodiment, the binding partner is a soluble fragment of a polypeptide which comprises:

i) an amino acid sequence as provided in any one of SEQ ID NO's 1 to 8; or ii) an amino acid sequence which is at least 50% identical to any one or more of SEQ ID NO's 1 to 8, wherein the soluble fragment does not comprise at least the about 40, at least about 50, or at least about 55, N-terminal residues of any one of SEQ ID NO's 1 to 8.

In another embodiment, the binding partner is detectably labelled.

In a further embodiment, the polypeptide is expressed in a cell.

In another aspect, the present invention provides a method of screening for a compound that binds to a polypeptide of the invention, the method comprising using the structural coordinates of a crystal of the polypeptide to computationally evaluate a candidate compound for its ability to bind to the polypeptide.

Also provided is a compound identified using a method of the invention.

In a further aspect, the present invention provides a method of modulating an immune response in a subject, the method comprising administering to the subject a polypeptide of the invention, a polynucleotide of the invention, a vector of the invention, a host cell of the invention, a transgenic plant of the invention, an extract of the invention, a cell population of the invention, and/or a composition of the invention.

In one embodiment, the subject is administered with a DNA vaccine comprising a polynucleotide encoding a compound of the invention conjugated to an antigen, wherein upon administration to the subject the compound is produced and an immune response to the antigen is produced.

In another embodiment, a transgenic plant of the invention, or an extract thereof, is orally administered to the subject. Preferably, the transgenic plant or extract thereof comprises a compound of the invention conjugated to an antigen.

In another aspect, the present invention provides a method of modulating an immune response to an antigen in a subject, the method comprising exposing dendritic cells or precursors thereof in vitro to a polypeptide of the invention, a polynucleotide of the invention, a vector of the invention, a host cell of the invention, a transgenic plant of the invention, an extract of the invention, a cell population of the invention, and/or a composition of the invention, and administering said cells to the subject.

In yet another aspect, the present invention provides a method of treating and/or preventing a disease involving dendritic cells or precursors thereof, the method comprising administering to the subject a polypeptide of the invention, a polynucleotide of the invention, a vector of the invention, a host cell of the invention, a transgenic plant of the invention, an extract of the invention, a cell population of the invention, and/or a composition of the invention.

Also provided is the use of a polypeptide of the invention, a polynucleotide of the invention, a vector of the invention, a host cell of the invention, a transgenic plant of the invention, an extract of the invention, a cell population of the invention, and/or a composition of the invention for the manufacture of a medicament for modulating an immune response in a subject.

Also provided is the use of dendritic cells or precursors thereof exposed in vitro to a polypeptide of the invention, a polynucleotide of the invention, a vector of the invention, a host cell of the invention, a transgenic plant of the invention, an extract of the invention, a cell population of the invention, and/or a composition of the invention for the manufacture of a medicament for modulating an immune response to an antigen in a subject.

Also provided is the use of a polypeptide of the invention, a polynucleotide of the invention, a vector of the invention, a host cell of the invention, a transgenic plant of the invention, an extract of the invention, a cell population of the invention, and/or a composition of the invention for the manufacture of a medicament for treating and/or preventing a disease involving dendritic cells or precursors thereof in a subject.

In another aspect, the present invention provides a method of producing a compound of the invention, the method comprising administering to an animal a polypeptide of the invention, a polynucleotide of the invention, a vector of the invention, and/or a host cell of the invention.

Preferably, the method further comprises isolating an antibody from the animal which binds the polypeptide.

In an embodiment, the method further comprises fusing a cell from the animal which produces antibodies which bind the polypeptide with a myeloma tumor cell to produce a hybridoma.

In yet another embodiment, the present invention provides a kit comprising a compound of the invention, a cell line of the invention, a polypeptide of the invention, a polynucleotide of the invention, a vector of the invention, a host cell of the invention, a transgenic plant of the invention, an extract of the invention, a cell population of the invention and/or a composition of the invention.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

Figure 1:
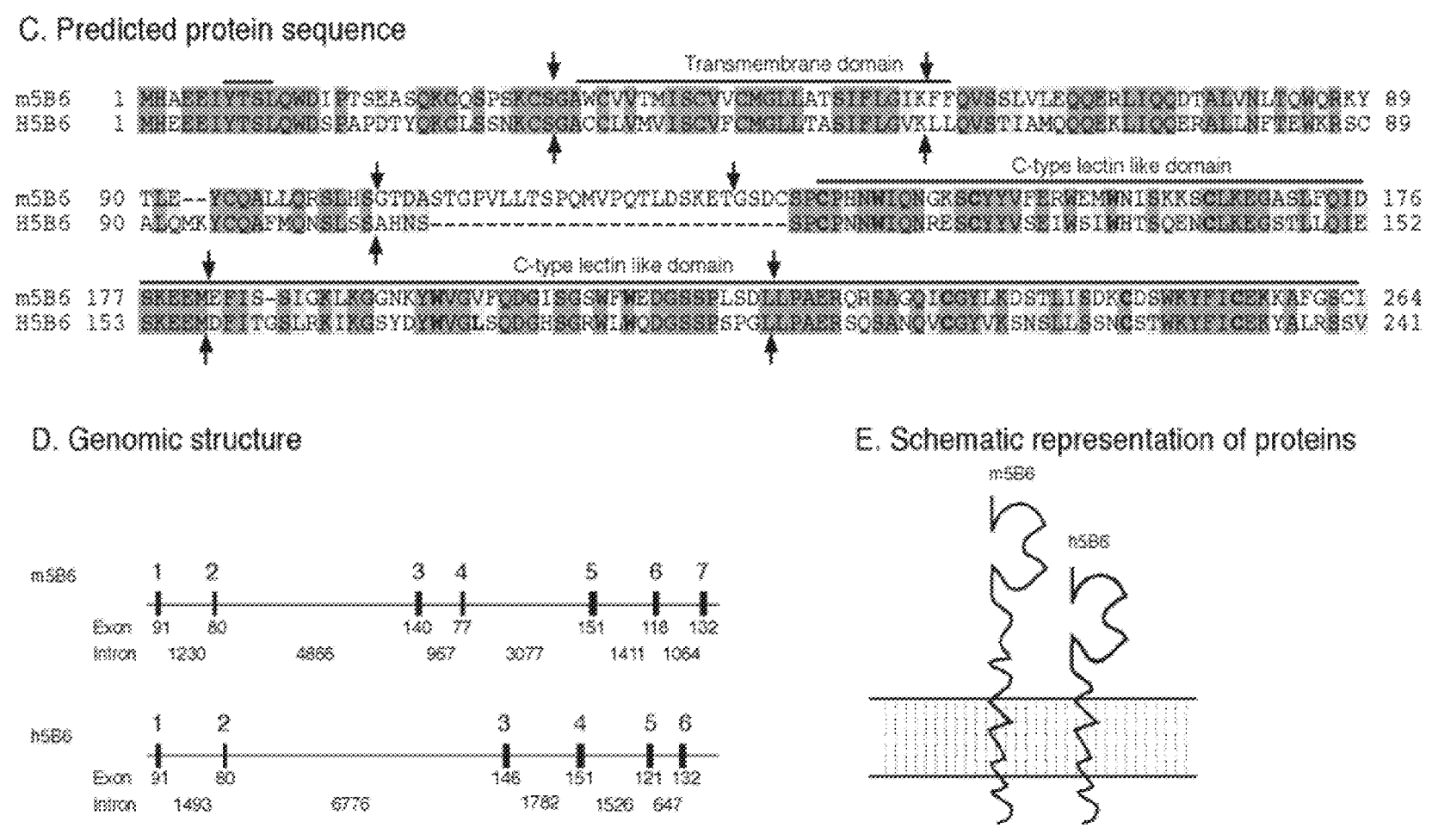

FIG. 1. The genomic structure and predicted protein structure encoded by the mouse (m) and human (h) 5B6 genes. The full-length cDNA encoding 5B6: (A) mouse cDNA (SEQ ID NO: 10) encoding mouse 5B6 and (B) human cDNA (SEQ ID NO: 9) encoding human 5B6. (C) Protein sequence alignment of the predicted protein sequence encoded by mouse and human 5B6; mouse 5B6 (m5B6) (SEQ ID NO: 2); human 5B6 (H5B6) (SEQ ID NO: 1). Sequence identity is highlighted in dark grey, similarity is shown in a light grey. Arrowheads denote exon boundaries. (D) Gene structures of mouse and human 5B6, determined by alignment of the cDNA to the genomic sequence databases of the C57BL/6J mouse (UCSC assembly February 2006) and human databases (UCSC assembly March 2006) respectively, are represented schematically. Exons encoding the coding region of 5B6 genes are denoted by black boxes and the size (bp) of the exons and introns are shown below. (E) A schematic representation of the mouse and human 5B6 proteins.

FIG. 2. Alignment of the CTLD of mouse (SEQ ID NO: 62) and human (SEQ ID NO: 63) 5B6 (Clec9A) to proteins that share sequence homology. Rat mannose binding protein A (MBP-A) (SEQ ID NO: 37) is included for comparison as a classical C-type lectin domain that has functional carbohydrate recognition domains. Partial sequence of mouse Clec12a (SEQ ID NO:32); partial sequence of mouse Dectin-1 (SEQ ID NO:33); partial sequence of mouse Clec8a (SEQ ID NO:34); partial sequence of mouse NKG2D (SEQ ID NO:35); and partial sequence of human NKG2D (SEQ ID NO:36) are depicted. Grey boxes indicate conserved residues, (+) indicates additional pair of cysteine residues that may be involved in protein homodimerization, (*) marks the conserved cysteine residues predicted to form disulfide bonds. The residues that ligate $Ca^{2+}$ in the MBP-A are designated 1 and 2.

Figure 3:
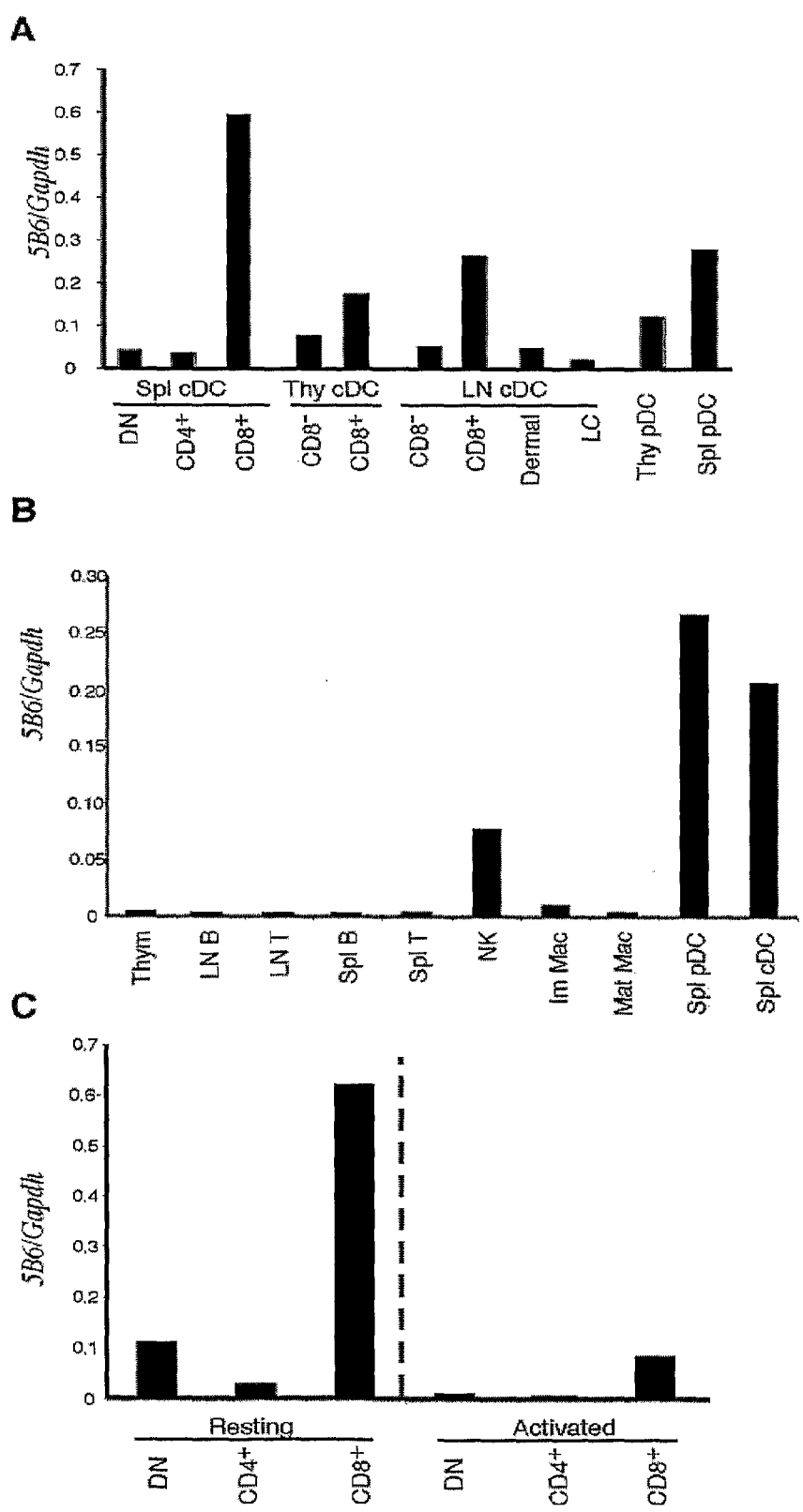

FIG. 3. Gene expression profiles of mouse 5B6. Real-time RT-PCR was used to study the expression profiles of the 5B6 gene relative to Gapdh in (A) lymphoid organ steady state DC including splenic cDC subsets; DN, $CD4^+$ and $CD8^+$, thymic cDC subsets; $CD8^-$ and $CD8^+$, LN cDC subsets;

CD8[−], CD8[+], Dermal and Langerhans' cells (LC) and in thymic and splenic pDC. (B) Haemopoietic cells including thymocytes (thym), lymph node (LN) B and T cells, spleen (spl) B and T cells, NK cells, immature macrophages (im mac), mature macrophages (mat mac), splenic pDC and cDC. (C) Splenic cDC isolated from both steady state (resting) mice and after 3 hours in vivo activation with LPS and CpG.

FIG. 4. Surface expression of m5B6 (Clec9A) protein on DCs and other hemopoietic cells. (A) The DCs were purified and surface labeled by 4-color immunofluorescent staining. DCs were stained with mAb against CD11c (N418-PeCy7), CD45RA (14.8-APC), CD8 (53-6.7-APC-Cy7) and m5B6 (10B4-biotin). Splenic DCs were also stained with CD4 (GK1.5-FITC), thymic DCs with Sirpα (p84-FITC), and subcutaneous LN DCs with CD205 (NLDC-145-FITC). Splenic cDCs were divided into CD4[+]cDCs (CD11c[hi]CD45RA[−]CD4[+]CD8[−]), DN cDCs (CD11c[hi]CD45RA[−]CD4[−]CD8[−]) and CD8[+]cDCs (CD11c[hi]CD45RA[−]CD8[+]CD4[−]); thymic cDCs were divided into CD8[−]cDCs(Sirpα[hi]CD8[lo]) and CD8[+]cDCs (Sirpα[lo]CD8[+]); and LN cDCs into CD8[−]cDC (CD11c[+]CD205[−]CD8[−]), dermal cDCs (CD11c[+]CD205[int]CD8[−]), Langerhans' cells (CD11c[+]CD205[hi]CD8[−]) and CD8[+]cDCs (CD11c[+]CD205[hi]CD8[+]), as described previously (Lahoud et al., 2006). pDCs were identified as CD11c[int]CD45RA[+]. Splenocytes were stained with mAb against CD3 (KT3-1.1-FITC), CD19 (1D3-PeCy7), NK1.1 (PK136-PeCy7), CD49b (Hmα2-APC) and B cells (CD19[+]CD3[−]), T cells (CD19[−]CD3[+]) and NK cells (NK1.1[+]CD49b[+]CD3[−]) were identified. Splenic macrophages were enriched as indicated in Materials and Methods and stained with CD11b (M1/70-Cy5) and F4/80-FITC and defined as CD11b[hi]F4/80[+]. Bone marrow cells and splenocytes were stained with mAb against CD11b (M1/70-Cy5) and Ly6C (5075-3.6-FITC) and monocytes were defined as side-scatter[lo]Ly6C[hi]CD11b[hi]. Bone marrow macrophages were Ly6C[int]CD11b[hi]. Cell populations were counterstained with SA-PE and analysed for m5B6 expression. The solid line represents m5B6 staining on gated cells, the dotted line represents staining of the gated cells with an isotype-matched control. (B) Enriched preparations of splenic DCs were stained with mAb against m5B6 (10B4-biotin), CD11c (N418-Quantum dot 655), CD8α (YTS-169-PercpCy5.5 and CD24 (M1/69-Alexa 633) and 120G8-FITC, then counterstained with SA-PE. pDCs (CD11c[int]120G8[+]) and cDCs (CD11c[hi]120G8[−]) were analysed for expression of m5B6. m5B6 expression correlated with CD8α and CD24 expression on cDCs. Most splenic pDCs expressed m5B6. (C) An enriched preparation of blood DCs was stained in parallel with the splenic DCs (B) using the same mAbs and analysed using identical gating strategies. Blood DCs do not express CD8α, but do express CD24. Similar to splenic DCs, blood DCs expressing CD24 also co-expressed 5B6 pDCs from the blood, like their splenic counterpart, expressed m5B6.

Figure 5:
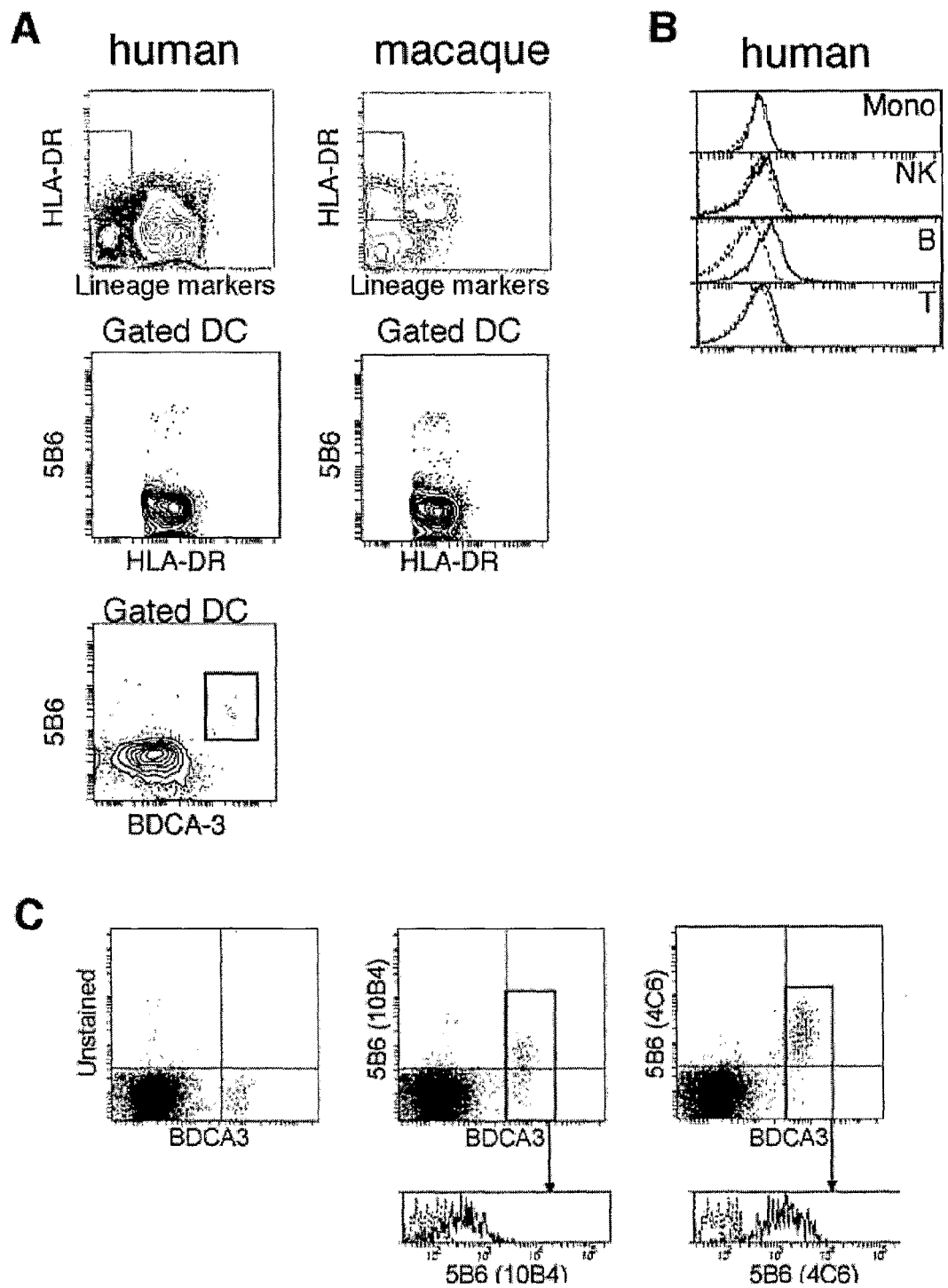

FIG. 5. Expression of 5B6 (CLEC9A) on human and macaque DC and haemopoietic cells. (A) Human and macaque peripheral blood mononuclear cells (PBMCs) were isolated and surface immunofluorescence labeled with mAb against HLADR, BDCA3, 5B6, and a PE-conjugated Lineage cocktail including CD3 (T cells), CD14 (monocytes), CD19 (B cells) and CD56 (Natural killer cells). Blood DC were gated as HLADR[+]Lineage (PE)[−] and further analysed for their expression of 5B6 (human and macaque) and BDCA3 (human). (B) Human PBMC were surface immunofluorescence labeled with mAb against the required surface markers and 5B6. Monocytes (CD14[+]), NK cells (NKp46[+]), T cells (CD3[+]), and B cells (CD19[+]) were gated and analysed for their expression of 5B6 (solid line). The dotted line represents staining of the gated cells with an isotype matched control. (C) Expression of 5B6 on human blood DCs. Human peripheral blood mononuclear cells (PBMCs) were isolated and depleted of monocytes, B cells and T cells using a cocktail of mouse anti-human antibodies (FMC17 (CD14), FMC63 and B1 (CD19 and CD20) and BC3 (CD3)) followed by removal with anti-mouse magnetic beads (Biomag). The enriched preparation of cells were surface immunofluorescence labeled with mAbs against HLADR (L243-APCCy7), 5B6 (10B4-APC or 4C6-APC), and BDCA-3 (AD5-14H12-FITC). Blood DCs were gated as HLADR[+] and further analysed for their expression of BDCA3 and 5B6. The dotted line represents the background staining of the gated cells.

Figure 6:
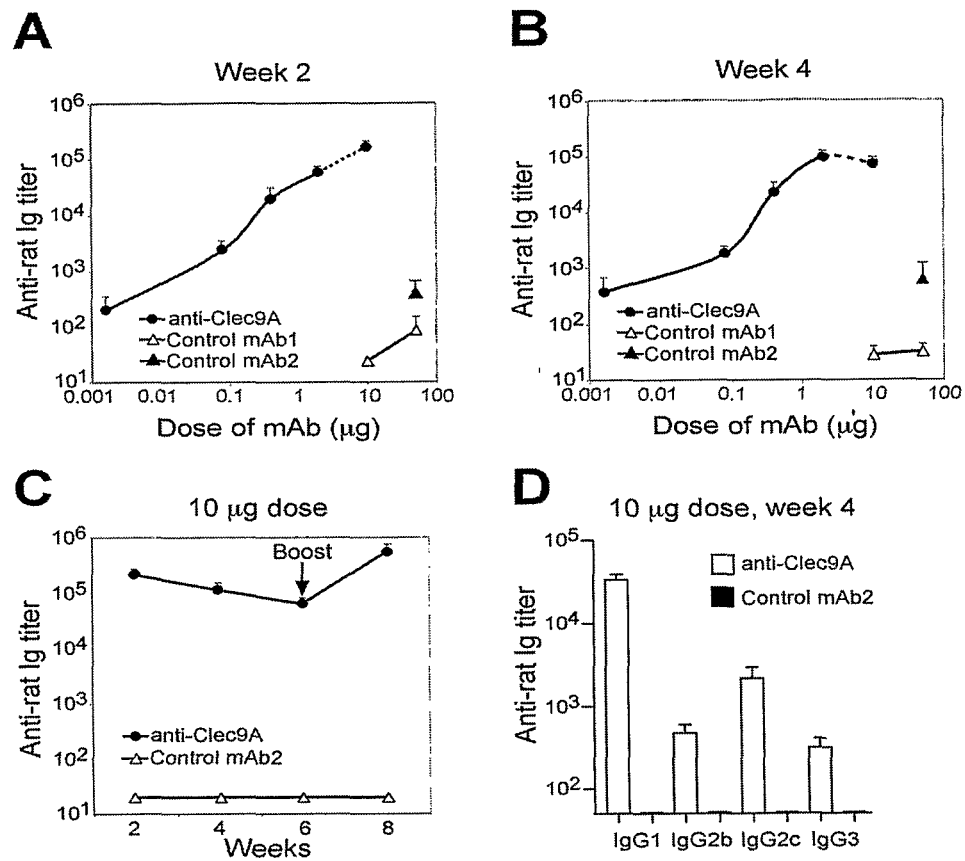

FIG. 6. Targeting DC using anti-m5B6 mAb 10B4 (referred to in the Figure as anti-Clec9A) induces potent humoral responses. (A, B) Mice were injected i.v. with either 2 μg (n=5), 0.4 μg (n=5), 0.08 μg (n=5), or 0.016 μg (n=4) of anti-m5B6 mAb (10B4) or with 50 μg (n=5), and 10 μg (n=5) of an non-targeting isotype control mAb-1 (eBioscience), or with 50 μg (n=2) of an in-house isotype control mAb-2 (GL117). Serum anti-rat Ig reactivity was measured by ELISA on (A) week 2 and (B) week 4. Mean titers+/−SEM are depicted. The titration experiment was performed twice and one representative experiment is shown. The 10 μg dose response represents the cumulative data of 5 experiments (week 2; n=20, week 4; n=19). (C) Mice (n=5) were injected i.v. with either 10 μg of anti-m5B6 mAb or non-targeting isotype control mAb-1 (eBioscience). Serum samples were collected on week 2, 4, and 6, after which mice were injected with 10 μg of non-targeting isotype control mAb-2 (GL117). Serum anti-rat Ig reactivity was measured by ELISA on week 2, 4, 6, 8 and is presented as mean titers+/− SEM. (D) Mice were injected i.v. with either 10 μg of anti-m5B6 mAb (n=7) or non-targeting isotype control mAb-2 (GL117; n=4). The isotype of the serum anti-rat Ig reactivity was measured by ELISA on week 4. Bar graphs depict mean titers+/−SEM. The experiments were performed twice and representative data is presented.

FIG. 7. The nature of the humoral immunity induced by targeting DC using anti-m5B6 mAb 10B4 (referred to in the Figure as anti-Clec9A). C57BL/6 or (A) C57BL/6 TRIF[−/−] MyD88[−/−] or (B) C57/BL6 FcRγ[−/−] or (C) C57/BL6 nu/nu mice were injected i.v. with 10 μg of the anti-m5B6 mAb (10B4) or the non-targeted isotype control mAb-2 (GL117). (D) C57BL/6 mice were injected i.v. with 10 μg of the anti-m5B6 mAb or isotype control mAb-2 (GL117), either with or without LPS (10 ng). (E) Ten μg of OVA-conjugated anti-m5B6 mAb or OVA-conjugated isotype control mAb-2 (GL117) or (F) escalating doses of free OVA were injected i.v. into C57BL/6 mice. Serum anti-rat Ig Ab titers were measured by ELISA at week 4. Each circle represents an individual mouse, the geometric mean of the group is depicted by a line. Experiments were performed 2-4 times with similar results, with the exceptions of (C) and (E) which were performed once.

Figure 8:
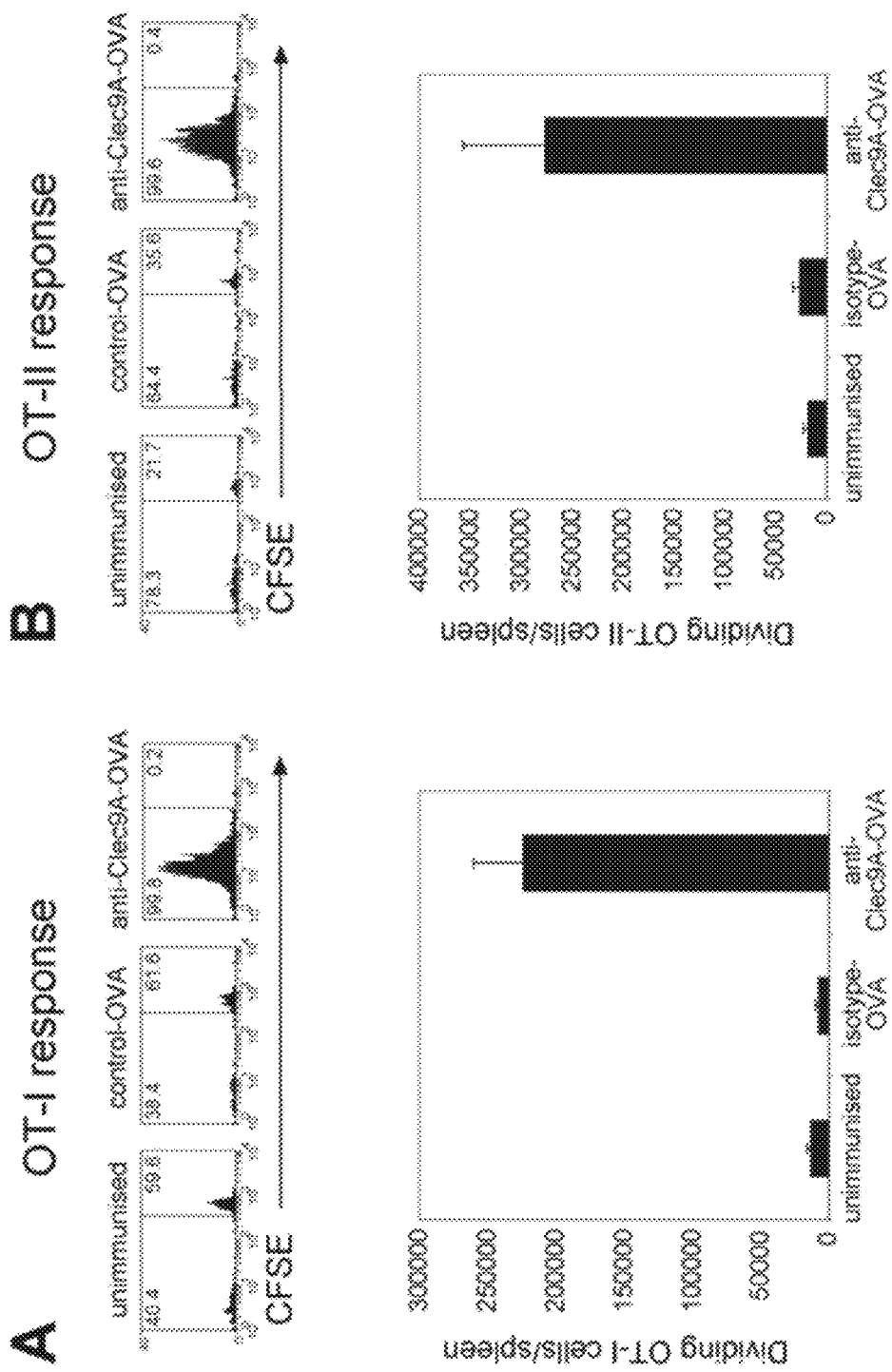

FIG. 8. Targeting Ag to DC using anti-m5B6-OVA 10B4 (referred to in the Figure as anti-Clec9A-OVA) elicits both CD4 and CD8 T cell proliferative responses. OVA-specific transgenic CD8 (OT-I) or CD4 (OT-II) T cells (10[6]) were adoptively transferred into naïve C57/BL6 Ly5.1 mice. One day later mice were injected i.v. with 2.5 μg of anti-m5B6-OVA (n=3) or non-targeted isotype control-OVA mAb-2 (GL117; n=3), or left unimmunised (n=2). Three days post-mAb injection, mice were sacrificed and spleens harvested.

Cells were stained with mAb against Ly5.2 (S.450-15.2-PE) and CD4 (GK1.5-APC) or CD8 (YTS169-APC) and proliferating CFSE-labelled transgenic T cells, (A) OT-I (Ly5.2$^+$CD8$^+$) or (B) OT-II (Ly5.2$^+$CD4$^+$), enumerated by flow cytometry. The proliferative response of OVA-specific T cells was seen as a loss of CFSE fluorescence by flow cytometry. The total number of OT-I cells and OT-II cells proliferating per spleen was enumerated as described in Materials and Methods and data is presented +/−SEM. The experiment was performed twice with 2.5 µg and once with 5 µg of OVA-conjugated mAb, with similar results.

Figure 9:
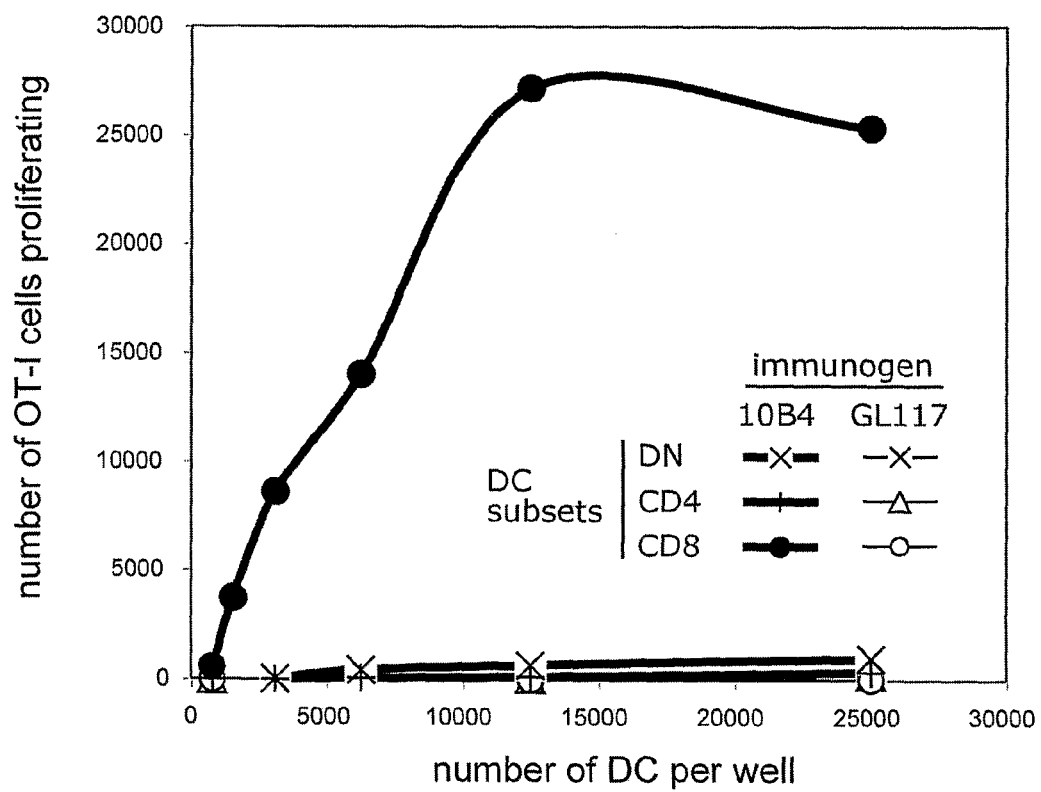

FIG. 9. Injection of mice with anti-m5B6-Ova (referred to in the figure as 10B4) 10B4-OVA conjugate delivered Ag to CD8$^+$ DCs and primed OVA specific CD8 T cells. Three mice were immunised subcutaneously with either 10 µg of OVA-conjugated 10B4 (anti-5B6 mAb) or OVA-conjugated isotype control mAb (GL117). One day later, mice were sacrificed, DC isolated from spleens, and sorted by flow cytometry into CD8$^+$, CD4$^+$ or CD4$^-$CD8$^-$ (DN) DC subsets. Graded doses of DC were incubated with CFSE-labelled OT-I cells and cultured for three days. Proliferating OT-I cells were enumerated by flow cytometry. Only the CD8$^+$ DC targeted with the 5B6 specific mAb induced significant OT-I cell proliferation. Data is representative of two independent experiments.

Figure 10:
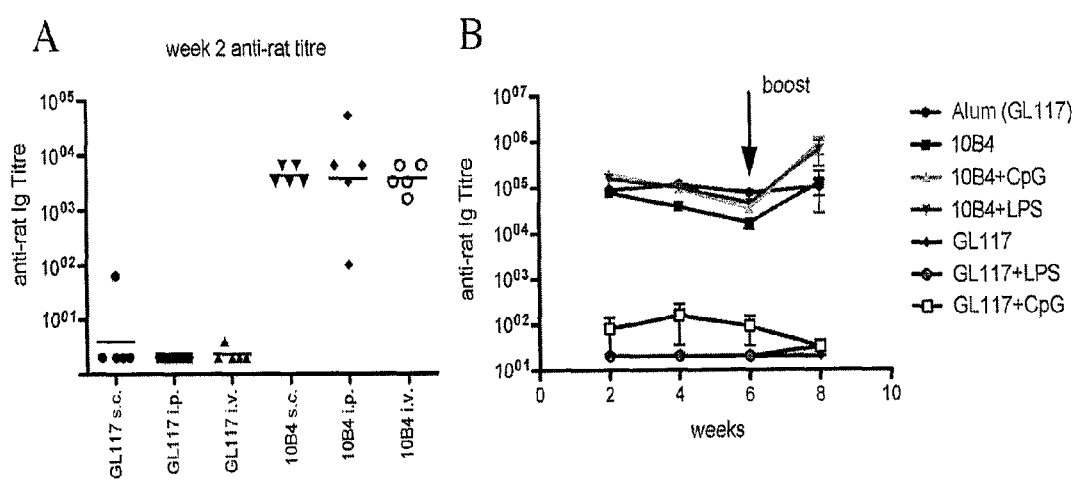

FIG. 10. Anti-5B6 Ab (10B4) is highly effective at antigen delivery via different routes of administration and in the presence or absence of adjuvants. (A). 10B4 antibody induces strong humoral responses via different routes of administration. Groups of C57/BL6 mice (n=5) were injected i.v., s.c., or i.p. with 10 µg of 10B4 mAb or isotype control mAb (GL117). Serum samples were collected 2 weeks and serum anti-rat Ig reactivity was quantitated by ELISA. (B). 10B4 antibody induces strong humoral responses with or without adjuvants. Groups of C57/BL6 mice (n=5) were injected i.v. with 2 µg of 10B4 mAb or isotype control mAb (GL117) in the absence or presence of LPS (1 µg) or CpG (10 µg). Positive control mice were injected i.p. with GL117 and Alum. Serum samples were obtained 2, 4, and 6 weeks after initial injection. Mice were then boosted i.v. with 10 µg of isotype control mAb (GL117) and a serum sample was taken two weeks later. The serum anti-rat Ig reactivity was quantitated by ELISA.

FIG. 11. Soluble fragments of 5B6 bind to membrane bound 5B6. (A). Amino acid sequence of the soluble proteins generated for mouse and human 5B6. Two constructs were generated for each of mouse 5B6 and human 5B6, the original construct which includes both the stalk and the C-type lectin like domain, and the soluble protein-2/3 construct which includes the C-type lectin-like domain but does not include the stalk region. In the figure, the IL3 leader sequence is italicised and single underlined, the biotinylation consensus sequence is italicised and double underlined, the FLAG tag is italicised and underlined with a wavy line. The 5B6 sequences are shown in red. (B). Soluble 5B6 binds to membrane bound 5B6 on transiently transfected 293T cells. 293T cells were transiently transfected with expression constructs encoding full length untagged m5B6 (293T-m5B6), h5B6 (293T-h5B6) or no DNA (293T) to generate transfectant cells expressing membrane bound m5B6 or h5B6. Two days later, cells were harvested and surface immunofluorescence labeled using soluble FLAG-tagged m5B6 and h5B6 (with stalk—from original construct) and soluble FLAG-tagged Cire. Binding was detected using biotinylated anti-Flag mAb 9H10 and Streptavidin PE. Live cells were gated on forward scatter and propidium iodide exclusion and analysed for their surface binding of soluble 5B6 (solid line) relative to control staining with anti-Flag Ab and streptavidin-PE (dashed line). (C). Binding of soluble 5B6 to membrane bound 5B6 is independent of stalk. CHO cells, untransfected or stably transfected with expression constructs encoding full length untagged membrane bound m5B6 (CHO-m5B6), were surface immunofluorescence labeled using biotinylated soluble FLAG-tagged m5B6 and h5B6 (with or without stalk, as indicated) and biotinylated soluble FLAG-tagged Cire. Binding was detected using Streptavidin PE. Live cells were gated on forward scatter and analysed for their surface binding of biotinylated soluble 5B6 (solid line) relative to control staining with streptavidin-PE (dashed line).

Figure 12:
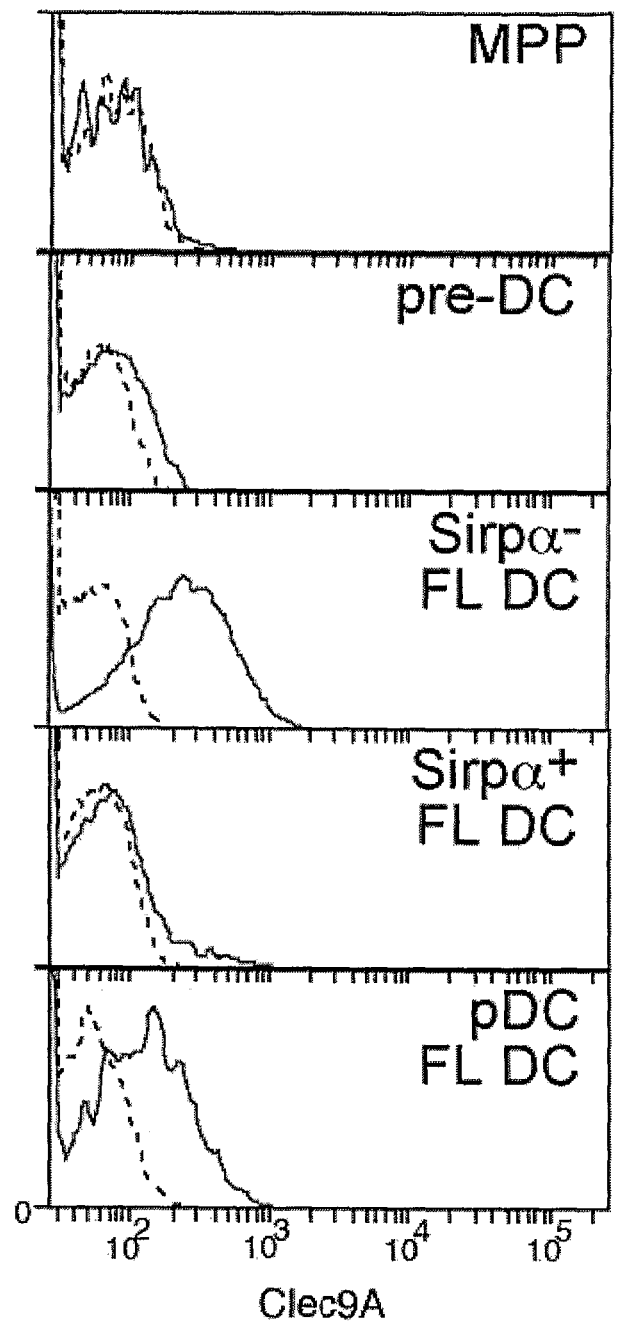

FIG. 12. DC precursors or Flt3 ligand generated DC (FL DC) were isolated as described. Multipotent progenitors (MPP) were defined as lin$^-$CD117$^+$ sca-1$^+$CD34$^+$. In vitro generated Pre-DC were defined as CFSE$^{low}$ lin$^-$ CD11c$^+$ cells from culture. FL DC were defined as follows; pDC were gated as CD11c$^+$CD45RA$^+$; Sirpα$^+$ cDC as CD11c$^+$CD45RA$^-$Sirpα$^+$ and Sirpα$^-$ cDC as CD11c$^+$CD45RA$^-$Sirpα$^-$. The level of background staining (indicated by a broken line) was determined by the fluorescence intensity of cells stained with the antibodies required to define the cell populations. 5B6 expression (indicated by the solid line) was determined by staining with the above mentioned antibodies, as well as an antibody against 5B6 (10B4-APC).

Figure 13:
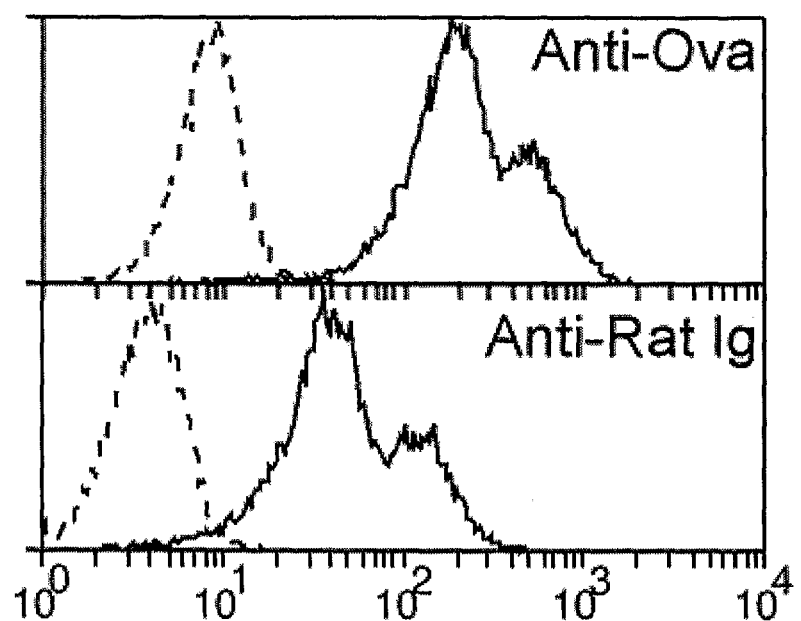

FIG. 13. Generation of recombinant anti-Clec9A-Ova (anti-5B6-Ova) using genetic fusion. Recombinant anti-Clec9A (5B6) Ab 10B4 was generated by transient transfection of plasmids encoding the 10B4 kappa chain and the 10B4-heavy chain fused to Ova into freestyle 293 F cells. After 48 h, supernatant was harvested from the transient transfection and the capacity of the anti-5B6-Ova Ab to recognise 5B6 examined by immunofluorescence labeling of CHO-5B6 transfectant cells with the recombinant Ab (from the 293F transient transfection) and flow cytometric analysis. CHO cells stably expressing full length membrane bound 5B6 were incubated with the transfection supernatant (containing recombinant anti-Clec9A-OvaAb) and binding detected using biotinylated anti-ova Ab and streptavidin-PE (top panel) or anti-rat Ig PE (bottom panel). The solid line indicates staining of CHO-5B6 cells with the recombinant anti-Clec9A-Ova Ab (transfection supernatant), the dashed line indicates staining of CHO-5B6 cells with secondary Ab (anti-Ova-Biotin and streptavidin-PE for the top panel, and anti-rat Ig PE for the bottom panel).

KEY TO THE SEQUENCE LISTING

SEQ ID NO:1—Human 5B6.
SEQ ID NO:2—Murine 5B6.
SEQ ID NO:3—Chimpanzee 5B6.
SEQ ID NO:4—Rhesus monkey 5B6.
SEQ ID NO:5—Dog 5B6.
SEQ ID NO:6—Cow 5B6.
SEQ ID NO:7—Horse 5B6.
SEQ ID NO:8—Rat 5B6.
SEQ ID NO:9—Open reading frame encoding human 5B6.
SEQ ID NO:10—Open reading frame encoding murine 5B6.
SEQ ID NO:11—Open reading frame encoding chimpanzee 5B6.
SEQ ID NO:12—Open reading frame encoding rhesus monkey 5B6.
SEQ ID NO:13—Open reading frame encoding dog 5B6.
SEQ ID NO:14—Open reading frame encoding cow 5B6.
SEQ ID NO:15—Open reading frame encoding horse 5B6.
SEQ ID NO:16—Open reading frame encoding rat 5B6.

SEQ ID NO's 17 to 28—Oligonucleotide primers.
SEQ ID NO:29—Antigenic fragment of murine 5B6.
SEQ ID NO:30—Antigenic fragment of human 5B6.
SEQ ID NO:31—Biotinylation consensus sequence.
SEQ ID NO:32—Partial sequence of mouse Clec12a.
SEQ ID NO:33—Partial sequence of mouse Dectin-1.
SEQ ID NO:34—Partial sequence of mouse Clec8a.
SEQ ID NO:35—Partial sequence of mouse NKG2D.
SEQ ID NO:36—Partial sequence of human NKG2D.
SEQ ID NO:37—Partial sequence of rat MBP-A.
SEQ ID NO:38—Soluble flag tagged mouse 5B6 including stalk.
SEQ ID NO:39—Soluble flag tagged human 5B6 including stalk.
SEQ ID NO:40—Soluble flag tagged mouse 5B6 without stalk.
SEQ ID NO:41—Soluble flag tagged human 5B6 without stalk.
SEQ ID NO:42—Amino acid sequence of heavy chain of 10B4 anti-5B6 antibody.
SEQ ID NO:43—Amino acid sequence of variable region of heavy chain of 10B4 anti-5B6 antibody.
SEQ ID NO:44—Amino acid sequence of CDR1 of heavy chain of 10B4 anti-5B6 antibody.
SEQ ID NO:45—Amino acid sequence of CDR2 of heavy chain of 10B4 anti-5B6 antibody.
SEQ ID NO:46—Amino acid sequence of CDR3 of heavy chain of 10B4 anti-5B6 antibody.
SEQ ID NO:47—Amino acid sequence of light chain of 10B4 anti-5B6 antibody.
SEQ ID NO:48—Amino acid sequence of variable region of light chain of 10B4 anti-5B6 antibody.
SEQ ID NO:49—Amino acid sequence of CDR1 of light chain of 10B4 anti-5B6 antibody.
SEQ ID NO:50—Amino acid sequence of CDR2 of light chain of 10B4 anti-5B6 antibody.
SEQ ID NO:51—Amino acid sequence of CDR3 of light chain of 10B4 anti-5B6 antibody.
SEQ ID NO's 52 to 57—Oligonucleotide primers.
SEQ ID NO:58—Soluble mouse 5B6 including stalk.
SEQ ID NO:59—Soluble human 5B6 including stalk.
SEQ ID NO:60—Soluble mouse 5B6 without stalk.
SEQ ID NO:61—Soluble human 5B6 without stalk.
SEQ ID NO:62—CTLD of mouse 5B6.
SEQ ID NO:63—CTLD of human 5B6.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, molecular biology, dendritic cell biology, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

As used herein, the term "5B6" refers to a polypeptide which comprises an amino acid sequence as provided in any one or more of SEQ ID NO's 1 to 8, orthologs thereof from other species, functional variants or mutants thereof, as well as biologically active and/or antigenic fragments thereof. The terms "5B6" and "CLEC9A" are used interchangeably herein.

As used herein, the term "C-type lectin-like domain" or "CTLD" refers to a protein domain family which has been identified in a number of proteins isolated from many animal species, see for example, review by Drickamer (1999). Initially, the CTLD domain was identified as a domain common to the so-called C-type lectins (calcium-dependent carbohydrate binding proteins) and named "Carbohydrate Recognition Domain" ("CRD"). More recently, it has become evident that this domain is shared among many eukaryotic proteins, of which several do not bind sugar moieties, and hence, the canonical domain has been named as CTLD. CTLDs have been reported to bind a wide diversity of compounds, including carbohydrates, lipids and proteins. The CTLD consists of approximately 120 amino acid residues and, characteristically, contains two or three intra-chain disulfide bridges. Although the similarity at the amino acid sequence level between CTLDs from different proteins is relatively low, the 3D-structures of a number of CTLDs have been found to be highly conserved, with the structural variability essentially confined to a so-called loop-region, often defined by up to five loops. An example of a CTLD of a polypeptide of the present invention is highlighted in FIG. 1C.

As used herein, the terms "treating", "treat" or "treatment" include administering a therapeutically effective amount of a compound of the invention, polypeptide of the invention, polynucleotide of the invention etc sufficient to reduce or eliminate at least one symptom of the specified condition.

As used herein, the terms "preventing", "prevent" or "prevention" include administering a therapeutically effective amount of a compound of the invention, polypeptide of the invention, polynucleotide of the invention etc sufficient to stop or hinder the development of at least one symptom of the specified condition.

As used herein, the "sample" can be any biological material suspected of comprising dendritic cells or precursors thereof. Examples include, but are not limited to, blood, for example, whole peripheral blood, cord blood, foetus blood, bone marrow, plasma, serum, urine, cultured cells, saliva or urethral swab, lymphoid tissues, for example tonsils, peyers patches, appendix, thymus, spleen and lymph nodes. The sample may be tested directly or may require some form of treatment prior to testing. For example, a biopsy sample may require homogenization to produce a cell suspension prior to testing. Furthermore, to the extent that the biological sample is not in liquid form (for example, it may be a solid, semi-solid or a dehydrated liquid sample), it may require the addition of a reagent, such as a buffer, to mobilize the sample. The mobilizing reagent may be mixed with the sample prior to placing the sample in contact with, for example, a compound of the invention.

As used herein, the term "immune response" refers to an alteration in the reactivity of the immune system of a subject in response to an antigen and may involve antibody production, induction of cell-mediated immunity, complement activation and/or development of immunological tolerance.

As used herein, the terms "conjugate", "conjugated" or variations thereof are used broadly to refer to any form to covalent or non-covalent association between a compound of the invention and a therapeutic agent, or to placing a compound of the invention and a therapeutic agent in close proximity to each other such as in a liposome. In one embodiment, a conjugated compound of the invention is produced by the expression of a polynucleotide comprising a single open reading frame encoding the conjugated compound, for example a single open reading frame encoding the heavy or light chain of an antibody C- and/or N-terminally fused to an antigen.

As used herein, the term "extract" refers to any portion of a host cell, plant or non-human transgenic animal of the invention. The portion may be a whole entity such as a seed of a plant, or obtained by at least partial homogenization and/or purification. This term includes portions secreted from the host cell, and hence encompasses culture supernatants.

Compounds

The present inventors have now shown, for the first time, that 5B6 (also referred to in the art as CLEC9A and HEEE9341) is expressed in a subset of dendritic cells and or precursors thereof. This enables compounds which bind 5B6 to be used in a wide variety of diagnostic and therapeutic procedures. For example, antibody-antigen conjugates can be used to deliver the antigen to dendritic cells and/or precursors thereof to induce an immune response. In another example, detectably labelled compounds can be used to detect dendritic cells or precursors thereof in a sample. In a further example, antibody-cytotoxic agent conjugates can be used to target deleterious dendritic cells or precursors thereof.

Compounds of the invention can be any type of molecule that binds, preferably which specifically binds, 5B6. The compound may be, for example, a purified and/or recombinant naturally occurring ligand or a synthetic ligand. The binding between a compound and 5B6 may be mediated by covalent or non-covalent interactions or a combination of covalent and non-covalent interactions. When the interaction of the compound and 5B6 produces a non-covalently bound complex, the binding which occurs is typically electrostatic, hydrogen-bonding, or the result of hydrophilic/lipophilic interactions. In a preferred embodiment, the compound is a purified and/or recombinant polypeptide. Particularly preferred 5B6 binding compounds are purified and/or recombinant anti-5B6 antibodies or antigenic binding fragments thereof.

Although not essential, the compound may bind specifically to 5B6. The phrase "specifically binds", means that under particular conditions, the compound binds 5B6 and does not bind to a significant amount to other, for example, proteins or carbohydrates. Preferably, the compound specifically binds 5B6 and not other molecules in a sample obtained from a subject comprising dendritic cells or precursors thereof. Specific binding to 5B6 under such conditions may require an antibody that is selected for its specificity. In another embodiment, a compound is considered to "specifically binds" to 5B6 if there is a greater than 10 fold difference, and preferably a 25, 50 or 100 fold greater difference between the binding of the compound to 5B6 when compared to another protein, especially a protein comprising a CTLD.

Antibodies

The terms "antibodies" and "immunoglobulin" refers to a class of structurally related glycoproteins consisting of two pairs of polypeptide chains, one pair of light (L) low molecular weight chains and one pair of heavy (H) chains, all four inter-connected by disulfide bonds. The structure of immunoglobulins has been well characterized, see for instance Fundamental Immunology Ch. 7 (Paul, W., ed., 2nd ed. Raven Press, N.Y. (1989)). Briefly, each heavy chain typically is comprised of a heavy chain variable region (abbreviated herein as $V_H$) and a heavy chain constant region (abbreviated herein as $C_H$). The heavy chain constant region typically is comprised of three domains, $C_H1$, $C_H2$, and $C_H3$. Each light chain typically is comprised of a light chain variable region (abbreviated herein as $V_L$) and a light chain constant region (abbreviated herein as $C_L$). The light chain constant region typically is comprised of one domain, $C_L$. The $V_H$ and $V_L$ regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs).

Each $V_H$ and $V_L$ is typically composed of three CDRs and four FRs, arranged from amino-terminus to carboxy-terminus in the following order: FR1, CDR1, FR2, CDR2, FR3, CDR3, FR4 (see also Chothia and Lesk, 1987). Typically, the numbering of amino acid residues in this region is performed by the method described in Kabat et al., Sequences of Proteins of Immunological Interest, 5th Ed. Public Health Service, National Institutes of Health, Bethesda, Md. (1991) (phrases such as variable domain residue numbering as in Kabat or according to Kabat herein refer to this numbering system for heavy chain variable domains or light chain variable domains). Using this numbering system, the actual linear amino acid sequence of a peptide may contain fewer or additional amino acids corresponding to a shortening of, or insertion into, a FR or CDR of the variable domain.

The term "humanized antibody", as used herein, refers to herein an antibody derived from a non-human antibody, typically murine, that retains or substantially retains the antigen-binding properties of the parent antibody but which is less immunogenic in humans.

The term complementarity determining region (CDR), as used herein, refers to amino acid sequences which together define the binding affinity and specificity of a variable fragment (Fv) region of a immunoglobulin binding site.

The term framework region (FR), as used herein, refers to amino acid sequences interposed between CDRs. These portions of the antibody serve to hold the CDRs in appropriate orientation (allows for CDRs to bind antigen). A variable region, either light or heavy, comprises a framework and typically three CDRs.

The term constant region (CR) as used herein, refers to the portion of the antibody molecule which confers effector functions. The constant regions of the subject humanized antibodies are derived from human immunoglobulins. The heavy chain constant region can be selected from any of the five isotypes: alpha, delta, epsilon, gamma or mu. Further, heavy chains of various subclasses (such as the IgG subclasses of heavy chains) are responsible for different effector functions and thus, by choosing the desired heavy chain constant region, antibodies with desired effector function can be produced. Preferred heavy chain constant regions are gamma 1 (IgG1), gamma 2 (IgG2), gamma 3 (IgG3) and gamma 4 (IgG4), more preferably gamma 4 (IgG4). The light chain constant region can be of the kappa or lambda type, preferably of the kappa type.

Antibodies may exist as intact immunoglobulins, or as modifications in a variety of forms including, for example, but not limited to, domain antibodies including either the VH or VL domain, a dimer of the heavy chain variable region (VHH, as described for a camelid), a dimer of the light chain variable region (VLL), Fv fragments containing only the light and heavy chain variable regions, or Fd fragments containing the heavy chain variable region and the CH1 domain. A scFv consisting of the variable regions of the heavy and light chains linked together to form a single-chain antibody (Bird et al., 1988; Huston et al., 1988) and oligomers of scFvs such as diabodies and triabodies are also encompassed by the term "antibody". Also encompassed are fragments of antibodies such as Fab, (Fab')$_2$ and FabFc$_2$ fragments which contain the variable regions and parts of the constant regions. CDR-grafted antibody fragments and oligomers of antibody fragments are also encompassed. The heavy and light chain components of an Fv may be derived from the same antibody or different antibodies thereby producing a chimeric Fv region. The antibody may be of animal (for example mouse, rabbit or rat) or human origin or may be chimeric (Morrison et al., 1984) or humanized (Jones et al., 1986), and UK 8707252). As used herein the term "antibody" includes these various forms. Using the guidelines provided herein and those methods well known to those skilled in the art which are described in the references cited above and in such publications as Harlow & Lane (supra) the antibodies for use in the methods of the present invention can be readily made.

Antibodies or antigen binding fragments of the invention which are not from a natural source, such as a humanized antibody, preferably retain a significant proportion of the binding properties of the parent antibody, for example of 24/04-10B4, 42/04-42D2, 20/05-3A4 and/or 23/05-4C6. In particular, such antibodies or fragments of the invention retain the ability to specifically bind the antigen recognized by the parent antibody used to produce the antibody or fragment such as a humanized antibody. Preferably, the antibody or fragment exhibits the same or substantially the same antigen-binding affinity and avidity as the parent antibody. Ideally, the affinity of the antibody or fragment will not be less than 10% of the parent antibody affinity, more preferably not less than about 30%, and most preferably the affinity will not be less than 50% of the parent antibody. Methods for assaying antigen-binding affinity are well known in the art and include half-maximal binding assays, competition assays, and Scatchard analysis.

A variety of immunoassay formats may be used to select antibodies or fragments that are specifically immunoreactive with 5B6. For example, surface labelling and flow cytometric analysis or solid-phase ELISA immunoassays are routinely used to select antibodies specifically immunoreactive with a protein or carbohydrate. See Harlow & Lane (supra) for a description of immunoassay formats and conditions that can be used to determine specific immunoreactivity.

The 5B6-binding antibodies may be Fv regions comprising a variable light (V$_L$) and a variable heavy (V$_H$) chain. The light and heavy chains may be joined directly or through a linker. As used herein a linker refers to a molecule that is covalently linked to the light and heavy chain and provides enough spacing and flexibility between the two chains such that they are able to achieve a conformation in which they are capable of specifically binding the epitope to which they are directed. Protein linkers are particularly preferred as they may be expressed as an intrinsic component of the Ig portion of the fusion polypeptide.

In another embodiment, recombinantly produced single chain scFv antibody, preferably a humanized scFv, is used in the methods of the invention.

Monoclonal Antibodies

Monoclonal antibodies directed against 5B6 epitopes can be readily produced by one skilled in the art. An example of a method for producing such antibodies using the 5B6 epitope RWLWQDGSSPSPGLLPAERSQSANQVC-OH) (SEQ ID NO:30) is provided in the Examples section.

The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against 5B6 epitopes can be screened for various properties; i.e. for isotype and epitope affinity.

Animal-derived monoclonal antibodies can be used for both direct in vivo and extracorporeal immunotherapy. However, it has been observed that when, for example, mouse-derived monoclonal antibodies are used in humans as therapeutic agents, the patient produces human anti-mouse antibodies. Thus, animal-derived monoclonal antibodies are not preferred for therapy, especially for long term use. With established genetic engineering techniques it is possible, however, to create chimeric or humanized antibodies that have animal-derived and human-derived portions. The animal can be, for example, a mouse or other rodent such as a rat.

If the variable region of the chimeric antibody is, for example, mouse-derived while the constant region is human-derived, the chimeric antibody will generally be less immunogenic than a "pure" mouse-derived monoclonal antibody. These chimeric antibodies would likely be more suited for therapeutic use, should it turn out that "pure" mouse-derived antibodies are unsuitable.

Methodologies for generating chimeric antibodies are available to those in the art. For example, the light and heavy chains can be expressed separately, using, for example, immunoglobulin light chain and immunoglobulin heavy chains in separate plasmids. These can then be purified and assembled in vitro into complete antibodies; methodologies for accomplishing such assembly have been described (see, for example, Sun et al., 1986). Such a DNA construct may comprise DNA encoding functionally rearranged genes for the variable region of a light or heavy chain of an anti-5B6 antibody linked to DNA encoding a human constant region. Lymphoid cells such as myelomas or hybridomas transfected with the DNA constructs for light and heavy chain can express and assemble the antibody chains.

In vitro reaction parameters for the formation of IgG antibodies from reduced isolated light and heavy chains have also been described. Co-expression of light and heavy chains in the same cells to achieve intracellular association and linkage of heavy and light chains into complete H2L2 IgG antibodies is also possible. Such co-expression can be accomplished using either the same or different plasmids in the same host cell.

In another preferred embodiment of the present invention the anti-5B6 antibody is humanized, that is, an antibody produced by molecular modeling techniques wherein the human content of the antibody is maximised while causing little or no loss of binding affinity attributable to the variable region of, for example, a parental rat, rabbit or murine antibody.

The methods described below are applicable to the humanisation of anti-5B6 antibodies.

There are several factors to consider in deciding which human antibody sequence to use during the humanisation. The humanisation of light and heavy chains are considered independently of one another, but the reasoning is basically similar for each.

This selection process is based on the following rationale: A given antibody's antigen specificity and affinity is primarily determined by the amino acid sequence of the variable region CDRs. Variable domain framework residues have little or no direct contribution. The primary function of the framework regions is to hold the CDRs in their proper spatial orientation to recognize antigen. Thus the substitution of animal, for example, rodent CDRs into a human variable domain framework is most likely to result in retention of their correct spatial orientation if the human variable domain framework is highly homologous to the animal variable domain from which they originated. A human variable domain should preferably be chosen therefore that is highly homologous to the animal variable domain(s). A suitable human antibody variable domain sequence can be selected as follow.

Step 1. Using a computer program, search all available protein (and DNA) databases for those human antibody variable domain sequences that are most homologous to the animal-derived antibody variable domains. The output of a suitable program is a list of sequences most homologous to the animal-derived antibody, the percent homology to each sequence, and an alignment of each sequence to the animal-derived sequence. This is done independently for both the heavy and light chain variable domain sequences. The above analyses are more easily accomplished if only human immunoglobulin sequences are included.

Step 2. List the human antibody variable domain sequences and compare for homology. Primarily the comparison is performed on length of CDRs, except CDR3 of the heavy chain which is quite variable. Human heavy chains and Kappa and Lambda light chains are divided into subgroups; Heavy chain 3 subgroups, Kappa chain 4 subgroups, Lambda chain 6 subgroups. The CDR sizes within each subgroup are similar but vary between subgroups. It is usually possible to match an animal-derived antibody CDR to one of the human subgroups as a first approximation of homology. Antibodies bearing CDRs of similar length are then compared for amino acid sequence homology, especially within the CDRs, but also in the surrounding framework regions. The human variable domain which is most homologous is chosen as the framework for humanisation.

The Actual Humanising Methodologies/Techniques

An antibody may be humanized by grafting the desired CDRs onto a human framework according to EP-A-0239400. A DNA sequence encoding the desired reshaped antibody can therefore be made beginning with the human DNA whose CDRs it is wished to reshape. The animal-derived variable domain amino acid sequence containing the desired CDRs is compared to that of the chosen human antibody variable domain sequence. The residues in the human variable domain are marked that need to be changed to the corresponding residue in the animal to make the human variable region incorporate the animal-derived CDRs. There may also be residues that need substituting in, adding to or deleting from the human sequence.

Oligonucleotides are synthesized that can be used to mutagenize the human variable domain framework to contain the desired residues. Those oligonucleotides can be of any convenient size. One is normally only limited in length by the capabilities of the particular synthesizer one has available. The method of oligonucleotide-directed in vitro mutagenesis is well known.

Alternatively, humanisation may be achieved using the recombinant polymerase chain reaction (PCR) methodology of WO 92/07075. Using this methodology, a CDR may be spliced between the framework regions of a human antibody. In general, the technique of WO 92/07075 can be performed using a template comprising two human framework regions, AB and CD, and between them, the CDR which is to be replaced by a donor CDR. Primers A and B are used to amplify the framework region AB, and primers C and D used to amplify the framework region CD. However, the primers B and C each also contain, at their 5' ends, an additional sequence corresponding to all or at least part of the donor CDR sequence. Primers B and C overlap by a length sufficient to permit annealing of their 5' ends to each other under conditions which allow a PCR to be performed. Thus, the amplified regions AB and CD may undergo gene splicing by overlap extension to produce the humanized product in a single reaction.

Following the mutagenesis reactions to reshape the antibody, the mutagenised DNAs can be linked to an appropriate DNA encoding a light or heavy chain constant region, cloned into an expression vector, and transfected into host cells, preferably mammalian cells. These steps can be carried out in routine fashion. A reshaped antibody may therefore be prepared by a process comprising:

(a) preparing a first replicable expression vector including a suitable promoter operably linked to a DNA sequence which encodes at least a variable domain of an Ig heavy or light chain, the variable domain comprising framework regions from a human antibody and the CDRs required for the humanized antibody of the invention;

(b) preparing a second replicable expression vector including a suitable promoter operably linked to a DNA sequence which encodes at least the variable domain of a complementary Ig light or heavy chain respectively;

(c) transforming a cell line with the first or both prepared vectors; and (d) culturing said transformed cell line to produce said altered antibody.

Preferably the DNA sequence in step (a) encodes both the variable domain and each constant domain of the human antibody chain. The humanized antibody can be prepared using any suitable recombinant expression system. The cell line which is transformed to produce the altered antibody may be a Chinese Hamster Ovary (CHO) cell line or an immortalised mammalian cell line, which is advantageously of lymphoid origin, such as a myeloma, hybridoma, trioma or quadroma cell line. The cell line may also comprise a normal lymphoid cell, such as a B-cell, which has been immortalised by transformation with a virus, such as the Epstein-Barr virus. Most preferably, the immortalised cell line is a myeloma cell line or a derivative thereof.

The CHO cells used for expression of the antibodies may be dihydrofolate reductase (dhfr) deficient and so dependent on thymidine and hypoxanthine for growth. The parental dhfr⁻ CHO cell line is transfected with the DNA encoding the antibody and dhfr gene which enables selection of CHO cell transformants of dhfr positive phenotype. Selection is carried out by culturing the colonies on media devoid of thymidine and hypoxanthine, the absence of which prevents untransformed cells from growing and transformed cells from resalvaging the folate pathway and thus bypassing the selection system. These transformants usually express low levels of the DNA of interest by virtue of co-integration of transfected DNA of interest and DNA encoding dhfr. The expression levels of the DNA encoding the antibody may be increased by amplification using methotrexate (MTX). This drug is a direct inhibitor of the enzyme dhfr and allows isolation of resistant colonies which amplify their dhfr gene copy number sufficiently to survive under these conditions. Since the DNA sequences encoding dhfr and the antibody are closely linked in the original transformants, there is usually concomitant amplification, and therefore increased expression of the desired antibody.

Another preferred expression system for use with CHO or myeloma cells is the glutamine synthetase (GS) amplification system described in WO 87/04462. This system involves the transfection of a cell with DNA encoding the enzyme GS and with DNA encoding the desired antibody. Cells are then selected which grow in glutamine free medium and can thus be assumed to have integrated the DNA encoding GS. These selected clones are then subjected to inhibition of the enzyme GS using methionine sulphoximine (Msx). The cells, in order to survive, will amplify the DNA encoding GS with concomitant amplification of the DNA encoding the antibody.

Although the cell line used to produce the humanized antibody is preferably a mammalian cell line, any other suitable cell line, such as a bacterial cell line or a yeast cell line, may alternatively be used. In particular, it is envisaged that *E. coli*-derived bacterial strains could be used. The antibody obtained is checked for functionality. If functionality is lost, it is necessary to return to step (2) and alter the framework of the antibody.

Once expressed, the whole antibodies, their dimers, individual light and heavy chains, or other immunoglobulin forms can be recovered and purified according to standard procedures of the art, including ammonium sulfate precipitation, affinity columns, column chromatography, gel electrophoresis and the like (See, generally, Scopes, R., Protein Purification, Springer-Verlag, N.Y. (1982)). Substantially pure immunoglobulins of at least about 90 to 95% homogeneity are preferred, and 98 to 99% or more homogeneity most preferred, for pharmaceutical uses. Once purified, partially or to homogeneity as desired, a humanized antibody may then be used therapeutically or in developing and performing assay procedures, immunofluorescent stainings, and the like (See, generally, Lefkovits and Pernis (editors), Immunological Methods, Vols. I and II, Academic Press, (1979 and 1981)).

Studies carried out by Greenwood et al. (1993) have demonstrated that recognition of the Fc region of an antibody by human effector cells can be optimised by engineering the constant region of the immunoglobulin molecule. This could be achieved by fusing the variable region genes of the antibody, with the desired specificity, to human constant region genes encoding immunoglobulin isotypes that have demonstrated effective antigen dependent cellular cytotoxicity (ADCC) in human subjects, for example the IgG1 and IgG3 isotypes (Greenwood and Clark, Protein Engineering of Antibody Molecules for Prophylactic and Therapeutic Applications in Man. Mike Clark (editor), Academic Titles, Section II, p. 85-113, (1993)). The resulting chimeric or humanized antibodies to 5B6 should be particularly effective in modulating humoral immunity and/or T-cell mediated immunity.

Antibodies with fully human variable regions against 5B6 can also be prepared by administering the antigen to a transgenic animal which has been modified to produce such antibodies in response to antigenic challenge, but whose endogenous loci have been disabled. Various subsequent manipulations can be performed to obtain either antibodies per se or analogs thereof (see, for example, U.S. Pat. No. 6,075,181).

Preparation of Genes Encoding Antibodies or Fragments Thereof

Genes encoding antibodies, both light and heavy chain genes or portions thereof, e.g., single chain Fv regions, may be cloned from a hybridoma cell line. They may all be cloned using the same general strategy such as RACE using a commercially available kit, for example as produced by Clontech. Typically, for example, poly(A)$^+$mRNA extracted from the hybridoma cells is reverse transcribed using random hexamers as primers. For Fv regions, the $V_H$ and $V_L$ domains are amplified separately by two polymerase chain reactions (PCR). Heavy chain sequences may be amplified using 5' end primers which are designed according to the amino-terminal protein sequences of the anti-5B6 heavy chains respectively and 3' end primers according to consensus immunoglobulin constant region sequences (Kabat et al., Sequences of Proteins of Immunological Interest. 5th edition. U.S. Department of Health and Human Services, Public Health Service, National Institutes of Health, Bethesda, Md. (1991)). Light chain Fv regions are amplified using 5' end primers designed according to the amino-terminal protein sequences of anti-5B6 light chains and in combination with the primer C-kappa. One of skill in the art would recognize that many suitable primers may be employed to obtain Fv regions.

The PCR products are subcloned into a suitable cloning vector. Clones containing the correct size insert by DNA restriction are identified. The nucleotide sequence of the heavy or light chain coding regions may then be determined from double stranded plasmid DNA using sequencing primers adjacent to the cloning site. Commercially available kits (e.g., the Sequenase™ kit, United States Biochemical Corp., Cleveland, Ohio, USA) may be used to facilitate sequencing the DNA. DNA encoding the Fv regions may be prepared by any suitable method, including, for example, amplification techniques such as PCR and LCR.

Chemical synthesis produces a single stranded oligonucleotide. This may be converted into double stranded DNA by hybridization with a complementary sequence, or by polymerization with a DNA polymerase using the single strand as a template. While it is possible to chemically synthesize an entire single chain Fv region, it is preferable to synthesize a number of shorter sequences (about 100 to 150 bases) that are later ligated together.

Alternatively, sub-sequences may be cloned and the appropriate subsequences cleaved using appropriate restriction enzymes. The fragments may then be ligated to produce the desired DNA sequence.

Once the Fv variable light and heavy chain DNA is obtained, the sequences may be ligated together, either directly or through a DNA sequence encoding a peptide linker, using techniques well known to those of skill in the art. In one embodiment, heavy and light chain regions are connected by a flexible peptide linker (e.g., $(Gly_4Ser)_3$) which starts at the carboxyl end of the heavy chain Fv domain and ends at the amino terminus of the light chain Fv domain. The entire sequence encodes the Fv domain in the form of a single-chain antigen binding protein.

Therapeutic Agents

Compounds of the invention which bind 5B6 can be used to deliver a therapeutic agent. Examples of therapeutic agents include, but are not limited to, an antigen, a cytotoxic agent, a drug and/or pharmacological agent.

In some embodiments, the therapeutic agent may be a polypeptide fused to a compound that binds 5B6. Fusion polypeptides comprising a compound that binds 5B6 may be prepared by methods known to one of skill in the art. For example, a gene encoding an Fv region is fused to a gene encoding a therapeutic agent. Optionally, the Fv gene is linked to a segment encoding a peptide connector. The peptide connector may be present simply to provide space between the compound that binds 5B6 and the therapeutic agent or to facilitate mobility between these regions to enable them to each attain their optimum conformation. The DNA sequence comprising the connector may also provide sequences (such as primer sites or restriction sites) to facilitate cloning or may preserve the reading frame between the sequence encoding the binding moiety and the sequence encoding the therapeutic agent. The design of such connector peptides is well known to those of skill in the art.

Generally producing fusion polypeptides involves, e.g., separately preparing the Fv light and heavy chains and DNA encoding any other protein to which they are fused and recombining the DNA sequences in a plasmid or other vector to form a construct encoding the particular desired fusion polypeptide. However, a simpler approach involves inserting the DNA encoding the particular Fv region into a construct already encoding the desired second polypeptide. The DNA sequence encoding the Fv region is inserted into the construct using techniques well known to those of skill in the art.

Compounds that bind 5B6 or fragments thereof, e.g., heavy chain of Ab recombinant single chain antibodies, may be fused to, or otherwise bound to the therapeutic agent by any method known and available to those in the art. The two components may be chemically bonded together by any of a variety of well-known chemical procedures. For example, the linkage may be by way of heterobifunctional cross-linkers, e.g., SPDP, carbodiimide, glutaraldehyde, or the like. Production of various immunotoxins, as well as chemical conjugation methods, are well-known within the art (see, for example, "Monoclonal Antibody-Toxin Conjugates: Aiming the Magic Bullet," Thorpe et al., Monoclonal Antibodies in Clinical Medicine, Academic Press, p. 168-190 (1982); Waldmann, 1991; Vitetta et al., 1987; Pastan et al., 1986; and Thorpe et al., 1987).

Examples of drugs and/or pharmacological agents include, but are not limited to, agents that promote DC activation (e.g. TLR ligands), agents that suppress DC activation or function (e.g. specific inhibitors or promotors of DC signalling molecules such as kinases and phosphatases), and agents that modulate DC death (e.g. promotors or suppressors of apoptosis). Such drugs and/or pharmacological agents are well known to those skilled in the art.

The skilled person will appreciate that there are a number of bacterial or plant polypeptide toxins that are suitable for use as cytotoxic agents in the methods of the invention. These polypeptides include, but are not limited to, polypeptides such as native or modified *Pseudomonas* exotoxin, diphtheria toxin, ricin, abrin, gelonin, momordin II, bacterial RIPs such as shiga and shiga-like toxin a-chains, luffin, atrichosanthin, momordin I, Mirabilis anti-viral protein, pokeweed antiviral protein, byodin 2 (U.S. Pat. No. 5,597,569), gaporin, as well as genetically engineered variants thereof. Native *Pseudomonas* exotoxin and diptheria toxin are highly toxic compounds that typically bring about death through liver toxicity. Preferably, *Pseudomonas* exotoxin and diptheria toxin are modified into a form that removes the native targeting component of the toxin, e.g., domain Ia of *Pseudomonas* extoxin and the B chain of diptheria toxin. One of skill in the art will appreciate that the invention is not limited to a particular cytotoxic agent.

Other suitable cytotoxic agents for use in the present invention include, but are not limited to, agents such as bacterial or plant toxins, drugs, e.g., cyclophosphamide (CTX; cytoxan), chlorambucil (CHL; leukeran), cisplatin (C is P; CDDP; platinol), busulfan (myleran), melphalan, carmustine (BCNU), streptozotocin, triethylenemelamine (TEM), mitomycin C, and other alkylating agents; methotrexate (MTX), etoposide (VP-16; vepesid), 6-mercaptopurine (6 MP), 6-thioguanine (6TG), cytarabine (Ara-C), 5-fluorouracil (5FU), dacarbazine (DTIC), 2-chlorodeoxyadenosine (2-CdA), and other antimetabolites; antibiotics including actinomycin D, doxorubicin (DXR; adriamycin), daunorubicin (daunomycin), bleomycin, mithramycin as well as other antibiotics; alkaloids such as vincristin (VCR), vinblastine, and the like; as well as other anti-cancer agents including the cytostatic agents glucocorticoids such as dexamethasone (DEX; decadron) and corticosteroids such as prednisone, nucleotide enzyme inhibitors such as hydroxyurea, and the like.

Those skilled in the art will realize that there are numerous other radioisotopes and chemocytotoxic agents that can be coupled to compounds which bind 5B6 by well known techniques, and delivered to specifically destroy dendritic cells or precursors thereof (see, e.g., U.S. Pat. No. 4,542,225). Examples of photo-activated toxins include dihydropyridine- and omega-conotoxin. Examples of cytotoxic reagents that can be used include $^{125}I$, $^{131}I$, $^{111}In$, $^{123}I$, $^{99}mTc$, and $^{32}P$. The antibody can be labeled with such reagents using techniques known in the art. For example, see Wenzel and Meares, Radioimmunoimaging and Radioimmunotherapy, Elsevier, N.Y. (1983) for techniques relating to the radiolabeling of antibodies (see also, Colcher et al., 1986; "Order, Analysis, Results and Future Prospective of the Therapeutic Use of Radiolabeled Antibody in Cancer Therapy", Monoclonal Antibodies for Cancer Detection and Therapy, Baldwin et al. (editors), Academic Press, p. 303-16, (1985)).

In one example, the linker-chelator tiuexutan is conjugated to a compound which binds 5B6, by a stable thiourea covalent bond to provide a high-affinity chelation site for Indium-111 or Yttrium-90.

Antigens

The term "antigen" is further intended to encompass peptide or protein analogs of known or wild-type antigens such as those described above. The analogs may be more soluble or more stable than wild type antigen, and may also contain mutations or modifications rendering the antigen more immunologically active. Also useful in the present invention are peptides or proteins which have amino acid sequences homologous with a desired antigen's amino acid sequence, where the homologous antigen induces an immune response to the respective tumor or organism.

A "cancer antigen," as used herein is a molecule or compound (e.g., a protein, peptide, polypeptide, lipid, glycolipid, carbohydrate and/or DNA) associated with a tumor or cancer cell and which is capable of provoking an immune response when expressed on the surface of an antigen presenting cell in the context of an MHC molecule. Cancer antigens include self antigens, as well as other antigens that may not be specifically associated with a cancer, but nonetheless induce and/or enhance an immune response to and/or reduce the growth of a tumor or cancer cell when administered to an animal.

An "antigen from a pathogenic and/or infectious organism" as used herein, is an antigen of any organism and includes, but is not limited to, infectious virus, infectious bacteria, infectious parasites including protozoa (such as *Plasmodium* sp.) and worms and infectious fungi. Typically, for use in the invention the antigen is a protein or antigenic fragment thereof from the organism, or a synthetic compound which is identical to or similar to naturally-occurring antigen which induces an immune response specific for the corresponding organism. Compounds or antigens that are similar to a naturally-occurring organism antigens are well known to those of ordinary skill in the art. A non-limiting example of a compound that is similar to a naturally-occurring organism antigen is a peptide mimic of a polysaccharide antigen.

Specific embodiments of cancer antigens include, e.g., mutated antigens such as the protein products of the Ras p21 protooncogenes, tumor suppressor p53 and HER-2/neu and BCR-abl oncogenes, as well as CDK4, MUM1, Caspase 8, and Beta catenin; overexpressed antigens such as galectin 4, galectin 9, carbonic anhydrase, Aldolase A, PRAME, Her2/neu, ErbB-2 and KSA, oncofetal antigens such as alpha fetoprotein (AFP), human chorionic gonadotropin (hCG); self antigens such as carcinoembryonic antigen (CEA) and melanocyte differentiation antigens such as Mart 1/Melan A, gp100, gp75, Tyrosinase, TRP1 and TRP2; prostate associated antigens such as PSA, PAP, PSMA, PSM-P1 and PSM-P2; reactivated embryonic gene products such as MAGE 1, MAGE 3, MAGE 4, GAGE 1, GAGE 2, BAGE, RAGE, and other cancer testis antigens such as NY-ESO1, SSX2 and SCP1; mucins such as Muc-1 and Muc-2; gangliosides such as GM2, GD2 and GD3, neutral glycolipids and glycoproteins such as Lewis (y) and globo-H; and glycoproteins such as Tn, Thompson-Freidenreich antigen (TF) and sTn.

Cancer antigens and their respective tumor cell targets include, e.g., cytokeratins, particularly cytokeratin 8, 18 and 19, as antigens for carcinoma. Epithelial membrane antigen (EMA), human embryonic antigen (HEA-125), human milk fat globules, MBr1, MBr8, Ber-EP4, 17-1A, C26 and T16 are also known carcinoma antigens. Desmin and muscle-specific actin are antigens of myogenic sarcomas. Placental alkaline phosphatase, beta-human chorionic gonadotropin, and alpha-fetoprotein are antigens of trophoblastic and germ cell tumors. Prostate specific antigen is an antigen of prostatic carcinomas, carcinoembryonic antigen of colon adenocarcinomas. HMB-45 is an antigen of melanomas. In cervical cancer, useful antigens could be encoded by human papilloma virus. Chromagranin-A and synaptophysin are antigens of neuroendocrine and neuroectodermal tumors. Of particular interest are aggressive tumors that form solid tumor masses having necrotic areas.

Antigens derived from pathogens known to predispose to certain cancers may also be advantageously used in the present invention. Pathogens of particular interest for use in the cancer vaccines provided herein include the hepatitis B virus (hepatocellular carcinoma), hepatitis C virus (heptomas), Epstein Barr virus (EBV) (Burkitt lymphoma, nasopharynx cancer, PTLD in immunosuppressed individuals), HTLVL (adult T cell leukemia), oncogenic human papilloma viruses types 16, 18, 33, 45 (adult cervical cancer), and the bacterium *Helicobacter pylori* (B cell gastric lymphoma). Other medically relevant microorganisms that may serve as antigens in mammals and more particularly humans are described extensively in the literature, e.g., C. G. A Thomas, Medical Microbiology, Bailliere Tindall, (1983).

Exemplary viral pathogens include, but are not limited to, infectious virus that infect mammals, and more particularly humans. Examples of infectious virus include, but are not limited to: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses such as the SARS coronavirus); Rhabdoviradae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Also, gram negative and gram positive bacteria may be targeted by the subject compositions and methods in vertebrate animals. Such gram positive bacteria include, but are not limited to *Pasteurella* sp., *Staphylococci* sp., and *Streptococcus* sp. Gram negative bacteria include, but are not limited to, *Escherichia coli*, *Pseudomonas* sp., and *Salmonella* sp. Specific examples of infectious bacteria include but are not limited to: *Helicobacter pyloris*, *Borella burgdorferi*, *Legionella pneumophilia*, *Mycobacteria* sp. (e.g. *M. tuberculosis*, *M. avium*, *M. intracellulare*, *M. kansaii*, *M. gordonae*), *Staphylococcus aureus*, *Neisseria gonorrhoeae*, *Neisseria meningitidis*, *Listeria monocytogenes*, *Streptococcus pyogenes* (Group A *Streptococcus*), *Streptococcus agalactiae* (Group B *Streptococcus*), *Streptococcus* (viridans group), *Streptococcus faecalis*, *Streptococcus bovis*, *Streptococcus* (anaerobic sps.), *Streptococcus pneumoniae*, pathogenic *Campylobacter* sp., *Enterococcus* sp., *Haemophilus* infuenzae, *Bacillus antracis*, *Corynebacterium diphtheriae*, *Corynebacterium* sp., *Erysipelothrix rhusiopathiae*, *Clostridium perfringens*, *Clostridium tetani*, *Enterobacter aerogenes*, *Klebsiella pneumoniae*, *Pasturella multocida*, *Bacteroides* sp., *Fusobacterium nucleatum*, *Streptobacillus moniliformis*, *Treponema pallidium*, *Treponema pertenue*, *Leptospira*, *Rickettsia*, and *Actinomyces israelli*.

Polypeptides of bacterial pathogens which may find use as sources of antigen in the subject compositions include but are not limited to an iron-regulated outer membrane protein, ("TROMP"), an outer membrane protein ("OMP"), and an A-protein of *Aeromonis salmonicida* which causes furunculosis, p57 protein of *Renibacterium salmoninarum* which causes bacterial kidney disease ("BKD"), major surface associated antigen ("msa"), a surface expressed cytotoxin ("mpr"), a surface expressed hemolysin ("ish"), and a flagellar antigen of Yersiniosis; an extracellular protein ("ECP"), an iron-regulated outer membrane protein ("TROMP"), and a structural protein of Pasteurellosis; an OMP and a flagellar protein of *Vibrosis anguillarum* and *V. ordalii*; a flagellar protein, an OMP protein, aroA, and purA of *Edwardsiellosis ictaluri* and *E. tarda*; and surface antigen of *Ichthyophthirius*; and a structural and regulatory protein of *Cytophaga columnari*; and a structural and regulatory protein of *Rickettsia*. Such antigens can be isolated or prepared recombinantly or by any other means known in the art.

Examples of pathogens further include, but are not limited to, infectious fungi and parasites that infect mammals, and more particularly humans. Examples of infectious fungi include, but are not limited to: *Cryptococcus neoformans, Histoplasma capsulatum, Coccidioides immitis, Blastomyces dermatitidis, Chlamydia trachomatis*, and *Candida albicans*.

Examples of parasites include intracellular parasites and obligate intracellular parasites. Examples of parasites include but are not limited to *Plasmodium falciparum, Plasmodium ovale, Plasmodium malariae, Plasmdodium vivax, Plasmodium knowlesi, Babesia microti, Babesia divergens, Trypanosoma cruzi, Toxoplasma gondii, Trichinella spiralis, Leishmania major, Leishmania donovani, Leishmania braziliensis, Leishmania tropica, Trypanosoma gambiense, Trypanosoma rhodesiense, Wuchereria bancrofti, Brugia malayi, Brugia timori, Ascaris lumbricoides, Onchocerca volvulus* and *Schistosoma mansoni*.

Other medically relevant microorganisms that serve as antigens in mammals and more particularly humans are described extensively in the literature, e.g., see C. G. A Thomas, Medical Microbiology, Bailliere Tindall, (1983). In addition to the treatment of infectious human diseases and human pathogens, the compositions and methods of the present invention are useful for treating infections of non-human mammals. Exemplary non-human pathogens include, but are not limited to, mouse mammary tumor virus ("MMTV"), Rous sarcoma virus ("RSV"), avian leukemia virus ("ALV"), avian myeloblastosis virus ("AMV"), murine leukemia virus ("MLV"), feline leukemia virus ("FeLV"), murine sarcoma virus ("MSV"), gibbon ape leukemia virus ("GALV"), spleen necrosis virus ("SNV"), reticuloendotheliosis virus ("RV"), simian sarcoma virus ("SSV"), Mason-Pfizer monkey virus ("MPMV"), simian retrovirus type 1 ("SRV-1"), lentiviruses such as HIV-1, HIV-2, SIV, Visna virus, feline immunodeficiency virus ("FIV"), and equine infectious anemia virus ("EIAV"), T-cell leukemia viruses such as HTLV-1, HTLV-II, simian T-cell leukemia virus ("STLV"), and bovine leukemia virus ("BLV"), and foamy viruses such as human foamy virus ("HFV"), simian foamy virus ("SFV") and bovine foamy virus ("BFV").

Detectable Labels

Compounds that bind 5B6 may be employed in a range of detection systems. For example, the compound may be used in methods for imaging an internal region of a subject and/or diagnosing the presence or absence of a disease in a subject. For example, compounds that bind 5B6 can be used for the diagnosis of diseases in which 5B6 expressing cells play a role.

It will be apparent to those skilled in the art that the diagnostic or prognostic methods of the present invention involve a degree of quantification to determine levels of 5B6, or levels of 5B6 expressing cells, present in patient samples. Such quantification is readily provided by the inclusion of appropriate control samples.

Preferably, internal controls are included in the methods of the present invention. A preferred internal control is one or more samples taken from one or more healthy individuals.

Compounds which bind 5B6 when used diagnostically may be linked to a diagnostic reagent such as a detectable label to allow easy detection of binding events in vitro or in vivo. Suitable labels include radioisotopes, or non-radioactive labels such as biotin, enzymes, chemiluminescent molecules, fluorophores, dye markers or other imaging reagents for detection and/or localisation of target molecules. Alternatively, a second labelled antibody or avidin (for example) which binds the compound can be used for detection.

In the case of an enzyme immunoassay, an enzyme can be conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, β-galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above.

In another example, fluorescent compounds, such as but not limited to fluorescein and rhodamine amongst others, may be chemically coupled to, for example, antibodies without altering their binding capacity. When activated by illumination with light of a particular wavelength, the fluorochrome-labelled antibody adsorbs the light energy, inducing a state to excitability in the molecule, followed by emission of the light at a characteristic color visually detectable with a light microscope.

By further way of non-limiting example, the compounds which bind 5B6 coupled to imaging agents can be used in the detection of 5B6 expression in histochemical tissue sections. The compound may be covalently or non-covalently coupled to a suitable supermagnetic, paramagnetic, electron dense, echogenic, radioactive, or non-radioactive labels such as biotin or avidin.

Labelled Dendritic Cell or Precursor Thereof Detection and Isolation

As used herein, the terms "enriching" and "enriched" are used in their broadest sense to encompass the isolation of dendritic cells or precursors thereof such that the relative concentration of dendritic cells or precursors thereof to non-dendritic cells or precursors thereof in the treated sample is greater than a comparable untreated sample. Preferably, the enriched dendritic cells and/or precursors thereof are separated from at least 10%, more preferably at least 20%, more preferably at least 30%, more preferably at least 40%, more preferably at least 50%, more preferably at least 60%, more preferably at least 70%, more preferably at least 75%, more preferably at least 80%, more preferably at least 90%, more preferably at least 95%, and even more preferably at least 99% of the non-dendritic cells or precursors thereof in the sample obtained from the original sample. Most preferably, the enriched cell population contains no non-dendritic cells or precursors thereof (namely, pure). The terms "enrich" and variations thereof are used interchangeably herein with the term "isolate" and variations thereof. Furthermore, a population of cells enriched using a method of the invention may only comprise a single dendritic cell or precursor thereof. In addition, the enrichment methods of the invention may be used to isolate a single dendritic cell or precursor thereof.

Dendritic cells or precursors thereof can be enriched from the sample by a variety of techniques well known in the art, including cell sorting, especially fluorescence-activated cell sorting (FACS), by using an affinity reagent bound to a substrate (e.g., a plastic surface, as in panning), or by using an affinity reagent bound to a solid phase particle which can be isolated on the basis of the properties of the beads (e.g., colored latex beads or magnetic particles). Naturally, the procedure used to enrich the dendritic cells and/or precursors thereof will depend upon how the cells have been labelled.

In one example, any detectable substance which has the appropriate characteristics for the cell sorter may be used (e.g., in the case of a fluorescent dye, a dye which can be excited by the sorter's light source, and an emission spectra which can be detected by the cell sorter's detectors). In flow cytometry, a beam of laser light is projected through a liquid stream that contains cells, or other particles, which when struck by the focussed light give out signals which are picked up by detectors. These signals are then converted for computer storage and data analysis, and can provide information about various cellular properties. Cells labelled with a suitable dye are excited by the laser beam, and emit light at characteristic wavelengths. This emitted light is picked up by detectors, and these analogue signals are converted to digital signals, allowing for their storage, analysis and display.

Many larger flow cytometers are also "cell sorters", such as fluorescence-activated cell sorters (FACS), and are instruments which have the ability to selectively deposit cells from particular populations into tubes, or other collection vessels. In a particularly preferred embodiment, the cells are isolated using FACS. This procedure is well known in the art and described by, for example, Melamed et al., Flow Cytometry and Sorting, Wiley-Liss, Inc., (1990); Shapiro, Practical Flow Cytometry, 4th Edition, Wiley-Liss, Inc., (2003); and Robinson et al., Handbook of Flow Cytometry Methods, Wiley-Liss, Inc. (1993).

In order to sort cells, the instruments electronics interprets the signals collected for each cell as it is interrogated by the laser beam and compares the signal with sorting criteria set on the computer. If the cell meets the required criteria, an electrical charge is applied to the liquid stream which is being accurately broken into droplets containing the cells. This charge is applied to the stream at the precise moment the cell of interest is about to break off from the stream, then removed when the charged droplet has broken from the stream. As the droplets fall, they pass between two metal plates, which are strongly positively or negatively charged. Charged droplets get drawn towards the metal plate of the opposite polarity, and deposited in the collection vessel, or onto a microscope slide, for further examination.

The cells can automatically be deposited in collection vessels as single cells or as a plurality of cells, e.g. using a laser, e.g. an argon laser (488 nm) and for example with a Flow Cytometer fitted with an Autoclone unit (Coulter EPICS Altra, Beckman-Coulter, Miami, Fla., USA). Other examples of suitable FACS machines useful for the methods of the invention include, but are not limited to, MoFlo™ High-speed cell sorter (Dako-Cytomation ltd), FACS Aria™ (Becton Dickinson), FACS Diva (Becton Dickinson), ALTRA™ Hyper sort (Beckman Coulter) and CyFlow™ sorting system (Partec GmbH).

The enrichment of dendritic cells and/or or precursors thereof from a sample using solid-phase particles, any particle with the desired properties may be utilized. For example, large particles (e.g., greater than about 90-100 µm in diameter) may be used to facilitate sedimentation. Preferably, the particles are "magnetic particles" (i.e., particles which can be collected using a magnetic field). Labelled cells are retained in the column (held by the magnetic field), whilst unlabelled cells pass straight through and are eluted at the other end. Magnetic particles are now commonly available from a variety of manufacturers including Dynal Biotech (Oslo, Norway) and Milteni Biotech GmbH (Germany). An example of magnetic cell sorting (MACS) is provided by Al-Mufti et al. (1999).

Laser-capture microdissection can also be used to selectively enrich labelled dendritic cells or precursors thereof on a slide using methods of the invention. Methods of using laser-capture microdissection are known in the art (see, for example, U.S. 20030227611 and Bauer et al., 2002).

Following enrichment, the cells can be used immediately or cultured in vitro to expand dendritic cells and/or precursors thereof numbers using techniques known in the art. Furthermore, dendritic cell precursors can be cultured to produce mature dendritic cells.

Identification of Compounds that Bind 5B6

Methods of screening test compounds are described which can identify a compound that either binds to 5B6, and is thus useful as, for example, a targeting agent for association with a therapeutic agent, and/or a compound that binds to and inhibits or antagonizes the biological activity of 5B6 directly.

Inhibitors of 5B6 activity are screened by resort to assays and techniques useful in identifying drugs capable of binding to the 5B6 polypeptide and thereby inhibiting its biological activity in a dendritic cell or precursor thereof. Such assays include the use of mammalian cell lines (for example, CHO cells or 293T cells) for phage display for expressing the 5B6 polypeptide, and using primary cells or parental cell lines or a culture of transfected mammalian or E. coli or other microorganism to produce the proteins for binding studies of potential binding compounds.

Other conventional drug screening techniques are employed using the proteins, antibodies or polynucleotide sequences of this invention. As one example, a method for identifying compounds which specifically bind to a 5B6 polypeptide of this invention can include simply the steps of contacting a selected cell expressing 5B6 with a test compound to permit binding of the test compound to 5B6 and determining the amount of test compound, if any, which is bound to the 5B6. Such a method involves the incubation of the test compound and the 5B6 polypeptide immobilized on a solid support. Typically, the surface containing the immobilized compound is permitted to come into contact with a solution containing the protein and binding is measured using an appropriate detection system. Suitable detection systems are known in the art, some of which are described herein.

Methods for producing antibodies, or fragments thereof, which bind 5B6 are described above.

Computer modeling and searching technologies permit identification of compounds that can bind polypeptides of the invention. The three dimensional geometric structure of 5B6 or the active site thereof can be determined. This can be done by known methods, including X-ray crystallography, which can determine a complete molecular structure.

Methods of computer based numerical modeling can be used to complete the structure (e.g., in embodiments wherein an incomplete or insufficiently accurate structure is determined) or to improve its accuracy. Any method recognized in the art may be used, including, but not limited to, parameterized models specific to particular biopolymers such as proteins or nucleic acids, molecular dynamics models based on computing molecular motions, statistical mechanics models based on thermal ensembles, or combined models.

The three-dimensional structure of 5B6 can be used to identify antagonists or agonists through the use of computer modeling using a docking program such as GRAM, DOCK, or AUTODOCK (Dunbrack et al., 1997). Computer programs can also be employed to estimate the attraction, repulsion, and steric hindrance of a candidate compound to the polypeptide. Generally the tighter the fit (e.g., the lower the steric hindrance, and/or the greater the attractive force) the more potent the potential agonist or antagonist will be since these properties are consistent with a tighter binding constant. Furthermore, the more specificity in the design of a potential agonist or antagonist the more likely that it will not interfere with other proteins.

Initially a potential compound could be obtained, for example, using methods of the invention such as by screening a random peptide library produced by a recombinant bacteriophage or a chemical library. A compound selected in this manner could be then be systematically modified by computer modeling programs until one or more promising potential compounds are identified.

Such computer modeling allows the selection of a finite number of rational chemical modifications, as opposed to the countless number of essentially random chemical modifications that could be made, and of which any one might lead to a useful agonist or antagonist. Each chemical modification requires additional chemical steps, which while being reasonable for the synthesis of a finite number of compounds, quickly becomes overwhelming if all possible modifications needed to be synthesized. Thus through the use of the three-dimensional structure and computer modeling, a large number of these compounds can be rapidly screened on the computer monitor screen, and a few likely candidates can be determined without the laborious synthesis of untold numbers of compounds.

For most types of models, standard molecular force fields, representing the forces between constituent atoms and groups, are necessary, and can be selected from force fields known in physical chemistry. Exemplary forcefields that are known in the art and can be used in such methods include, but are not limited to, the Constant Valence Force Field (CVFF), the AMBER force field and the CHARM force field. The incomplete or less accurate experimental structures can serve as constraints on the complete and more accurate structures computed by these modeling methods.

Further examples of molecular modeling systems are the CHARMm and QUANTA programs (Polygen Corporation, Waltham, Mass.). CHARMm performs the energy minimization and molecular dynamics functions. QUANTA performs the construction, graphic modelling and analysis of molecular structure. QUANTA allows interactive construction, modification, visualization, and analysis of the behaviour of molecules with each other.

Microorganism Deposit Details

Hybridoma 20/05-3A4-26-16-Clone 5 and Hybridoma 23/05-4C6-29-3-Clone 5 are hybridomas secreting monoclonal Ab to human C-type lectin clone 5B6.

Hybridoma 24/04-10B4-24-8-FACS 9-5 and Hybridoma 42/04-42D2-66-4-1-Clone 4 are hybridomas secreting monoclonal Ab to mouse C-type lectin clone 5B6.

Hybridoma 24/04-10B4-24-8-FACS 9-5 also secretes monoclonal antibody to human C-type lection clone 5B6.

Antibodies 24/04-10B4, 42/04-42D2, 20/05-3A4 and 23/05-4C6 are produced by hydridoma cell lines deposited with the European Collection of Cell Cultures (ECACC) 24/04-10B4-24-8, 42/04-42D2-66-4-1, 20/05-3A4-26-16, 23/05-4C6-29-3 on 11 Dec. 2007 under Deposit Reference Numbers 07121101, 07121102, 07121103, and 07121104 respectively.

Higher antibody secreting subclones of the above hybridomas (24/04-1084-24-8-FACS 9-5, 42/04-42D2-66-4-1-Clone 4, 20/05-3A4-26-16-Clone 5, 23/05-4C6-29-3-Clone 5) were deposited with the ECACC on 29 Apr. 2008, and designated the following numbers;

Hybridoma 24/04-10B4-24-8-FACS 9-5—Accession no. 08042901

Hybridoma 42/04-42D2-66-4-1 CLONE 4—Accession no. 08041902

Hybridoma 20105-3A4-26-16-CLONE 5—Accession no. 08042903, and

Hybridoma 23/05-4C6-29-3-CLONE 5—Accession no. 08042904.

These deposits were made under the provisions of the Budapest Treaty on the International Recognition of the Deposit of Microorganisms for the Purpose of Patent Procedure and the Regulations thereunder. This assures maintenance of viable cultures for 30 years from the date of deposit. The organisms will be made available by the ECACC under the terms of the Budapest Treaty.

The assignee of the present application has agreed that if the culture deposit should die or be lost or destroyed when cultivated under suitable conditions, it will be promptly replaced on notification with a viable specimen of the same culture. Availability of a deposited strain is not to be construed as a license to practice the invention in contravention of the rights granted under the authority of any government in accordance with its patent laws.

Polypeptides

By "substantially purified" or "purified" we mean a polypeptide that has been separated from one or more lipids, nucleic acids, other polypeptides, or other contaminating molecules with which it is associated in its native state. It is preferred that the substantially purified polypeptide is at least 60% free, more preferably at least 75% free, and more preferably at least 90% free from other components with which it is naturally associated.

The term "recombinant" in the context of a polypeptide refers to the polypeptide when produced by a cell, or in a cell-free expression system, in an altered amount or at an altered rate compared to its native state. In one embodiment the cell is a cell that does not naturally produce the polypeptide. However, the cell may be a cell which comprises a non-endogenous gene that causes an altered, preferably increased, amount of the polypeptide to be produced. A recombinant polypeptide of the invention includes polypeptides which have not been separated from other components of the transgenic (recombinant) cell, or cell-free expression system, in which it is produced, and polypeptides produced in such cells or cell-free systems which are subsequently purified away from at least some other components.

The terms "polypeptide" and "protein" are generally used interchangeably and refer to a single polypeptide chain which may or may not be modified by addition of non-amino acid groups. It would be understood that such polypeptide chains may associate with other polypeptides or proteins or other molecules such as co-factors. The terms "proteins" and "polypeptides" as used herein also include variants, mutants, biologically active fragments, modifications, analogous and/or derivatives of the polypeptides described herein.

The % identity of a polypeptide is determined by GAP (Needleman and Wunsch, 1970) analysis (GCG program) with a gap creation penalty=5, and a gap extension penalty=0.3. The query sequence is at least 25 amino acids in length, and the GAP analysis aligns the two sequences over a region of at least 25 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 200 amino acids in length and the GAP analysis aligns the two sequences over a region of at least 200 amino acids. Even more preferably, the GAP analysis aligns the two sequences over their entire length.

As used herein a "biologically active fragment" is a portion of a polypeptide as described herein which maintains a defined activity of the full-length polypeptide. Biologically active fragments can be any size as long as they maintain the defined activity. Preferably, biologically active fragments are at least 100 amino acids in length. In a preferred embodiment, the biologically active fragment is able to bind to the full length 5B6 protein expressed by a cell such as a dendritic cell. In a particularly preferred embodiment, the biologically active fragment is a soluble fragment which is able to bind to the full length 5B6 protein expressed by a cell such as a dendritic cell. Examples of such soluble biologically active fragments include those which comprise the CTLD region of 5B6 but lack at least the about 40, at least about 50, or at least about 55, or at least about 100, N-terminal residues of any one of SEQ ID NO's 1 to 8. In addition, examples of soluble biologically active fragment of polypeptides of the invention are provided as SEQ ID NO's 58 to 61. Furthermore, examples of fusion proteins comprising a soluble biologically active fragment of polypeptides of the invention are provided in FIG. 11A (SEQ ID NO's 38 to 41).

As used herein, an "antigenic fragment" is a protein of a polypeptide as described herein which can be administered to an animal, for example a mouse, rabbit or human, to induce the production of antibodies that will bind the full length native polypeptide.

As used herein, an "antigenic binding fragment" refers to a portion of an antibody as defined herein that is capable of binding the same antigen as the full length molecule.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Polypeptides of the invention include 5B6 and fragments and variants thereof, as well as polypeptides that bind 5B6 such as antibodies, natural or recombinant ligands/binding partners which may or may not be conjugated/fused to detectable labels or other polypeptides such as antigens or protein toxins.

Amino acid sequence mutants of a polypeptide described herein can be prepared by introducing appropriate nucleotide changes into a nucleic acid defined herein, or by in vitro synthesis of the desired polypeptide. Such mutants include, for example, deletions, insertions or substitutions of residues within the amino acid sequence. A combination of deletion, insertion and substitution can be made to arrive at the final construct, provided that the final polypeptide product possesses the desired characteristics.

Mutant (altered) polypeptides can be prepared using any technique known in the art. For example, a polynucleotide described herein can be subjected to in vitro mutagenesis. Such in vitro mutagenesis techniques may include subcloning the polynucleotide into a suitable vector, transforming the vector into a "mutator" strain such as the E. coli XL-1 red (Stratagene) and propagating the transformed bacteria for a suitable number of generations. In another example, the polynucleotides of the invention are subjected to DNA shuffling techniques as broadly described by Harayama (1998). Products derived from mutated/altered DNA can readily be screened using techniques described herein to determine if they are able to confer the desired phenotype.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites identified as important for function. Other sites of interest are those in which particular residues obtained from various strains or species are identical (see, for example, FIG. 1), and/or those in which particular residues obtained from related proteins are identical (see, for example, FIG. 2). These positions may be important for biological activity. These sites, especially those falling within a sequence of at least three other identically conserved sites, are preferably substituted in a relatively conservative manner. Such conservative substitutions are shown in Table 1.

TABLE 1

| Exemplary substitutions. | |
|---|---|
| Original Residue | Exemplary Substitutions |
| Ala (A) | val; leu; ile; gly |
| Arg (R) | lys |
| Asn (N) | gln; his |
| Asp (D) | glu |

TABLE 1-continued

Exemplary substitutions.

| Original Residue | Exemplary Substitutions |
|---|---|
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe; ala |

In a preferred embodiment a mutant/variant polypeptide has one or two or three or four conservative amino acid changes when compared to a naturally occurring polypeptide. Details of conservative amino acid changes are provided in Table 1. In a preferred embodiment, the changes are not in one or more of the motifs which are highly conserved between the different polypeptides provided herewith. As the skilled person would be aware, such minor changes can reasonably be predicted not to alter the activity of the polypeptide when expressed in a recombinant cell.

Furthermore, if desired, unnatural amino acids or chemical amino acid analogues can be introduced as a substitution or addition into a polypeptides described herein. Such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general.

Also included within the scope of the invention are polypeptides of the present invention which are differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or bioactivity of the polypeptide.

Polypeptides described herein can be produced in a variety of ways, including production and recovery of natural polypeptides, production and recovery of recombinant polypeptides, and chemical synthesis of the polypeptides. In one embodiment, an isolated polypeptide of the present invention is produced by culturing a cell capable of expressing the polypeptide under conditions effective to produce the polypeptide, and recovering the polypeptide. A preferred cell to culture is a recombinant cell of the present invention. Effective culture conditions include, but are not limited to, effective media, bioreactor, temperature, pH and oxygen conditions that permit polypeptide production. An effective medium refers to any medium in which a cell is cultured to produce a polypeptide of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, tissue culture flasks, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Polynucleotides

By an "isolated polynucleotide", including DNA, RNA, or a combination of these, single or double stranded, in the sense or antisense orientation or a combination of both, dsRNA or otherwise, we mean a polynucleotide which is at least partially separated from the polynucleotide sequences with which it is associated or linked in its native state. Preferably, the isolated polynucleotide is at least 60% free, preferably at least 75% free, and most preferably at least 90% free from other components with which they are naturally associated. Furthermore, the term "polynucleotide" is used interchangeably herein with the term "nucleic acid".

The term "exogenous" in the context of a polynucleotide refers to the polynucleotide when present in a cell, or in a cell-free expression system, in an altered amount compared to its native state. In one embodiment, the cell is a cell that does not naturally comprise the polynucleotide. However, the cell may be a cell which comprises a non-endogenous polynucleotide resulting in an altered, preferably increased, amount of production of the encoded polypeptide. An exogenous polynucleotide of the invention includes polynucleotides which have not been separated from other components of the transgenic (recombinant) cell, or cell-free expression system, in which it is present, and polynucleotides produced in such cells or cell-free systems which are subsequently purified away from at least some other components.

The % identity of a polynucleotide is determined by GAP (Needleman and Wunsch, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 250 nucleotides in length and the GAP analysis aligns the two sequences over a region of at least 250 nucleotides. Even more preferably, the GAP analysis aligns the two sequences over their entire length.

With regard to the defined polynucleotides, it will be appreciated that % identity figures higher than those provided above will encompass preferred embodiments. Thus, where applicable, in light of the minimum % identity figures, it is preferred that a polynucleotide of the invention comprises a sequence which is at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

As used herein, the term "hybridizes" refers to the ability of two single stranded nucleic acid molecules being able to form at least a partially double stranded nucleic acid through hydrogen bonding.

As used herein, the phrase "stringent conditions" refers to conditions under which a polynucleotide, probe, primer and/or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present in excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in Ausubel et al. (supra), 6.3.1-6.3.6, as well as the Examples described herein. Preferably, the conditions are such that sequences at least about 65%, 70%, 75%, 85%, 90%, 95%, 98%, or 99% homologous to each other typically remain hybridized to each other. A non-limiting example of stringent hybridization conditions are hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C., followed by one or more washes in 0.2.× SSC, 0.01% BSA at 50° C. In another embodiment, a nucleic acid sequence that is hybridizable to one or more of the nucleic acid molecule comprising the nucleotide sequence of SEQ ID NO's 9 to 16, under conditions of moderate stringency is provided. A non-limiting example of moderate stringency hybridization conditions are hybridization in 6×SSC, 5×Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well-known within the art, see, e.g., Ausubel et al. (supra), and Kriegler, Gene Transfer and Expression, A Laboratory Manual, Stockton Press, (1990). In yet another embodiment, a nucleic acid that is hybridizable to the nucleic acid molecule comprising any one or more of the nucleotide sequences of SEQ ID NO's 9 to 16, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C.

Other conditions of low stringency that may be used are well known in the art, see, e.g., Ausubel et al. (supra) and Kriegler (supra).

Polynucleotides of the present invention may possess, when compared to naturally occurring molecules, one or more mutations which are deletions, insertions, or substitutions of nucleotide residues. Mutants can be either naturally occurring (that is to say, isolated from a natural source) or synthetic (for example, by performing site-directed mutagenesis on the nucleic acid).

Usually, monomers of a polynucleotide or oligonucleotide are linked by phosphodiester bonds or analogs thereof to form oligonucleotides ranging in size from a relatively short monomeric units, e.g., 12-18, to several hundreds of monomeric units. Analogs of phosphodiester linkages include: phosphorothioate, phosphorodithioate, phosphoroselenoate, phosphorodiselenoate, phosphoroanilothioate, phosphoranilidate and phosphoramidate.

Antisense Polynucleotides

The term "antisense polynucleotide" shall be taken to mean a DNA or RNA, or combination thereof, molecule that is complementary to at least a portion of a specific mRNA molecule encoding a polypeptide of the invention and capable of interfering with a post-transcriptional event such as mRNA translation. The use of antisense methods is well known in the art (see for example, G. Hartmann and S. Endres, Manual of Antisense Methodology, Kluwer (1999)). The use of antisense techniques in plants has been reviewed by Bourque, 1995 and Senior, 1998. Bourque, 1995 lists a large number of examples of how antisense sequences have been utilized as a method of gene inactivation. She also states that attaining 100% inhibition of any enzyme activity may not be necessary as partial inhibition will more than likely result in measurable change in the system. Senior (1998) states that antisense methods are now a very well established technique for manipulating gene expression.

An antisense polynucleotide of the invention will hybridize to a target polynucleotide under physiological conditions. As used herein, the term "an antisense polynucleotide which hybridises under physiological conditions" means that the polynucleotide (which is fully or partially single stranded) is at least capable of forming a double stranded polynucleotide with mRNA encoding a protein, such as those provided in any one of SEQ ID NOs 1 to 8 under normal conditions in a cell, preferably a human cell.

Antisense molecules may include sequences that correspond to the structural genes or for sequences that effect control over the gene expression or splicing event. For example, the antisense sequence may correspond to the targeted coding region of the genes of the invention, or the 5'-untranslated region (UTR) or the 3'-UTR or combination of these. It may be complementary in part to intron sequences, which may be spliced out during or after transcription, preferably only to exon sequences of the target gene. In view of the generally greater divergence of the UTRs, targeting these regions provides greater specificity of gene inhibition.

The length of the antisense sequence should be at least 19 contiguous nucleotides, preferably at least 50 nucleotides, and more preferably at least 100, 200, 500 or 1000 nucleotides. The full-length sequence complementary to the entire gene transcript may be used. The length is most preferably 100-2000 nucleotides. The degree of identity of the antisense sequence to the targeted transcript should be at least 90% and more preferably 95-100%. The antisense RNA molecule may of course comprise unrelated sequences which may function to stabilize the molecule.

Catalytic Polynucleotides

The term catalytic polynucleotide/nucleic acid refers to a DNA molecule or DNA-containing molecule (also known in the art as a "deoxyribozyme") or an RNA or RNA-containing molecule (also known as a "ribozyme") which specifically recognizes a distinct substrate and catalyzes the chemical modification of this substrate. The nucleic acid bases in the catalytic nucleic acid can be bases A, C, G, T (and U for RNA).

Typically, the catalytic nucleic acid contains an antisense sequence for specific recognition of a target nucleic acid, and a nucleic acid cleaving enzymatic activity (also referred to herein as the "catalytic domain"). The types of ribozymes that are particularly useful in this invention are the hammerhead ribozyme (Haseloff and Gerlach, 1988; Perriman et al., 1992) and the hairpin ribozyme (Shippy et al., 1999).

The ribozymes of this invention and DNA encoding the ribozymes can be chemically synthesized using methods well known in the art. The ribozymes can also be prepared from a DNA molecule (that upon transcription, yields an RNA molecule) operably linked to an RNA polymerase promoter, e.g., the promoter for T7 RNA polymerase or SP6 RNA polymerase. Accordingly, also provided by this invention is a nucleic acid molecule, i.e., DNA or cDNA, coding for a catalytic polynucleotide of the invention. When the vector also contains an RNA polymerase promoter operably linked to the DNA molecule, the ribozyme can be produced in vitro upon incubation with RNA polymerase and nucleotides. In a separate embodiment, the DNA can be inserted into an expression cassette or transcription cassette. After synthesis, the RNA molecule can be modified by ligation to a DNA molecule having the ability to stabilize the ribozyme and make it resistant to RNase.

As with antisense polynucleotides described herein, catalytic polynucleotides of the invention should also be capable of hybridizing a target nucleic acid molecule (for example an mRNA encoding any polypeptide provided in SEQ ID NOs 1 to 8) under "physiological conditions", namely those conditions within a cell (especially conditions in an animal cell such as a human cell).

RNA Interference

RNA interference (RNAi) is particularly useful for specifically inhibiting the production of a particular protein. Although not wishing to be limited by theory, Waterhouse et al. (1998) have provided a model for the mechanism by which dsRNA (duplex RNA) can be used to reduce protein production. This technology relies on the presence of dsRNA molecules that contain a sequence that is essentially identical to the mRNA of the gene of interest or part thereof, in this case an mRNA encoding a polypeptide according to the invention. Conveniently, the dsRNA can be produced from a single promoter in a recombinant vector or host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules for the present invention is well within the capacity of a person skilled in the art, particularly considering Waterhouse et al. (1998), Smith et al. (2000), WO 99/32619, WO 99/53050, WO 99/49029, and WO 01/34815.

In one example, a DNA is introduced that directs the synthesis of an at least partly double stranded RNA product(s) with homology to the target gene to be inactivated. The DNA therefore comprises both sense and antisense sequences that, when transcribed into RNA, can hybridize to form the double-stranded RNA region. In a preferred embodiment, the sense and antisense sequences are separated by a spacer region that comprises an intron which, when transcribed into RNA, is spliced out. This arrangement has been shown to result in a higher efficiency of gene silencing. The double-stranded region may comprise one or two RNA molecules, transcribed from either one DNA region or two. The presence of the double stranded molecule is thought to trigger a response from an endogenous plant system that destroys both the double stranded RNA and also the homologous RNA transcript from the target plant gene, efficiently reducing or eliminating the activity of the target gene.

The length of the sense and antisense sequences that hybridise should each be at least 19 contiguous nucleotides, preferably at least 30 or 50 nucleotides, and more preferably at least 100, 200, 500 or 1000 nucleotides. The full-length sequence corresponding to the entire gene transcript may be used. The lengths are most preferably 100-2000 nucleotides. The degree of identity of the sense and antisense sequences to the targeted transcript should be at least 85%, preferably at least 90% and more preferably 95-100%. The RNA molecule may of course comprise unrelated sequences which may function to stabilize the molecule. The RNA molecule may be expressed under the control of a RNA polymerase II or RNA polymerase III promoter. Examples of the latter include tRNA or snRNA promoters.

Preferred small interfering RNA ('siRNA') molecules comprise a nucleotide sequence that is identical to about 19-21 contiguous nucleotides of the target mRNA. Preferably, the target mRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the animal (preferably human) in which it is to be introduced, e.g., as determined by standard BLAST search.

microRNA

MicroRNA regulation is a clearly specialized branch of the RNA silencing pathway that evolved towards gene regulation, diverging from conventional RNAi/PTGS. MicroRNAs are a specific class of small RNAs that are encoded in gene-like elements organized in a characteristic inverted repeat. When transcribed, microRNA genes give rise to stem-looped precursor RNAs from which the microRNAs are subsequently processed. MicroRNAs are typically about 21 nucleotides in length. The released miRNAs are incorporated into RISC-like complexes containing a particular subset of Argonaute proteins that exert sequence-specific gene repression (see, for example, Millar and Waterhouse, 2005; Pasquinelli et al., 2005; Almeida and Allshire, 2005).

Cosuppression

Another molecular biological approach that may be used is co-suppression. The mechanism of co-suppression is not well understood but is thought to involve post-transcriptional gene silencing (PTGS) and in that regard may be very similar to many examples of antisense suppression. It involves introducing an extra copy of a gene or a fragment thereof into a plant in the sense orientation with respect to a promoter for its expression. The size of the sense fragment, its correspondence to target gene regions, and its degree of sequence identity to the target gene are as for the antisense sequences described above. In some instances the additional copy of the gene sequence interferes with the expression of the target plant gene. Reference is made to WO 97/20936 and EP 0465572 for methods of implementing co-suppression approaches.

Recombinant Vectors

One embodiment of the present invention includes a recombinant vector, which comprises at least one isolated polynucleotide molecule described herein, and/or a polynucleotide encoding a polypeptide or compound (such as an antibody) as described herein, inserted into any vector capable of delivering the polynucleotide molecule into a host cell. Such a vector contains heterologous polynucleotide sequences, that is polynucleotide sequences that are not naturally found adjacent to polynucleotide molecules of the present invention and that preferably are derived from a species other than the species from which the polynucleotide molecule(s) are derived. The vector can be either RNA or DNA, either prokaryotic or eukaryotic, and typically is a transposon (such as described in U.S. Pat. No. 5,792,294), a virus or a plasmid.

One type of recombinant vector comprises the polynucleotide(s) operably linked to an expression vector. The phrase operably linked refers to insertion of a polynucleotide molecule into an expression vector in a manner such that the molecule is able to be expressed when transformed into a host cell. As used herein, an expression vector is a DNA or RNA vector that is capable of transforming a host cell and of effecting expression of a specified polynucleotide molecule. Preferably, the expression vector is also capable of replicating within the host cell. Expression vectors can be either prokaryotic or eukaryotic, and are typically viruses or plasmids. Expression vectors include any vectors that function (i.e., direct gene expression) in recombinant cells, including in bacterial, fungal, endoparasite, arthropod, animal, and plant cells. Vectors of the invention can also be used to produce the polypeptide in a cell-free expression system, such systems are well known in the art.

"Operably linked" as used herein refers to a functional relationship between two or more nucleic acid (e.g., DNA) segments. Typically, it refers to the functional relationship of transcriptional regulatory element to a transcribed sequence. For example, a promoter is operably linked to a coding sequence, such as a polynucleotide defined herein, if it stimulates or modulates the transcription of the coding sequence in an appropriate host cell and/or in a cell-free expression system. Generally, promoter transcriptional regulatory elements that are operably linked to a transcribed sequence are physically contiguous to the transcribed sequence, i.e., they are cis-acting. However, some transcriptional regulatory elements, such as enhancers, need not be physically contiguous or located in close proximity to the coding sequences whose transcription they enhance.

In particular, expression vectors of the present invention contain regulatory sequences such as transcription control sequences, translation control sequences, origins of replication, and other regulatory sequences that are compatible with the recombinant cell and that control the expression of polynucleotide molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, arthropod, nematode, plant or animal cells, such as, but not limited to, tac, lac, trp, trc, oxy-pro, omp/lpp, rrnB, bacteriophage lambda, bacteriophage T7, T7lac, bacteriophage T3, bacteriophage SP6, bacteriophage SP01, metallothionein, alpha-mating factor, *Pichia* alcohol oxidase, alphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells.

Host Cells

Another embodiment of the present invention includes a recombinant cell comprising a host cell transformed with one or more recombinant molecules described herein or progeny cells thereof. Transformation of a polynucleotide molecule into a cell can be accomplished by any method by which a polynucleotide molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed polynucleotide molecules of the present invention can remain extrachromosomal or can integrate into one or more sites within a chromosome of the transformed (i.e., recombinant) cell in such a manner that their ability to be expressed is retained.

Suitable host cells to transform include any cell that can be transformed with a polynucleotide of the present invention. Host cells of the present invention either can be endogenously (i.e., naturally) capable of producing polypeptides described herein or can be capable of producing such polypeptides after being transformed with at least one polynucleotide molecule as described herein. Host cells of the present invention can be any cell capable of producing at least one protein defined herein, and include bacterial, fungal (including yeast), parasite, nematode, arthropod, animal and plant cells. Examples of host cells include *Salmonella, Escherichia, Bacillus, Listeria, Saccharomyces, Spodoptera, Mycobacteria, Trichoplusia*, BHK (baby hamster kidney) cells, CHO cells, 293 cells, EL4 cells, MDCK cells, CRFK cells, CV-1 cells, COS (e.g., COS-7) cells, and Vero cells. Further examples of host cells are *E. coli*, including *E. coli* K-12 derivatives; *Salmonella typhi; Salmonella typhimurium*, including attenuated strains; *Spodoptera frugiperda; Trichoplusia ni*; and non-tumorigenic mouse myoblast G8 cells (e.g., ATCC CRL 1246).

Recombinant DNA technologies can be used to improve expression of a transformed polynucleotide molecule by manipulating, for example, the number of copies of the polynucleotide molecule within a host cell, the efficiency with which those polynucleotide molecules are transcribed, the efficiency with which the resultant transcripts are translated, and the efficiency of post-translational modifications. Recombinant techniques useful for increasing the expression of polynucleotide molecules of the present invention include, but are not limited to, operatively linking polynucleotide molecules to high-copy number plasmids, integration of the polynucleotide molecule into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of polynucleotide molecules of the present invention to correspond to the codon usage of the host cell, and the deletion of sequences that destabilize transcripts.

Transgenic Plants

The term "plant" refers to whole plants, plant organs (e.g. leaves, stems roots, etc), seeds, plant cells and the like. Plants contemplated for use in the practice of the present invention include both monocotyledons and dicotyledons. Target plants include, but are not limited to, the following: cereals (wheat, barley, rye, oats, rice, sorghum and related crops); beet (sugar beet and fodder beet); pomes, stone fruit and soft fruit (apples, pears, plums, peaches, almonds, cherries, strawberries, raspberries and black-berries); leguminous plants (beans, lentils, peas, soybeans); oil plants (rape, mustard, poppy, olives, sunflowers, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as maize, tobacco, nuts, coffee, sugar cane, tea, vines, hops, turf, bananas and natural rubber plants, as well as ornamentals (flowers, shrubs, broad-leaved trees and evergreens, such as conifers).

Transgenic plants, as defined in the context of the present invention include plants (as well as parts and cells of said plants) and their progeny which have been genetically modified using recombinant techniques to cause production of at least one polypeptide and/or polynucleotide of the present invention in the desired plant or plant organ. Transgenic plants can be produced using techniques known in the art, such as those generally described in A. Slater et al., Plant Biotechnology—The Genetic Manipulation of Plants, Oxford University Press (2003), and P. Christou and H. Klee, Handbook of Plant Biotechnology, John Wiley and Sons (2004).

A polynucleotide of the present invention may be expressed constitutively in the transgenic plants during all stages of development. Depending on the use of the plant or plant organs, the polynucleotides may be expressed in a stage-specific manner. Furthermore, the polynucleotides may be expressed tissue-specifically.

Regulatory sequences which are known or are found to cause expression of a polynucleotide of interest in plants may be used in the present invention. The choice of the regulatory sequences used depends on the target plant and/or target organ of interest. Such regulatory sequences may be obtained from plants or plant viruses, or may be chemically synthesized. Such regulatory sequences are well known to those skilled in the art.

Constitutive plant promoters are well known. Further to previously mentioned promoters, some other suitable promoters include but are not limited to the nopaline synthase promoter, the octopine synthase promoter, CaMV 35S promoter, the ribulose-1,5-bisphosphate carboxylase promoter, Adh1-based pEmu, Act1, the SAM synthase promoter and Ubi promoters and the promoter of the chlorophyll a/b binding protein. Alternatively it may be desired to have the transgene(s) expressed in a regulated fashion. Regulated expression of the polynucleotides is possible by placing the coding sequence under the control of promoters that are tissue-specific, developmental-specific, or inducible. Several tissue-specific regulated genes and/or promoters have been reported in plants. These include genes encoding the seed storage proteins (such as napin, cruciferin, β-conglycinin, glycinin and phaseolin), zein or oil body proteins (such as oleosin), or genes involved in fatty acid biosynthesis (including acyl carrier protein, stearoyl-ACP desaturase, and fatty acid desaturases (fad 2-1)), and other genes expressed during embryo development (such as Bce4). Particularly useful for seed-specific expression is the pea vicilin promoter. Other useful promoters for expression in mature leaves are those that are switched on at the onset of senescence, such as the SAG promoter from *Arabidopsis*. A class of fruit-specific promoters expressed at or during anthesis through fruit development, at least until the beginning of ripening, is discussed in U.S. Pat. No. 4,943,674. Other examples of tissue-specific promoters include those that direct expression in leaf cells following damage to the leaf (for example, from chewing insects), in tubers (for example, patatin gene promoter), and in fiber cells (an example of a developmentally-regulated fiber cell protein is E6 fiber.

Several techniques are available for the introduction of an expression construct containing a nucleic acid sequence of interest into the target plants. Such techniques include but are not limited to transformation of protoplasts using the calcium/polyethylene glycol method, electroporation and microinjection or (coated) particle bombardment. In addition to these so-called direct DNA transformation methods, transformation systems involving vectors are widely available, such as viral and bacterial vectors (e.g. from the genus *Agrobacterium*). After selection and/or screening, the protoplasts, cells or plant parts that have been transformed can be regenerated into whole plants, using methods known in the art. The choice of the transformation and/or regeneration techniques is not critical for this invention.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

Transgenic Non-Human Animals

The transgenic non-human animals of the present invention can be broadly categorized into two types: "knockouts" and "knockins". A "knockout" has an alteration in the target gene via the introduction of transgenic sequences that results in a decrease of function of the target gene, preferably such that target gene expression is insignificant or undetectable. A "knockin" is a transgenic animal having an alteration in a host cell genome that results in an augmented expression of a target gene, e.g., by introduction of an additional copy of the target gene, or by operatively inserting a regulatory sequence that provides for enhanced expression of an endogenous copy of the target gene. The knock-in or knock-out transgenic animals can be heterozygous or homozygous with respect to the target genes.

Techniques for producing transgenic animals are well known in the art. A useful general textbook on this subject is Houdebine, Transgenic animals—Generation and Use, Harwood Academic, (1997).

Heterologous DNA can be introduced, for example, into fertilized mammalian ova. For instance, embryonic totipotent or pluripotent stem cells can be transformed by microinjection, calcium phosphate mediated precipitation, liposome fusion, retroviral infection, electroporation or other means, the transformed cells are then introduced into the embryo, and the embryo then develops into a transgenic animal. In a highly preferred method, developing embryos are infected with a retrovirus containing the desired DNA, and transgenic animals produced from the infected embryo. In another preferred method, however, the appropriate DNAs are coinjected into the pronucleus or cytoplasm of embryos, preferably at the single cell stage, and the embryos allowed to develop into mature transgenic animals.

Another method used to produce a transgenic animal involves microinjecting a nucleic acid into pro-nuclear stage eggs by standard methods. Injected eggs are then cultured before transfer into the oviducts of pseudopregnant recipients.

Transgenic animals may also be produced by nuclear transfer technology. Using this method, fibroblasts from donor animals are stably transfected with a plasmid incorporating the coding sequences for a binding domain or binding partner of interest under the control of regulatory sequences. Stable transfectants are then fused to enucleated oocytes, cultured and transferred into female recipients.

Gene Therapy

Therapeutic polynucleotides molecules described herein may be employed in accordance with the present invention by expression of such polynucleotides in treatment modalities often referred to as "gene therapy". For example, polynucleotides encoding human 5B6 (for example SEQ ID NO:1), or fragment thereof, may be employed in gene therapy techniques for the treatment of disease. Thus, cells from a patient may be engineered with a polynucleotide, such as a DNA or RNA, to encode a polypeptide ex vivo. The engineered cells can then be provided to a patient to be treated with the polypeptide. In this embodiment, cells may be engineered ex vivo, for example, by the use of a retroviral plasmid vector containing RNA encoding a polypeptide described herein can be used to transform, for example, stem cells or differentiated stem cells. Such methods are well-known in the art and their use in the present invention will be apparent from the teachings herein.

Further, cells may be engineered in vivo for expression of a polypeptide in vivo by procedures known in the art. For example, a polynucleotide encoding a polypeptide as described herein may be engineered for expression in a replication defective retroviral vector or adenoviral vector or other vector (e.g., poxvirus vectors). The expression construct may then be isolated. A packaging cell is transduced with a plasmid vector containing RNA encoding a polypeptide as described herein such as human 5B6, such that the packaging cell now produces infectious viral particles containing the gene of interest. These producer cells may be administered to a patient for engineering cells in vivo and expression of the polypeptide in vivo. These and other methods for administering a polypeptide should be apparent to those skilled in the art from the teachings of the present invention.

Retroviruses from which the retroviral plasmid vectors hereinabove-mentioned may be derived include, but are not limited to, Moloney Murine Leukemia Virus, Spleen Necrosis Virus, Rous Sarcoma Virus, Harvey Sarcoma Virus, Avian Leukosis Virus, Gibbon Ape Leukemia Virus, Human Immunodeficiency Virus, Adenovirus, Myeloproliferative Sarcoma Virus, and Mammary Tumor Virus. In a preferred embodiment, the retroviral plasmid vector is derived from Moloney Murine Leukemia Virus.

Such vectors will include one or more promoters for expressing the polypeptide. Suitable promoters which may be employed include, but are not limited to, the retroviral LTR; the SV40 promoter; and the human cytomegalovirus (CMV) promoter. Cellular promoters such as eukaryotic cellular promoters including, but not limited to, the histone, RNA polymerase III, the metallothionein promoter, heat shock promoters, the albumin promoter, the 5B6 promoter, human globin promoters and β-actin promoters, can also be used. Additional viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The retroviral plasmid vector can be employed to transduce packaging cell lines to form producer cell lines. Examples of packaging cells which may be transfected include, but are not limited to, the PE501, PA317, Ψ-2, Ψ-AM, PA12, T19-14×, VT-19-17-H2, YCRE, YCRIP, GP+E-86, GP+envAm12, and DAN cell lines as described by Miller (1990). The vector may be transduced into the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line will generate infectious retroviral vector particles, which include the nucleic acid sequence(s) encoding the polypeptide. Such retroviral vector particles may then be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, myocytes (particularly skeletal muscle cells), endothelial cells, and bronchial epithelial cells.

Genetic therapies in accordance with the present invention may involve a transient (temporary) presence of the gene therapy polynucleotide in the patient or the permanent introduction of a polynucleotide into the patient.

Genetic therapies, like the direct administration of agents discussed herein, in accordance with the present invention may be used alone or in conjunction with other therapeutic modalities.

Pharmaceutical Compositions, Dosages, and Routes of Administration

Compositions comprising a compound that binds 5B6 together with an acceptable carrier or diluent are useful in the methods of the present invention. Also provided are compositions comprising a polypeptide, polynucleotide, vector, plant, extract, cell line and/or host cell of the invention.

Therapeutic compositions can be prepared by mixing the desired component (such as a compound that binds 5B6) having the appropriate degree of purity with optional pharmaceutically acceptable carriers, excipients, or stabilizers (Remington's Pharmaceutical Sciences, 16th edition, Osol, A. ed. (1980)), in the form of lyophilized formulations, aqueous solutions or aqueous suspensions. Acceptable carriers, excipients, or stabilizers are preferably nontoxic to recipients at the dosages and concentrations employed, and include buffers such as Tris, HEPES, PIPES, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride;

phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; sugars such as sucrose, mannitol, trehalose or sorbitol; salt-forming counter-ions such as sodium; and/or non-ionic surfactants such as TWEEN™, PLURONICS™ or polyethylene glycol (PEG).

Additional examples of such carriers include ion exchangers, alumina, aluminum stearate, lecithin, serum proteins, such as human serum albumin, buffer substances such as glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, colloidal silica, magnesium trisilicate, polyvinyl pyrrolidone, and cellulose-based substances.

Therapeutic compositions to be used for in vivo administration should be sterile. This is readily accomplished by filtration through sterile filtration membranes, prior to or following lyophilization and reconstitution. The composition may be stored in lyophilized form or in solution if administered systemically. If in lyophilized form, it is typically formulated in combination with other ingredients for reconstitution with an appropriate diluent at the time for use. An example of a liquid formulation is a sterile, clear, colorless unpreserved solution filled in a single-dose vial for subcutaneous injection.

Therapeutic compositions generally are placed into a container having a sterile access port, for example, an intravenous solution bag or vial having a stopper pierceable by a hypodermic injection needle. The compositions are preferably administered subcutaneously, intravenously, intraperitoneally, intramuscularly or parenterally, for example, as intravenous injections or infusions or administered into a body cavity.

The compound may be administered in an amount of about 0.001 to 2000 mg/kg body weight per dose, and more preferably about 0.01 to 500 mg/kg body weight per dose. Repeated doses may be administered as prescribed by the treating physician.

Single or multiple administrations of the compositions are administered depending on the dosage and frequency as required and tolerated by the patient. The dosage and frequency will typically vary according to factors specific for each patient depending on the specific therapeutic or prophylactic agents administered, the severity and type of disease or immune response required, the route of administration, as well as age, body weight, response, and the past medical history of the patient. Suitable regimens can be selected by one skilled in the art by considering such factors and by following, for example, dosages reported in the literature and recommended in the Physician's Desk Reference, $56^{th}$ ed., (2002). Generally, the dose is sufficient to treat or ameliorate symptoms or signs of disease without producing unacceptable toxicity to the patient.

In another example of the invention, the compound that binds 5B6 is conjugated to antigen, such as a cancer or an antigen of a pathogen or infectious organism, and delivered by intramuscular, subcutaneous or intravenous injection, or orally, as a vaccine to enhance humoral and/or T cell mediated immune responses. In another example, a compound that binds 5B6 conjugated to a self antigen or allergenic antigen can used to deliver antigen in order to diminish immune responses similar to that described for 33D1 and DEC-205 (Bonifaz et al., 2002; Finkelman et al., 1996).

In another example of the present invention, a radiolabeled form of the compound that binds 5B6 is delivered by intravenous injection as a therapeutic agent to target cells that express 5B6. Previous examples of radiolabeled antibodies and the methods for their administration to patients as therapeutics are known to those skilled in the art. Examples include Iodine$^{131}$ labeled Lym-1, against the β subunit of HLA-DR and the anti-CD20 Indium$^{111}$ and Yttrium$^{90}$ labeled Ibritumomab Tiuxetan (IDEC-Y2B8, ZEVALIN®) and Iodine I 131 Tositumomab (BEXXAR®).

In one embodiment, the composition does not comprise an adjuvant. In another embodiment, the composition does comprise an adjuvant. Examples of adjuvants include, but are not limited to, aluminium hydroxide, aluminium phosphate, aluminium potassium sulphate (alum), muramyl dipeptide, bacterial endotoxin, lipid X, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.).

In an embodiment, the composition comprises liposomes or membrane vesicles. Examples of such liposomes are described in US 2007/0026057, Leserman (2004) and van Broekhoven et al. (2004). In these instances the compound of the invention can be used to target the liposome to dendritic cells or precursors thereof, and/or be used to enhance the delivery of, for example, a compound-antigen conjugate to dendritic cells or precursors thereof. As outlined in US 2007/0026047, processes for the preparation of membrane vesicles for use in the invention are described in WO 00/64471.

Compositions for inducing/enhancing an immune response are conventionally administered parenterally, by injection, for example, subcutaneously, intramuscularly or intravenously. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1% to 2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the vaccine composition is lyophilised, the lyophilised material may be reconstituted prior to administration, e.g. as a suspension. Reconstitution is preferably effected in buffer. Capsules, tablets and pills for oral administration to a patient may be provided with an enteric coating comprising, for example, Eudragit "S", Eudragit "L", cellulose acetate, cellulose acetate phthalate or hydroxypropylmethyl cellulose.

In any treatment regimen, the therapeutic composition may be administered to a patient either singly or in a cocktail containing other therapeutic agents, compositions, or the like.

In an embodiment, the immune response is modulated by using a DNA vaccine encoding a compound of the invention conjugated to an antigen. DNA vaccination involves the direct in vivo introduction of DNA encoding the antigen into tissues of a subject for expression of the antigen by the cells of the subject's tissue. Such vaccines are termed herein "DNA vaccines" or "nucleic acid-based vaccines". DNA vaccines are described in U.S. Pat. No. 5,939,400, U.S. Pat. No. 6,110,898, WO 95/20660, WO 93/19183, Demangel et al. (2005) and Nchinda et al. (2008).

To date, most DNA vaccines in mammalian systems have relied upon viral promoters derived from cytomegalovirus (CMV). These have had good efficiency in both muscle and skin inoculation in a number of mammalian species. A factor known to affect the immune response elicited by DNA immunization is the method of DNA delivery, for example, parenteral routes can yield low rates of gene transfer and produce considerable variability of gene expression. High-velocity inoculation of plasmids, using a gene-gun, enhanced the immune responses of mice, presumably because of a greater efficiency of DNA transfection and more effective antigen presentation by dendritic cells. Vectors containing the nucleic acid-based vaccine of the invention may also be introduced into the desired host by other methods known in the art, e.g., transfection, electroporation, microinjection, transduction, cell fusion, DEAE dextran, calcium phosphate precipitation, lipofection (lysosome fusion), or a DNA vector transporter.

Transgenic plants producing a antigenic polypeptide can be constructed using procedures well known in the art. A number of plant-derived edible vaccines are currently being developed for both animal and human pathogens. Immune responses have also resulted from oral immunization with transgenic plants producing virus-like particles (VLPs), or chimeric plant viruses displaying antigenic epitopes. It has been suggested that the particulate form of these VLPs or chimeric viruses may result in greater stability of the antigen in the stomach, effectively increasing the amount of antigen available for uptake in the gut.

Examples

Materials and Methods
Mice
C57BL/6J Wehi, C57/BL6Ly5.1, and the OVA-specific CD8 (OT-I) and CD4 (OT-II) TCR-transgenic C57BL/6 background mice were bred under specific pathogen free conditions at The Walter and Eliza Hall Institute (WEHI). TRIF$^{-/-}$ (Yamamoto et al., 2003) and MyD88$^{-/-}$ (Adachi et al., 1998) backcrossed onto C57BL/6, were interbred to derive TRIF$^{-/-}$MyD88$^{-/-}$double knock-out mice. The FcRγ chain$^{-/-}$ mice, backcrossed onto C57BL/6 (Van de Velde et al., 2006), were obtained from the Burnet Institute, Austin. Female mice were used at 6-12 weeks of age; alternatively, gender aged-matched cohorts were generated. Animals were handled according to the guidelines of the National Health and Medical Research Council of Australia. Experimental procedures were approved by the Animal Ethics Committee, WEHI.

Sequence Identification of 5B6
Sequencing was performed using the Big Dye Terminator version 3.1 (Applied Biosystems, Victoria, Australia) and 200 ng plasmid DNA, and subjected to electrophoresis on an ABI 3730xl 96-capillary automated DNA sequencer. Comparison of sequences to the expressed sequence tag, cDNA and protein databases was performed by basic local alignment search tool (BLAST) using National Center for Biotechnology Information (www.ncbi.nlm.nih.gov). Genomic localisation was performed by BLAT alignment to the mouse assembly (February 2006) and human assembly (March 2006) using University of California Santa Cruz, Genome Browser (www.genome.ucsc.edu/).

Quantitative RT-PCR
RNA (up to 1 µg) was DNase treated with RQ1 DNase (Promega) then reverse transcribed into cDNA using random primers (Promega) and Superscript II reverse transcriptase (Gibco BRL, Geithersburg, Md.). Real-time reverse transcription PCR (RT-PCR) was performed to determine the expression of 5B6 and Gapdh in hemopoietic cells using the Quantitect SYBR Green PCR kit (Qiagen) and a Light cycler (Roche, Victoria; Australia). The specific primers for real-time RT-PCR were as follows: 5B6; 5'-TGTGACT-GCTCCCACAACTGGA-3' (SEQ ID NO:17); 5'-TTTG-CACCAATCACAGCACAGA-3' (SEQ ID NO:18), Gapdh; 5'-CATTTGCAGTGGCAAAGTGGAG-3' (SEQ ID NO:19); 5'-GTCTCGCTCCTGGAAGATGGTG-3' (SEQ ID NO:20). An initial activation step for 15 min at 95° C. was followed by 40 cycles of: 15 s at 94° C. (denaturation), 20-30 s at 50-60° C. (annealing) and 10-12 s at 72° C. (extension), followed by melting point analysis. The expression level for each gene was determined using a standard curve prepared from $10^{-2}$-$10^{-6}$ pg of specific DNA fragment, and was expressed as a ratio relative to Gapdh.

Recombinant Surface Expression of 5B6
Full length mouse and human 5B6 (m5B6 and h5B6) were isolated by PCR amplification from splenic DC cDNA using Advantage cDNA polymerase (Clontech) and the following primers: [5B6: 5'-GCCATTTCTTGTACCAAC-CTACTCCT-3' (SEQ ID NO:21); 5'-CGGTGTGGTATG-GATCGTCACTT-3' (SEQ ID NO:22)], [h5B6: 5'-AGC-CTCCTGTGTGGACTGCTTT-3' (SEQ ID NO:23); 5'-TTCATGGCCCACATTTTGGTTT-3' (SEQ ID NO:24)], and the resultant products were subcloned into pGemT easy plasmid (Promega). m5B6 and h5B6 were expressed on the surface of Chinese hamster ovary (CHO) cells as C-terminal (extracellular) FLAG-tagged proteins and on the surface of mouse EL4 cells as a fusion protein where green fluorescent protein (GFP) was fused to the N-terminal cytoplasmic domain of 5B6. To generate the FLAG tagged proteins, 5B6 encoding cDNA was amplified using Advantage high fidelity polymerase (Clontech), restriction digested with AscI and Mlu-1 and subcloned into a pEF-Bos vector modified to contain the FLAG epitope (kindly donated by Dr T. Willson; WEHI).

CHO cells were co-transfected with the pEF-Bos-5B6 lectin and a pGK-neo plasmid containing the neomycin phosphotransferase gene by electoporation (Gene Pulsar, Biorad, NSW, Australia) and transfectants selected with 1 mg/ml G418 (Geneticin, Life Technologies). 5B6 lectin-positive cells were stained with a rat anti-FLAG mAb, followed by an anti-rat Ig-PE (Caltag), and then isolated by flow cytometric sorting. GFP-tagged proteins were generated by amplifying the 5B6 lectin encoding cDNA, restriction digesting with EcoRI and subcloning into pEGFP-C2 vector (Clontech), before electroporation into EL4 cells and selection with 1 mg/ml G418. 5B6-positive cells were isolated by flow cytometric sorting of GFP positive cells. Full length untagged proteins were generated by amplifying the 5B6 lectin encoding cDNA, restriction digesting with EcoRI and subcloning into a pIRES-Neo vector, before electroporation into CHO cells and selection with 1 mg/ml G418.

Generation of mAb Against C-Type Lectins

Wistar rats were immunised three to four times with 50 µg Keyhole Limpet Hemocyanin (KLH)-conjugated peptide: 5B6 mouse peptide (H-DGSSPLSDLLPAERQRSAGQIC-OH) (SEQ ID NO:29), human peptide (H-RWL-WQDGSSPSPGLLPAERSQSANQVC-OH) (SEQ ID NO:30), or 1×10$^7$ CHO cells expressing 5B6-FLAG at 4 week intervals, and given a final boost 4 days before fusion with Sp2/0 myeloma cells. Hybridomas secreting specific mAb were identified by flow cytometric analysis of supernatants using CHO cells expressing C-type 5B6-FLAG and EL4 cells expressing GFP-5B6. Hybridomas were generated that displayed specific reactivity to each of mouse 5B6 and human 5B6.

In summary, the following mAb were generated and utilised in this study, two rat mAb 24/04-10B4 (from peptide immunisation) and 42/04-42D2 (from CHO-5B6-FLAG immunisation) were raised against mouse 5B6 (m5B6). Two rat antibodies 20/05-3A4 and 23/05-4C6 (from h5B6 peptide immunisation) were raised against h5B6. Rat mAb 24/04-10B4 was also found to recognise human 5B6.

Cloning, Expression and Sequencing of Anti-5B6 Antibody 10B4

Total RNA was isolated from hybridoma 24/04-10B4-24-8-FACS9-5 using the Qiagen RNeasy mini kit (Qiagen) with an on column DNase digestion, as per manufacturer's recommendations. 5' RACE ready cDNA was prepared using the SMART RACE cDNA Amplification kit (Clontech), and the heavy and light chain sequences of the antibodies were amplified using the manufacturer's recommended universal primer and the following gene specific primers (IgG2a gene specific primer: CCAGGGCAGTGCTGGGTGCTT (SEQ ID NO:52), kappa gene specific primer: ACGGGTGAG-GATGATGTCTTATGAACAA) (SEQ ID NO:53), as per manufacturer's recommendations. The resultant PCR fragments were subcloned into pGemTeasy plasmid (Promega) and sequenced. Full length IgG2a heavy chain was amplified using [TAGTAGGAATTCAGCACTGACAACAGAACCT-TAAGCAGTATG (SEQ ID NO:54); TAGTAGCGCGGC-CGCTTTACCAGGAGAGTGGGAGAGACTCTTCTC (SEQ ID NO:55)] and full length kappa chain was amplified using [TAGTAGGAATTCGGCGCGCCTCAAACAG-GCAGGAGGAGCAAGATG (SEQ ID NO:56); TAGTAG-GCGGCCGCACGCGTCTAACACTCATTCCTGTT-GAAGCTCTTGACG ACGGGTGAGGATGATGTCTTATGAACAA (SEQ ID NO:57)] and Hotstar DNA polymerase (Qiagen).

PCR products were gel excised and purified using a Qiaquick spin Gel Extraction kit (Qiagen), digested with EcoRI and NotI enzymes and repurified using a Minelute PCR purification kit (Qiagen). The kappa chain was subcloned into pcDNA 3.1 (Invitrogen). The heavy chain was subcloned into a pcDNA 3.1 vector modified to contain an Ala-Ala-Ala linker fused to soluble Ova cDNA insert in the NotI-XbaI region of pcDNA 3.1 (generated in house). This construct enables the generation of a single fusion protein where the C-terminal region of the heavy chain is fused to an Alanine linker and ova. Plasmid DNA was prepared using the Endo-free Plasmid DNA extraction kit (Qiagen), and plasmids encoding the kappa chain, and the heavy chain linked to Ova were transiently cotransfected into freestyle 293F cells (Invitrogen) as per manufacturer's recommendations. Supernatant was harvested 48 hours after transient transfection and examined for the presence of anti-Clec9A-Ova Ab. The recombinant Ab was checked for its ability to bind to CHO cells stably expressing full length (membrane bound) 5B6, and binding detected using two approaches (1) biotinylated Ova-specific sera (Calbiochem) with Streptavidin PE, and (2) anti-rat Ig PE (Caltag).

Isolation and Flow Cytometric Analysis of DCs

DC isolations from lymphoid organs were performed as previously described (Vremec et al., 2000). Briefly, tissues were mechanically chopped, digested with collagenase and DNAse and treated with ethylenediamine tetraacetic acid (EDTA). Low-density cells were enriched by density centrifugation (1.077 g/cm$^3$ Nycodenz, Axis-Shield, Oslo, Norway). Non-DC-lineage cells were coated with mAb (KT3-1.1, anti-CD3; T24/31.7, anti-Thy1; TER119, anti-erythrocytes; ID3, anti-CD19; and 1A8, anti-Ly6G) then removed using anti-rat Ig magnetic beads (Biomag beads, QIAGEN, Victoria, Australia). Blood DCs were enriched by removing red blood cells (RBC) (0.168M NH$_4$Cl; 5 min at 4° C.) and depletion of irrelevant cells as above, except the mAb cocktail also contained the mAb F4/80. DC-enriched populations were blocked using rat Ig and anti-FcR mAb (2.4G2), then stained with fluorochrome-conjugated mAb against CD11c (N418), CD205 (NLDC-145), CD4 (GK1.5), CD8 (YTS169.4), CD24 (M1/69), 120G8 or CD45RA (14.8), Sirpα (p84) and m5B6 (24/04-10B4-biotin).

cDCs were selected as CD11c$^{hi}$CD45RA$^-$ or CD11c$^{hi}$120G8$^-$; splenic cDC were further subdivided into CD4$^+$cDC (CD11c$^{hi}$CD45RA$^-$CD4$^+$ CD8$^-$), double negative (DN) cDC (CD11c$^{hi}$CD45RA$^-$CD4$^-$CD8$^-$) and CD8$^+$ cDC (CD11c$^{hi}$CD45RA$^-$ CD8$^+$ CD4$^-$); thymic DCs were subdivided into CD8$^-$cDC)(Sirpα$^{hi}$CD8$^{lo}$) and CD8$^{-/-}$cDC (Sirpα$^{lo}$CD8$^{hi}$); and LN cDC were subdivided into CD8$^-$ cDC (CD11c$^{hi}$CD205$^-$CD8$^-$), dermal DC (CD11c$^+$CD205$^{int}$CD8$^-$), Langerhans' cells (CD11c$^+$CD205$^{hi}$CD8$^-$) and CD8$^+$cDC (CD11c$^+$CD205$^{hi}$CD8$^+$), as described previously (Lahoud et al., 2006). pDCs were separated as CD11c$^{int}$CD45RA$^+$ or CD11c$^{int}$120G8$^+$. Biotin staining was detected using streptavidin (SA)-phycoerythrin (PE). The expression of m5B6 on the various DC populations was analysed and compared to isotype control staining (IgG2a, BD Pharmingen, San Diego, Calif., USA). Flow cytometric analysis was performed on an LSR II (Becton Dickinson, Franklin Lakes, N.J., USA), excluding autofluorescent and propidium iodide (PI) positive dead cells.

Isolation and Flow Cytometric Analysis of Human Blood DCs and Hemopoietic Cells

Peripheral blood mononuclear cells (PBMC) were isolated from human blood using Ficoll-Pacque-PLUS (GE Healthcare, Rydalmere, NSW, Australia) density separation. Blood donors gave with informed consent and collection was approved by Human Research Ethics Committee, Melbourne Health. The PBMC were blocked using rat Ig and anti-FcR mAb (2.4G2) then stained with mAb against HLA-DR (L243; Becton Dickinson), and a cocktail of PE-conjugated mAb against lineage markers, namely CD3 (BW264156; T cells), CD14 (Tuk4; monocytes), CD19 (6D5; B cells) and CD56 (AF12-7H3; NK cells). Blood DCs were gated as HLA-DR$^{hi}$, lineage$^-$ cells and further segregated based on their expression of BDCA-1 (ADJ-8E3), BDCA-3 (AD5-14H2), BDCA-4 (AD5-17F6) and CD16 (VEP13). PBMC were also used as a source of other hemopoietic cells that were isolated using mAb against CD3 (BW264156; T cells), CD19 (6D5; B cells), CD56 (AF12-7H3), and NKp46 (9E2) (CD56$^+$NKp46$^+$; NK cells) and CD14 (Tuk4; monocytes). Staining and flow cytometric analysis for the expression of h5B6 (20/05-3A4) was performed, excluding PI positive dead cells. Unless otherwise specified, all anti-human mAb were purchased from Miltenyi Biotec (North Ryde, NSW, Australia).

Isolation and Analysis of 5B6 on Mouse Hemopoietic Cells

Spleen cell suspensions were prepared as for DC isolation (Vremec et al., 2000). Cells were stained with mAb against CD3 (KT3-1.1), CD19 (ID3), NK1.1 (PK136), CD49b (Hmα2; eBioscience, San Diego, Calif., USA) then B cells (CD19$^+$CD3$^-$), T cells (CD19$^-$CD3$^+$) and NK cells (CD49b$^+$NK1.1$^+$CD3$^-$) were selected. Splenic macrophages were first enriched by a 1.082 g/cm$^3$ density centrifugation (Nycodenz) and immunomagnetic bead depletion of CD3$^+$ T cells and CD19$^+$ B cells; the enriched cells were stained with mAb against CD11b (M1/70) and F4/80, then macrophages were gated as CD11b$^{hi}$F4/80$^+$. Bone marrow macrophages and monocytes were first enriched as for spleen, then stained with CD11b (M1/70) and Ly6C (5075-3.6); monocytes were then gated as side-scatter$^{lo}$Ly6C$^{hi}$CD11b$^{hi}$ and macrophages as Ly6C$^{int}$CD11b$^{hi}$. All cells were blocked using rat Ig and anti-FcR mAb (2.4G2) before immunofluorescence staining with the various mAb cocktails including anti-5B6 mAb (10B4-biotin). Biotin staining was detected using streptavidin-PE. Samples were analysed for their expression of 5B6 on an LSR II (Becton Dickinson), excluding PI positive dead cells.

Immunisation Using Anti-5B6 mAb

Mice (C57BL6 or TRIF$^{-/-}$MyD88$^{-/-}$ mice) were immunised subcutaneously (s.c.) or intravenously (i.v.) with 10 μg of rat anti-5B6 mAb (10B4) or isotype control mAb 1 (IgG2a, eBioscience) or isotype control mAb 2 (IgG2a,-antiβ-Gal, GL117). Serum samples were obtained at 2-8 weeks and the level of anti-rat Ig reactivity determined by ELISA. The anti-5B6 mAb and GL117 control mAb, were also chemically conjugated to ovalbumin (OVA). Conjugates are chromatographically purified to remove free OVA and unconjugated mAb. The desired ratio of mAb to OVA is 1:1, which is validated by SDS-PAGE and Coomasie blue staining. Their continued capacity to recognise target Ag is verified by staining transfected cell lines with conjugates and detecting binding using biotinylated OVA-specific sera (Calbiochem) followed by streptavidin-PE. C57BL6 mice were immunised with 2.5-10 μg of 10B4-OVA (anti-5B6 mAb conjugated to OVA) or control -OVA (isotype control GL117 mAb conjugated to OVA).

ELISA for the Detection of Serum Ab

ELISA plates (Costar, Broadway, Cambridge, UK) were coated overnight at 4° C. with 2 μg/ml of rat GL117 mAb. Unbound mAb was washed away (PBS, 0.05% Tween-20). Serially diluted serum samples were plated (PBS/5% milk powder) and incubated at 4° C. overnight. Bound mouse anti-rat Ig antibodies were detected using donkey anti-mouse IgG HRP (Chemicon International, Temecula, Calif., USA) and visualised using ABTS. Titers were considered positive when the optical density was over 0.1. The isotype of the anti-rat response was assayed as above, but detected using anti-mouse IgG1-, IgG2b-, IgG2c- and IgG3-HRP conjugates (1/4000) (Southern Biotech, Birmingham, Ala., USA). Anti-OVA responses were assayed by coating plates with 10 μg/ml OVA, and anti-rat Ig antibodies were detected as above.

Antigen Presentation Assay

Mice immunised with 10 μg of 10B4-OVA (anti-5B6 mAb conjugated to OVA) and GL117-OVA were sacrificed one day later and spleens were extracted. DC were isolated from the spleens as described elsewhere (Vremec et al., 2000) and CD8$^+$ or CD8$^-$ DC purified by flow cytometry.

Purification of Transgenic T Cells and In Vivo Proliferation Assays

Transgenic T cells were purified and labeled with carboxy fluorescein diacetate succinmidyl ester (CFSE) (Caminschi et al., 2006). CFSE-labeled cells (10$^6$) were injected i.v. into C57BL6Ly5.1 mice. Three days later, spleens were removed, cell suspensions prepared and purged of RBC, then stained with mAb against CD4 (GK1.5-APC) or CD8 (YTS169-APC) and Ly5.2 (S.450-15.2-PE). Proliferating OT-II (CD4$^+$Ly5.2$^+$) or OT-I (CD8$^+$Ly5.2$^+$) cells were visualized by the loss of CFSE fluorescence and enumerated by addition of a fixed number of calibration beads (BD Pharmingen). Dead cells were excluded using PI. Analysis was carried out on a FACSCalibur instrument (Becton Dickinson).

CFSE Labelled T Cell Proliferation Assays

Purified OT-I cells were washed once in 0.1% BSA/PBS, then resuspended at 1×10$^7$ cell/ml. CFSE (5 mM) was added (1 μl/10$^7$ cells) and cells were incubated at 37° C. for 10 min. RPMI-1640 medium containing 2.5% FCS was added, and cells washed twice. T cells (5×10$^4$ cells/well) were incubated with DC (10$^4$ cells, or as otherwise stated) in U-bottom 96-well plates in 200 μl DC culture medium (modified RPMI-1640 medium containing 10% FCS, 100 U/ml penicillin, 100 μg/ml streptomycin, 10$^{-4}$ M mercaptoethanol). To enumerate T cells after culture, 2.5×10$^4$ calibration beads (BD Bioscience Pharmingen) were added per well, and T cells were visualized by staining with appropriate markers (anti-TCR-Vα2 mAb (B20.1-PE, Pharmingen). Dead cells were excluded using propidium iodide. Analysis was carried out on a FACScan or FACScalibur (Becton Dickinson). Proliferating T cells were identified by loss of CFSE fluorescence and enumerated relative to the beads, so allowing a count of total proliferating T cells per well.

Recombinant Expression of Soluble 5B6

To generate soluble 5B6, cDNA containing the hinge and ectodomain regions was amplified using Advantage high fidelity 2 polymerase (Clontech) and the following primers [m5B6: 5'-TAGTAGACGCGTGAGCAGCAG-GAAAGACTCATC-3' (SEQ ID NO:25); 5'-TAGTA-GACGCGTTCAGATGCAGGATCCAAATGC-3'] (SEQ ID NO:26), [H5B6:5'-TAGTAGACGCGTCAGCAG-CAAGAAAAACTCATC-3' (SEQ ID NO:27); 5'-TAGTA-GACGCGTTCAGACAGAGGATCTCAACGC-3'] (SEQ ID NO:28). The amplified cDNA was restriction digested with Mlu-1 and subcloned into the Mlu-1 site of a pEF-Bos vector modified to contain the biotinylation consensus sequence (a peptide consensus sequence NSGLH-HILDAQKMVWNHR (SEQ ID NO:31) recognised specifically by E. coli biotin holoenzyme synthetase BirA and the FLAG epitope. The resulting lectin fusion constructs thus included (in order of N-terminus): the IL3 signal sequence (to ensure secretion), the biotinylation consensus peptide sequence, a FLAG-tag, the hinge region and the lectin domain. Recombinant proteins were expressed by transient transfection of 293T cells (a human renal epithelial cell line stably transfected with polyoma/SV40 large T antigen) in DMEM-10% FCS with 8 micrograms DNA/75 cm2 flask using Fugene. After 8 h, the media was removed, the cells washed twice, then incubated for 36-60 h in 10 ml X-Vivo-10 protein-free/serum-free media (BioWhittaker, Walkersville, Md.). The media containing the secreted recombinant protein was harvested, and recombinant protein from the culture supernatant concentrated 100-fold using a 10,000 mwt cutoff centrifugal device (Nanosep 10K Omega, PALL Life Sciences). The concentrated protein was then used directly or enzymatically biotinylated using BIR enzyme (Avidity, Denver, Colo.).

Binding Assays Using Soluble 5B6

293T cells were transiently transfected with expression constructs encoding fall length untagged 5B6 in pIRES Neo.

Two-three days later, cells were harvested and surface immunofluorescence labeled using either (1) soluble FLAG-tagged biotinylated m5B6, h5B6 and Cire, and detected with Streptavidin PE, or (2) soluble FLAG-tagged 5B6, biotinylated anti-FLAG mAb 9H10, and Streptavidin-PE. Live cells were gated on forward and side scatter, or by propidium iodide exclusion and analysed for their surface binding of soluble 5B6. The specificity of the binding of soluble 5B6 was demonstrated by comparison to binding to other soluble FLAG-tagged C-type lectins, such as Cire.

ELISA

Recombinant soluble protein secretion was assayed by capture/two-site ELISA. Briefly, 96-well polyvinylchloride microtitre plates (Costar, Broadway, Cambridge, UK) were coated with purified capture mAb, namely, anti-FLAG 9H10 12.5 ug/ml (generated in-house). Culture supernatants were detected using the biotinylated anti-m5B6 antibody (24/04-10134)-(2 ug/ml), Streptavidin-HRP and ABTS substrate. Biotinylated recombinant soluble protein was assayed by capture/two-site ELISA. Briefly, 96-well polyvinylchloride microtitre plates (Costar, Broadway, Cambridge, UK) were coated with purified capture mAb, namely, anti-FLAG 9H10 12.5 ug/ml (generated in-house). Culture supernatants were detected using Streptavidin-HRP and ABTS substrate.

Generation of Flt3 Ligand Cultured DC

Bone marrow (BM) cells were flushed from the femur and tibia bones, and erythrocytes lysed by brief exposure to 0.168M NH4Cl. Cells were resuspended in 10 mL DC culture medium (modified RPMI-1640 medium containing 10% FCS, 100 U/ml penicillin, 100 µg/ml streptomycin, $10^{-4}$ M mercaptoethanol), and washed by centrifugation 2-3 times. The cell suspension was passed through a sieve. Cells were centrifuged and resuspended in DC culture medium at $1.5 \times 10^6$ cells/mL. Flt3L (FL) was added at a concentration of 200-300 ng/mL. After 8 days of culture, cells were harvested and stained with antibodies against CD11c (N418-PE.Cy7), Sirpα (p84-FITC), CD45RA (14.8-PE) and 5B6 (10B4-APC).

Precursor Isolation from Bone Marrow

BM cells were prepared as described above, and resuspended in 5 mL Nycodenz medium (Nycomed Pharma) at 1.086 g/cm$^3$. The cell suspension was layered onto 5 mL of fresh Nycodenz medium of the same density, and a further 2 mL of FCS layered onto the cell suspension. After centrifugation at 2900 rpm for 10 minutes, the light density cells were isolated and coated with antibodies against lineage antigens—CD2, CD3, CD8, CD45R, CD11b, TER119 and Ly6G—and incubated with polyclonal sheep anti-rat IgG magnetic biomag beads (Qiagen) at a ratio of 8 beads/cell. Beads were removed using a magnet (Dynal), and the unbound fraction stained with monoclonal antibodies (mAb) against CD117 (ACK-2-FITC), stem cell antigen-1 (sca-1; E13 161-7-Alexa Fluor 680) and CD34 (RAM34-biotin; visualised with streptavidin-PE) or CD117 (ACK-2-FITC), CD135 (A2F10-PE), and CD115 (AFS98-biotin; visualised with streptavidin-PerCP.Cy5.5). Multipotent progenitors were isolated as the CD117$^+$ Sca-1$^+$ CD34$^+$ fraction.

DC Precursor Isolation from Culture

BM was extracted and cultured as described, at a concentration of $3 \times 10^6$ cells/mL. Prior to culture, cells were labelled with CFSE (Molecular Probes). CFSE labelling was performed as described previously. Briefly, cells were washed twice by centrifugation in PBS-BSA, and resuspended at a concentration of $1 \times 10^7$ cells/mL. CFSE was added to the cell suspension to a final concentration of 0.5 µM, and the solution incubated for 10 minutes at 37° C. with intermittent mixing. Cells were then washed twice and resuspended in DC culture medium.

After 3.5 days of culture, cells were harvested and light density cells isolated by centrifugation in Nycodenz medium (1.086 g/cm$^3$) as described above. These cells were coated with biotinylated antibodies against lineage antigens (CD19, CD127, MHC class II, Ly6G and TER119) and incubated with anti-biotin magnetic beads. Bound cells were isolated using a MACS magnetic column (Myltenyi). The depleted fraction was incubated with streptavidin-PerCP.Cy5.5 to visualise any remaining lineage$^+$ cells. After washing, cells were stained with combinations of mAb against CD11c (N418-PE.Cy7) and 5B6 (10B4-APC). Pre-DC were isolated as CFSE$^{low}$ lin$^-$ CD11c$^+$ cells.

Results

Comparison of Gene Expression Patterns Between Splenic DC Subsets

Gene expression profile analysis identified a murine cDNA clone that is preferentially expressed by the CD8$^+$ cDC subset relative to the CD8$^-$ cDC. This clone, termed 5B6, represented a fragment of a "hypothetical C-type lectin", a gene found on chromosome 6, that was differentially expressed in CD8$^+$ DC (Riken 9830005G06, (recently named C-type lectin domain family 9, member A, (Clec9a) Genbank accession AK036399.1, Unigene ID Mm.391518). Furthermore, analysis of the public databases revealed a human orthologue for 5B6 (HEEE9341) on chromosome 12, recently renamed CLEC9A (Genback accession NM_207345). Orthologs have been identified to exist in other animals such as chimpanzees (Genbank accession XP_001143778), Rhesus monkeys (XP_001114857), dogs (Genbank accession XP_854151), cows (XP_873119), horses (XP_001493987) and rats (Genbank accession XP_578403).

Identification, Characterisation and Cloning of the C-Type Lectins

The inventors amplified the full-length cDNA encoding mouse and human 5B6 by PCR and sequenced the genes (FIGS. 1A and 1B).

The full-length coding sequence of mouse 5B6, encoded by 7 exons spanning 13.4 kb of genomic DNA (FIG. 1D), contains a single open reading frame (ORF) (795 bp) encoding a protein of 264 amino acid (aa) (FIG. 1C). Human 5B6 coding sequence, is encoded by 6 exons spanning 12.9 kb of genomic DNA (FIG. 1D), similarly contains a single ORF encoding a protein of 241 aa (FIG. 1C).

The mouse and human 5B6 gene each encode a putative transmembrane protein with a single C-type lectin domain in its extracellular region, a cytoplasmic tail and a transmembrane region containing the YXXL residues, which is a potential signalling motif (Fuller et al., 2007) (FIG. 1C). Human 5B6 has shorter hinge region than mouse. An alignment of the mouse and human protein sequences is demonstrated in FIG. 1C (53% identical; 69% similar). A schematic representation of the proposed mouse and human 5B6 protein structure is shown in FIG. 1E.

Using NCBI Blast protein analysis, it was determined that m5B6 shares most sequence similarity with mouse Dectin-1 (Clec7A), Clec12B, and NKG2D, whereas h5B6 is most similar to LOX-1 (Clec8A), Clec12B, and DCAL-2 (Clec12A). The CTLD of 5B6, like the classical C-type lectin the rat mannose binding protein A (MBP-A), has four conserved cysteine residues that form two disulfide bonds (FIG. 2). Furthermore, 5B6 possesses two additional cysteine residues in the neck region that may enable protein homodimerization (Weis et al., 1998). Critically, the residues involved in Ca$^{2+}$ binding in classical C-type lectins are not present in mouse and human 5B6 (FIG. 2).

Gene Expression of Mouse 5B6

Microarray analysis predicted 5B6 to be expressed at 3.5 fold higher levels in CD8$^+$ DC relative to CD8$^-$ DC, and at 2.6-fold higher levels in CD8$^+$ DC relative to the DN DC. Hence, the inventors designed primers and investigated the expression of 5B6, by quantitative RT-PCR, in mouse splenic cDC subsets. It was confirmed that 5B6 was preferentially expressed by the CD8$^+$ cDC; splenic CD8$^+$ DC expressed 22-fold more mRNA than splenic CD4$^+$ cDC (FIG. 3A).

The inventors examined the expression of mouse and human 5B6 genes across a panel of haemopoietic cell types by quantitative real-time RT-PCR. 5B6 mRNA expression was specific to DC, both cDC and pDC, with moderate levels of mRNA expression in NK cells (FIG. 3B). It was preferentially expressed in splenic CD8$^+$ DC relative to CD8$^-$ cDC. It was also differentially expressed in the thymic CD8$^+$ cDC and the LN CD8$^+$DEC205$^{hi}$ cDC (FIG. 3A). Furthermore, the gene expression in all three splenic cDC populations was reduced 3 h after in vivo activation with CpG and LPS, ligands to Toll like receptor 9 and 4 respectively (FIG. 3C).

Surface Expression of Mouse 5B6 Protein

To investigate the protein expression of m5B6 and h5B6, the present inventors generated mAbs that recognised protein on the surface of 5B6-transfected cells by flow cytometry. Staining of a panel of freshly isolated mouse hemopoietic cells with the mAb 10B4 indicated that m5B6 was expressed on a subset of cDCs and on most pDCs (FIG. 4A). Strikingly, m5B6 protein was not detected on most other hemopoietic cells investigated, including T cells, most B cells, monocytes and macrophages. Nor was it detected on the NK cells that expressed some mRNA (FIG. 4A). However, a small (3%) proportion of B cells, displayed clear positive staining for m5B6. Only around 3% of bone marrow cells showed any staining with 10B4, and most of this was weak. Thus, in the hemopoietic system, m5B6 surface expression appears mainly restricted to DCs (FIG. 4A). In addition, staining of frozen sections with the mAb 10B4 revealed no staining beyond that attributed to DCs (data not shown).

Surface levels of m5B6 were then compared on splenic, LN and thymic cDCs. m5B6 was expressed by the CD8$^+$ cDCs of spleen, thymus and LN (FIG. 4A). Most splenic, thymic and LN CD8$^-$cDCs and the migratory cDCs (dermal DCs and Langerhans' cells) were negative for m5B6 expression (FIG. 4A, B). However, a small proportion of CD8$^-$ cDCs showed above background staining; this could be attributed to a small proportion of DCs of the CD8$^+$cDC lineage not yet expressing CD8α, known to be present within this CD8$^-$cDC gating. No m5B6 staining was detected on a preparation of inflammatory CD11c$^{int}$CD11b$^{hi}$ DCs from inflamed mouse spleens (Naik et al., 2006) (data not shown). These DC surface expression profiles were consistent with the gene expression observed by quantitative RT-PCR (FIG. 3).

Surface Expression of Mouse 5B6 on Mouse Blood DC

Mouse blood contains very few mature DC (CD11c$^{hi}$) compared to the DC found within the spleen and these few blood DC lack the expression of CD8 (O'Keeffe et al., 2003). However, in the mouse, CD24 expression has correlated with the expression of CD8. A small portion of mature DC within the blood express this marker; presumably these cells are on their way to becoming CD8$^+$. To determine the expression of 5B6 on blood DC, the present inventors isolated and stained them with CD24 and 5B6. DC expressing CD24 (which are destined to become CD8$^+$ DC) also express 5B6 (FIG. 4C).

Surface Expression of Macaque and Human 5B6

To investigate the surface expression of human 5B6 (h5B6), the present inventors generated two monoclonal antibodies (20105-3A4; 23/05-4C6) that recognised native protein on the surface of h5B6-transfectant cells, as measured by flow cytometry (data not shown). Staining of freshly isolated peripheral blood cells, from humans or from macaque monkeys, indicated that 5B6 was expressed on a subset of DC (FIG. 5). In particular, a small subset of HLADR$^+$ DCs were positive for h5B6 (FIG. 5A). Most other human blood cells did not show positive staining, but low level staining was obtained on human blood B cells (FIG. 5B). To determine if the 5B6-expressing DCs resembled those seen in mouse blood, the blood DCs were also stained with BDCA-1, BDCA-3 and BDCA-4. Staining with mAb 3A4 or 4C6 was restricted to the minor BDCA-3$^+$ DC subset (proposed equivalents of mouse CD8$^+$ cDC), and absent from BDCA-4$^+$ subset (data not shown). This suggests h5B6 is present on a cDC type similar to the mouse CD24$^+$, CD8$^+$ DC lineage (Galibert et al., 2005), but in contrast to the mouse, not on pDCs.

Furthermore, the anti-mouse 5B6 Ab (10B4) was found to bind to h5B6. Both h5B6 on the surface of transfectant cells (data not shown) and on human BDCA-3+ DC, could be detected using the anti-mouse 5B6 mAb (10B4), albeit at lower levels than observed with the anti-h5B6 Ab (4C6) (FIG. 5C).

Role of 5B6 in Immune Modulation

Ab that target Ag to certain DC surface molecules can modulate immune responses (Bonifaz et al., 2002; Finkelman et al., 1996; Carter et al., 2006). It has previously been demonstrated that Ab to the surface molecules Fire, expressed on CD8$^-$ DC, enhance humoral immunity and that, in contrast to other studies on DC targeting, this enhancement did not require additional adjuvant or danger signal (Corbett et al., 2005). Unfortunately Fire does not have a human counterpart that is expressed on the cell surface (Caminschi et al., 2006), but 5B6, which is common to mouse and man, does offer the possibility of human application. Accordingly the effects of targeting antigen to DC via 5B6 were investigated. To exclude the possibility that contaminating LPS (endotoxin) was acting as an adjuvant in the immunizations, all mAbs used in these experiments were tested for LPS contamination and were found to be below the detection limit (1 EU/ml). This is more than one log below the 20 ng of LPS required to enhance immunity to isotype control mAbs (data not shown).

To determine whether Ab to 5B6 could be used to modulate humoral responses, mice were immunised intravenously with 10 μg anti-5B6 (10B4), or with non-targeted isotype control (GL117) mAb. The rat IgG2a is antigenic in mice, as the targeting mAb itself includes foreign antigenic determinants. Accordingly, the effects of DC targeting on the immune response can be assessed by measuring anti-rat IgG response in an ELISA assay. In this assay, the non-targeted Ab (GL117) is used as coating Ag, so any non-specific binding bias will be for the non-targeted immunogen.

The injection of the anti-m5B6 mAb 10B4 alone, without any additional DC activation agents, produced a striking and prolonged anti-rat Ig response (FIG. 6). Around 2 μg of 10B4 produced an optimal response, but as little as 16 ng gave a detectable titer (FIG. 6A, B). The response to 10 μg of targeting mAb was around 5000-fold higher than 10 μg of a non-targeting isotype control mAb. To obtain a significant anti-rat Ig titer, at least a 3000-fold higher level of non-targeting rat Ig was required, compared to the targeted mAb (FIG. 6A, B). Furthermore, once the anti-rat reactivity was established using the targeting anti-5B6 mAb, non-targeting isotype control rat Ig gave a significant boost, suggesting a memory response had been generated (FIG. 6C). The anti-rat Ig response induced by 5B6 targeting was dominated by the IgG1 isotype, but involved other isotypes including a significant IgG2c component (FIG. 6D).

The Anti-5B6 mAb can be Used to Deliver Ag to CD8 DC

A striking feature of the enhanced antibody responses obtained by targeting Ag to m5B6 on DCs was that no additional DC activation agents or adjuvants were employed (FIG. 6, 7A, B, C). The 10B4 mAb used was prepared under "endotoxin-free" conditions and the concentrated mAb contained no detectable endotoxin (less than 1 EU/ml). To confirm that the enhanced antibody response was not due to traces of endotoxin or other microbial products, the experiments were repeated using MyD88$^{-/-}$TRIF$^{-/-}$ mice, which are unable to respond to Toll-like receptor (TLR) ligands. The induction of equivalent, potent antibody responses to rat Ig by injection of mAb to m5B6 was also seen in these mice (FIG. 7A), indicating the response was independent of "danger" signals mediated by TLR ligands. When lipopolysaccharide (LPS) was deliberately injected along with the targeting anti-5B6 mAb, the antibody response was sometimes further enhanced (FIG. 7D) but sometimes not (FIG. 7E).

A possible reason for the enhanced responses might have been the binding of the anti-m5B6 mAb to FcR, as well as to m5B6 itself. This possibility was eliminated by injection of the 10B4 mAb into FcR γ chain deficient mice that cannot signal through activating Fc γRI or Fc γRIII$^{34}$ (FIG. 7B). These gave anti-rat Ig responses identical to control mice.

Since the enhancement of the humoral responses was obtained by a targeting strategy designed to deliver Ag to DCs, it was assumed the enhancement was mainly due to the activation of Ag-specific, CD4$^+$ helper T cells. However, since some B cells expressed a little 5B6, direct targeting to B cells could not be excluded. The role of T cells was tested by injecting the anti-5B6 mAb 10B4 into nude mice, which lack thymic derived T cells. The enhanced antibody response to rat Ig was eliminated (FIG. 7C), showing it was dependent on helper T cells.

The anti-5B6 mAb can also serve to deliver a chemically-linked OVA Ag and enhance the anti-OVA antibody response; an injection of a 400-fold higher level of free OVA was required to produce a positive anti-OVA titer and this was still several magnitudes lower than the titer induced by targeting OVA to DC via anti-5B6 mAb (FIG. 7E, F).

Anti-5B6 Ab is Highly Effective at Antigen Delivery Via Different Routes of Administration and in the Presence or Absence of Adjuvants The inventors compared the effects of targeting antigen to 5B6 (Clec9A) on humoral responses, via different routes of administration. Intravenous, subcutaneous and intraperitoneal administration of anti-5B6 Ab (10B4) all significantly enhanced humoral responses to rat Ig, whereas minimal responses were observed using the isotype control Ab (GL117) (FIG. 10A). Furthermore, targeting antigen to 5B6 induced potent humoral responses in the absence of adjuvants. To determine if the co-administration of adjuvant could further increase the antibody responses generated, mice were injected intravenously with anti-5B6 (10B4) mAb or isotype control (GL117) and LPS (1 µg), or CpG (10 µg). Targeting antigen with 10B4 was found to induce strong humoral responses with or without adjuvants, however, the addition of adjuvants appeared to enhance the primary humoral response and the subsequent memory response, albeit only slightly (FIG. 10B). Thus, targeting antigen to 5B6 using anti-5B6 mAb may be successfully used with or without adjuvant. Vaccine strategies can be designed accordingly/depending upon the pathogen or antigenic material to be vaccinated against and the type of response required.

Enhanced T Cell Responses on Targeting m5B6

To directly determine if T cell responses to a specific Ag were enhanced by targeting Ag to 5B6, a small number of CFSE-labeled, OVA-specific, CD8 (OT-I) or CD4 (OT-II) transgenic T cells were adoptively transferred into C57BL/6 mice, which were then immunised with OVA-conjugated anti-m5B6 (10B4) or with OVA-conjugated isotype control mAb (GL117). Three days later the proliferative response of the transferred Ag-specific T cells was enumerated as the reduction in CFSE fluorescence. Immunising mice with the non-targeting control OVA-conjugated mAb failed to induce OT-I or OT-II proliferation, indicating insufficient Ag was presented to activate these T cells. By contrast, immunising mice with anti-m5B6-OVA mAb conjugate induced extensive proliferation of both OT-I and OT-II T cells (FIG. 8). Ag targeted to m5B6 resulted in enhanced activation of both CD4 and CD8 T cells.

CD8$^+$ DC, which express the 5B6 molecule on their cell surface, activated naïve OT-I cells into proliferation, whereas the CD8$^-$ DC did not (FIG. 9), proving that immunisation with the anti-5B6 mAb (10B4-OVA) successfully shuttled the OVA Ag to the CD8$^+$ DC subset.

Does Binding to m5B6 Activate DCs

Since no additional DC activating agents or adjuvants were required to obtain enhanced antibody responses or T cell responses on targeting Ags to DCs with anti-m5B6, it was possible that DC activating signals could be provided by 5B6 itself. To check if the DCs were activated, they were isolated from the spleens and LN of mice immunised with the targeting anti-5B6 mAb 10B4, and from non-immunised control mice. The DCs were stained with DC subset segregating markers, together with antibodies for the DC maturation markers MHC class II, CD80, CD86 and CD40. There was no evidence of any increase in any of these markers of DC activation in any DC subset, including the CD8$^+$ cDCs, which are the primary targets for the mAb (data not shown). Targeting Ags to 5B6 appeared to enhance immune responses without the normal signs of DC activation.

Soluble 5B6 can Interact with Membrane Bound 5B6 in a Cross-Species Manner

To identify binding partners for the 5B6 molecule, the inventors generated soluble FLAG-tagged m5B6 and h5B6 which encompassed the ectodomain of 5B6 including the stalk region and the C-type lectin-like domain (CTLD), denoted in FIG. 11A as "Original (with stalk)". A soluble FLAG-tagged ectodomain version of the C-type lectin Cire was also generated as a control molecule. Soluble 5B6 (with stalk and CTLD) was screened for binding to 293T cells expressing membrane bound m5B6 and h5B6 following transient transfections with full length untagged 5B6 constructs in a pIresNeo vector. Soluble mouse 5B6 was able to bind to live 293T cells expressing both the membrane bound mouse 5B6 and human 5B6 but showed minimal or no binding to the mock (no DNA) transfected 293T cells (FIG. 11B). Similarly, soluble human 5B6 was able to bind to live 293T cells expressing both the membrane bound mouse 5B6 and human 5B6 but showed no binding to mock transfected 293T cells. In contrast the control soluble molecule Cire showed only minimal binding to the control or transfectant cell lines. Thus, soluble 5B6 can interact with membrane bound 5B6 in a cross-species manner.

To further characterise this interaction, the inventors generated biotinylated soluble FLAG-tagged m5B6 and h5B6 which included the CTLD of 5B6 but did not include the stalk region, denoted in FIG. 11A as "Soluble protein-2/3 (no stalk)". Soluble mouse and human 5B6 were both able to bind to live CHO cells expressing membrane bound mouse 5B6 but showed minimal or no binding to the untransfected CHO cells (FIG. 11C). In contrast the control soluble molecule Cire showed only minimal binding to the control or transfectant cell lines. The binding of soluble 5B6 to membrane bound 5B6 was detected using both the original 5B6 protein (stalk+CTLD), and the soluble 2/3 protein (CTLD only, no stalk), indicating that the CTLD of 5B6 can mediate cross species interaction with membrane bound 5B6.

Surface Expression of Mouse 5B6 on DC Precursors

The present inventors investigated the surface expression on a panel of haemopoietic and DC precursors. Surface expression of 5B6 was not detected on early, uncommitted multipotent progenitors, which retain developmental potential for all haematopoietic lineages. In contrast, the immediate precursors which are capable of generating DC in culture or on transfer into irradiated recipients, the pre-DC, showed low levels of 5B6 expression. 5B6 expression was detected on Flt3 ligand generated Sirpα$^-$ cDC, (functionally equivalent to ex vivo CD8+ cDC (Naik et al., 2005)) and on pDC, but not on Sirpα$^+$ cDC from the same cultures (FIG. 12).

Cloning, Expression and Sequencing of Anti-5B6 Antibody 10B4

The present inventors cloned the heavy and light chains of the anti-5B6 Ab 10B4, and further subcloned the heavy and light chains into individual expression vectors. This allowed the generation of kappa chains and single fusion protein heavy chain where the C-terminal region of the heavy chain was fused to an Alanine linker and ova. Recombinant Ab was produced by transient transfection of freestyle 293F cells.

The amino acid sequence of the heavy (SEQ ID NO:42) and light (SEQ ID NO:47) chains of mAb 24/04-10B4 were determined by sequencing the corresponding genes.

The capacity of the anti-5B6-Ova recombinant Ab to recognise 5B6 was confirmed by labeling CHO-5B6 transfectant cells with the recombinant Ab, and detection using both anti-Ova and anti-rat Ig reagents. The recombinant Ab was demonstrated to bind to CHO-5B6 cells (FIG. 13) whereas minimal to no staining observed using parental (untransfected) CHO cells.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from U.S. 61/052,865 and U.S. 60/969,118, the entire contents of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Adachi et al (1998) Immunity 9:143-150.
Almeida and Allshire (2005) TRENDS Cell Biol 15: 251-258.
Al-Mufti et al (1999) Am. J. Med. Genet. 85:66-75.
Bauer et al (2002) Int J Legal Med 116:39-42.
Belz et al (2004). Proc Natl Acad Sci USA 101:8670-8675.
Bird et al (1988) Blood 80:1418-1422.
Bonifaz et al (2002) J Exp Med 196:1627-1638.
Bourque (1995) Plant Sci. 105:125-149.
Caminschi et al (2006). DNA Seq. 17:8-14.
Carter et al (2006) J Immunol 177:2276-2284.
Chothia and Lesk (1987) J. Mol. Biol. 196:901-917.
Colcher et al (1986) Methods Enzymol. 121:802-816.
Corbett et al (2005) Eur J Immunol 35:2815-2825.
Demangel et al (2005) Mol Immunol 42:979-985.
den Haan et al (2000) J Exp Med 192:1685-1696.
Drickamer (1999) Cur. Opin Struct Biol 9:585-590.
Dudziak et al (2007) Science 315:107-111.
Dunbrack, et al (1997) Folding and Design, 2:R27-42.
Finkelman et al (1996). J Immunol 157:1406-1414.
Fuller et al (2007) J Biol Chem 282:12397-12409.
Galibert et al (2005) J Biol Chem 280:21955-21964.
Greenwood et al (1993) Eur J Immunol 23: 1098-1104.
Haseloff and Gerlach (1988) Nature 334:585-591.
Harayama (1998) Trends Biotechnol. 16:76-82.
Hochrein et al (2001) J Immunol 166:5448-5455.
Huston et al (1988) Proc Natl Acad Sci USA 85:5879-5883.
Jones et al (1986) Nature 321:522-525.
Lahoud et al (2006) J Immunol 177:372-382.
Leserman (2004) J Liposome Res 14:175-189.
Miller (1990) Blood 76:271-278.
Millar and Waterhouse (2005) Funct Integr Genomics 5:129-135.
Morrison et al (1984) Proc Natl Acad Sci USA 81:6851-6855.
Naik et al. (2005) J Immunol 174:6592-6597.
Naik et al (2006) Nat Immunol 7:663-671.
Nchinda et al (2008) J Clin Investig 118:1427-1436.
Needleman and Wunsch. (1970). J. Mol. Biol., 48, 443-453.
O'Keeffe et al (2002) J Exp Med 196:1307-1319.
O'Keeffe et al (2003) Blood 101:1453-1459.
Pasquinelli et al (2005) Curr Opin Genet Develop 15: 200-205.
Pastan et al (1986) Cell 47: 641-648.
Perriman et al (1992) Gene 113: 157-16.
Pooley et al (2001) J Immunol 166:5327-5330.
Proietto et al (2004) Immunobiology 209:163-172.
Schnorrer et al (2006) Proc Natl Acad Sci USA 103:10729-10734.
Senior (1998) Biotech. Genet. Engin. Revs. 15:79-119.
Shippy et al (1999) Mol. Biotech. 12: 117-129.
Shortman and Liu (2002) Nat Rev Immunol 2:153-163.
Shortman and Naik (2007). Nat Rev Immunol 7:19-30.
Smith et al (2003) J Immunol 170:4437-4440.
Smith et al (2000) Nature 407: 319-320.
Sun et al (1986) Hybridoma 5S1:517-520.
Takeda et al (2003) Annu Rev Immunol 21:335-376.
Thorpe et al (1987) Cancer Res 47: 5924-31.
Van Broekhoven et al (2004) Cancer Res 64:4357-4365.
Vandenabeele et al (2001) Blood 97:1733-1741.
Van de Velde et al (2006) Springer Semin Immunol 28:329-338.
Vitetta et al (1987) Science 238: 1098-1104.
Vremec et al (2000) J Immunol 164:2978-2986.
Waldmann (1991) Science 252: 1657-1662.
Waterhouse et al (1998) Proc. Natl. Acad. Sci. USA 95: 13959-13964.
Weis et al (1998) Immunol Rev. 163:19-34.
Yamamoto et al (2003) Science 301:640-643.

The invention claimed is:

1. A polypeptide consisting of a first amino acid sequence conjugated to a second amino acid sequence, wherein the second amino acid sequence is heterologous to the first amino acid sequence,
wherein the first amino acid sequence is a soluble fragment of a polypeptide comprising the amino acid sequence of SEQ ID NO:1 and wherein the first amino acid sequence consists of amino acids 67 through 241 of SEQ ID NO:1,
wherein the second amino acid sequence comprises the sequence of a cancer antigen,
wherein the cancer antigen is selected from the group consisting of Her2/neu, ErbB-2, p53, protein product of: Ras p21 protooncogene or BCR-abl oncogene, carcinoembryonic antigen (CEA), melanocyte differentiation antigen selected from the group consisting of Mart 1/Melan A, gp100, gp75, TRP1 and TRP2, prostate associated antigens selected from the group consisting of PSA, PAP, PSMA, PSM-P1 and PSM-P2, reactivated embryonic gene product selected from the group consisting of MAGE 1, MAGE 3, MAGE 4, GAGE 1, GAGE 2, BAGE, and RAGE, cancer testis antigen selected from the group consisting of NY-ESO1, SSX2 and SCP1, and mucins selected from the group consisting of Muc-1 and Muc-2.

2. The polypeptide of claim 1, wherein the cancer antigen is conjugated to the C-terminus of the first amino acid sequence.

3. A composition comprising:
the polypeptide claim 1;
and a pharmaceutically acceptable excipient.

4. The composition of claim 3, further comprising an adjuvant.

5. The polypeptide of claim 1, wherein the second amino acid sequence consists of the sequence of the cancer antigen.

6. The polypeptide of claim 1, wherein the cancer antigen is Her2/neu.

7. The polypeptide of claim 1, wherein the cancer antigen is ErbB-2.

* * * * *